(12) United States Patent
Bondinell et al.

(10) Patent No.: US 6,576,643 B2
(45) Date of Patent: Jun. 10, 2003

(54) VITRONECTIN RECEPTOR ANTAGONISTS

(75) Inventors: William E. Bondinell, Wayne, PA (US); William H. Miller, Schwenksville, PA (US); Dirk Heerding, Malvern, PA (US); James M. Samanen, Phoenixville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/022,987

(22) Filed: Dec. 17, 2001

(65) Prior Publication Data

US 2002/0091264 A1 Jul. 11, 2002

Related U.S. Application Data

(63) Continuation of application No. 09/508,574, filed as application No. PCT/US98/19466 on Sep. 18, 1998.
(60) Provisional application No. 60/063,438, filed on Oct. 29, 1997, and provisional application No. 60/059,342, filed on Sep. 19, 1997.

(51) Int. Cl.[7] ................... A61K 31/4375; C07D 217/22
(52) U.S. Cl. ................. 514/310; 514/275; 514/300; 514/337; 514/352; 514/370; 544/335; 546/122; 546/143; 546/281.7; 546/312; 548/204
(58) Field of Search .................. 514/275, 300, 514/310, 337, 352, 370; 544/335; 546/122, 143, 281.7, 312; 548/204

(56) References Cited

U.S. PATENT DOCUMENTS

| | | |
|---|---|---|
| 3,335,148 A | 8/1967 | Krumkalns |
| 3,726,870 A | 4/1973 | Rey-Bellet et al. |
| 5,659,033 A | 8/1997 | Yuan et al. |
| 5,780,486 A | 7/1998 | Jorgensen et al. |

FOREIGN PATENT DOCUMENTS

| | | |
|---|---|---|
| WO | WO 97/01540 | 1/1997 |
| WO | WO 98/15278 A | 4/1998 |
| WO | WO 98/30542 A | 7/1998 |

Primary Examiner—Joseph K. McKane
Assistant Examiner—Sonya Wright

(74) *Attorney, Agent, or Firm*—Laura K. Madden; Mary E. McCarthy; Charles M. Kinzig

(57) ABSTRACT

Compounds of the formula (I) are disclosed which are vitronectin receptor antagonists and are useful in the treatment of osteoporosis:

wherein:
A is $CH_2$ or O;
$R^1$ is H, halo or $C_{1-6}$alkyl;
$R^2$ is H, $C_{1-6}$alkyl or $CH_2NR''R''$;
X is O or $CH_2$;
Y is G is NR'', S or O;
R' is H, $C_{1-6}$alkyl, $OC_{1-6}$alkyl, $SC_{1-6}$alkyl, $NR''R''$ or halo;
each R'' independently is H or $C_{1-6}$alkyl; and
s is 0, 1, or 2;

or a pharmaceutically acceptable salt thereof.

10 Claims, No Drawings

VITRONECTIN RECEPTOR ANTAGONISTS

This is a continuation of application Ser. No. 09/508,574 filed Mar. 13, 2000 which is a 371 application of PCT/US98/19466 filed Sep. 18, 1998 which claims the benefit of provisional applications 60/059,342 filed Sep. 19, 1997 and 60/063,438 filed Oct. 29, 1997.

FIELD OF THE INVENTION

This invention relates to pharmaceutically active compounds which inhibit the vitronectin receptor and are useful for the treatment of inflammation, cancer and cardiovascular disorders, such as atherosclerosis and restenosis, and diseases wherein bone resorption is a factor, such as osteoporosis.

BACKGROUND OF THE INVENTION

Integrins are a superfamily of cell adhesion receptors, which are transmembrane glycoproteins expressed on a variety of ceils. These cell surface adhesion receptors include gpIIb/IIIa (the fibrinogen receptor) and $\alpha_v\beta_3$ (the vitronectin receptor). The fibrinogen receptor gpIIb/IIIa is expressed on the platelet surface, and mediates platelet aggregation and the formation of a hemostatic clot at the site of a bleeding wound. Philips, et at., *Blood.*, 1988, 71, 831. The vitronectin receptor $\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells mediates the adhesion of osteoclasts to the bone matrix, a key step in the bone resorption process. Ross, et al., *J. Biol. Chem.*, 1987, 262, 7703. A disease characterized by excessive bone resorption is osteoporosis. The $\alpha_v\beta_3$ receptor expressed on human aortic smooth muscle cells mediates their migration into neointima, a process which can lead to restenosis after percutaneous coronary angioplasty. Brown, et al., *Cardiovascular Res.*, 1994, 28, 1815. Additionally, Brooks, et al., *Cell*, 1994, 79, 1157 has shown that an $\alpha_v\beta_3$ antagonist is able to promote tumor regression by inducing apoptosis of angiogenic blood vessels. Thus, agents that block the vitronectin receptor would be useful in treating diseases, such as osteoporosis, restenosis and cancer.

The vitronectin receptor is now known to refer to three different integrins, designated $\alpha_v\beta_1$, $\alpha_v\beta_3$ and $\alpha_v\beta_5$. Horton, et al., *Int. J. Exp. Pathol*, 1990, 71, 741. $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteopontin and bone sialoprotein I. $\alpha_v\beta_5$ binds vitronectin. The vitronectin receptor $\alpha_v\beta_5$ has been shown to be involved in cell adhesion of a variety of cell types, including microvascular endothelial cells, (Davis, et al., *J. Cell. Biol.*, 1993, 51, 206), and its role in angiogenesis has been confirmed. Brooks, et al., *Science*, 1994, 264, 569. This integrin is expressed on blood vessels in human wound granulation tissue, but not in normal skin.

The vitronectin receptor is known to bind to bone matrix proteins which contain the tri-peptide Arg-Gly-Asp (or RGD) motif. Thus, Horton, et al. *Exp. Cell Res.* 1991, 195. 368. disclose that RGD-containing peptides and an anti-vitronectin receptor antibody (23C6) inhibit dentine resorption and cell spreading by osteoclasts In addition. Sato, et al. *J. Cell Biol.* 1990, 111, 1713 discloses that echistatin, a snake venom peptide which contains the RGD sequence, is a potent inhibitor of bone resorption in tissue culture and inhibits attachment of osteoclasts to bone.

It has now been discovered that certain compounds are potent inhibitors of the $\alpha_v\beta_3$ and $\alpha_v\beta_5$ receptors. In particular, it has been discovered that such compounds are more potent inhibitors of the vitronectin receptor than the fibrinogen receptor

SUMMARY OF THE INVENTION

This invention comprises compounds of the formula (I) as described hereinafter, which have pharmacological activity for the inhibition of the vitronection receptor and are useful in the treatment of inflammation, cancer and cardiovascular disorders, such as atherosclerosis and restenosis, and diseases wherein bone resorption is a factor, such as osteoporosis.

This invention is also a pharmaceutical composition comprising a compound according to formula (I) and a pharmaceutically carrier.

This invention is also a method of treating diseases which are mediated by the vitronectin receptor. In a particular aspect, the compounds of this invention are useful for treating atherosclerosis, restenosis, inflammation, cancer and diseases wherein bone resorption is a factor, such as osteoporosis.

DETAILED DESCRIPTION

This invention comprises novel compounds which are more potent inhibitors of the vitronectin receptor than the fibrinogen receptor. The novel compounds comprise a dibenzocycloheptene core in which a nitrogen-containing substituent is present on one of the aromatic six-membered rings of the dibenzocycloheptene and an aliphatic substituent containing an acidic moiety is present on the seven-membered ring of the dibenzocycloheptene. The dibenzocycloheptene ring system is believed to orient the substituent sidechains on the six and seven membered rings so that they may interact favorably with the vitronectin receptor. It is preferred that about twelve to fourteen intervening covalent bonds via the shortest intramolecular path will exist between the acidic group on the aliphatic substituent of the seven-membered ring of the dibenzocycloheptene and the nitrogen of the nitrogen-containing substituent on one of the aromatic six-membered ring of the dibenzocycloheptene.

This invention comprises compounds of formula (I):

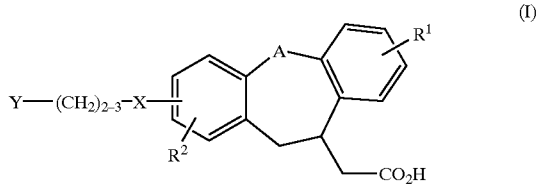

wherein:
A is $CH_2$ or O;
$R^1$ is H, halo or $C_{1-6}$alkyl;
$R^2$ is H, $C_{1-6}$alkyl or $CH_2NR''R''$;
X is O or $CH_2$;
Y is

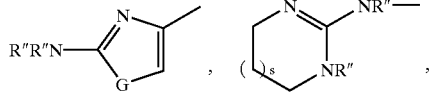

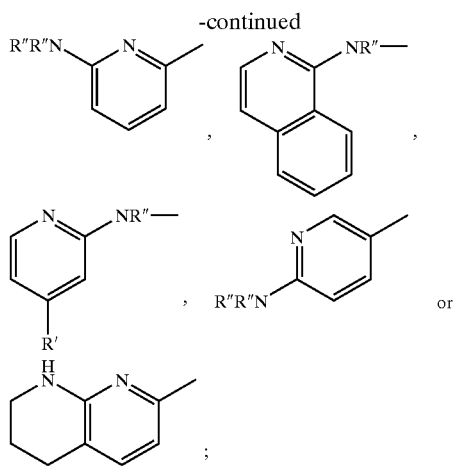

G is NR″, S or O;
R′ is H, C$_{1-6}$alkyl, OC$_{1-6}$alkyl, SC$_{1-6}$alkyl, NR″R″ or halo;
each R″ independently is H or C$_{1-6}$alkyl; and
s is 0, 1, or 2;

or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique nonracemic compound which may be synthesized and resolved by conventional techniques. In cases in which compounds have unsaturated carbon—carbon double bonds, both the cis (Z) and trans (E) isomers are within the scope of this invention. In cases wherein compounds may exist in tautomeric forms, such as keto-enol tautomers, such as

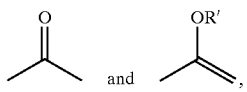

and each tautomeric form is contemplated as being included within this invention whether existing in equilibrium or locked in one form by appropriate substitution with R′.

The compounds of formula (I) inhibit the binding of vitronectin and other RGD-containing peptides to the vitronectin receptor. Inhibition of the vitronectin receptor on osteoclasts inhibits osteoclastic bone resorption and, is useful in the treatment of diseases wherein bone resorption is associated with pathology, such as osteoporosis and osteoarthritis.

In another aspect, this invention is a method for stimulating bone formation which comprises administering a compound which causes an increase in osteocalcin release. Increased bone production is a clear benefit in disease states wherein there is a deficiency of mineralized bone mass or remodeling of bone is desired, such as fracture healing and the prevention of bone fractures. Diseases and metabolic disorders which result in loss of bone structure would also benefit from such treatment. For instance, hyperparathyroidism, Paget's disease, hypercalcemia of malignancy, osteolytic lesions produced by bone metastasis, bone loss due to immobilization or sex hormone deficiency, Behcet's disease, osteomalacia, hyperostosis and osteopetrosis, could benefit from administering a compound of this invention.

Additionally, since the compounds of the instant invention inhibit vitronectin receptors on a number of different types of cells, said compounds would be useful in the treatment of inflammatory disorders, such as rheumatoid arthritis and psoriasis, and cardiovascular diseases, such as atherosclerosis and restenosis. The compounds of Formula (I) of the present invention may be useful for the treatment or prevention of other diseases including, but not limited to, thromboembolic disorders, asthma, allergies, adult respiratory distress syndrome, graft versus host disease, organ transplant rejection, septic shock, eczema, contact dermatitis, inflammatory bowel disease, and other autoimmune diseases. The compounds of the present invention may also be useful for wound healing.

The compounds of the present invention are also useful for the treatment, including prevention, of angiogenic disorders. The term angiogenic disorders as used herein includes conditions involving abnormal neovascularization. Where the growth of new blood vessels is the cause of, or contributes to, the pathoogy associated with a disease, inhibition of angiogenisis will reduce the deleterious effects of the disease. An example of such a disease target is diabetic retinopathy. Where the growth of new blood vessels is required to support growth of a deleterious tissue, inhibition of angiogenisis will reduce the blood supply to the tissue and thereby contribute to reduction in tissue mass based on blood supply requirements. Examples include growth of tumors where neovascularization is a continual requirement in order that the tumor grow and the establishment of solid tumor metastases. Thus the compounds of the present invention inhibit tumor tissue angiogenesis, thereby preventing tumor metastasis and tumor growth.

Thus, according to the methods of the present invention, the inhibition of angiogenesis using the compounds of the present invention can ameliorate the symptoms of the disease, and, in some cases, can cure the disease.

Another therapeutic target for the compounds of the instant invention are eye diseases chacterized by neovascuiarization. Such eye diseases include corneal neovascular disorders, such as corneal transplantation herpetic keratitis, luetic keratitis, pterygium and neovascular pannus associated with contact lens use. Additional eye diseases also include age-related macular degeneration, presumed ocular histoplasmosis, retinopathy of prematurity and neovascular glaucoma.

This invention further provides a method of inhibiting tumor growth which comprises administering stepwise or in physical combination a compound of formula (I) and an antineoplastic agent, such as topotecan and cisplatin.

With respect to formula (I):

Suitably Y is

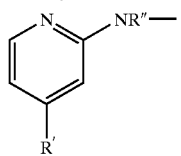

, wherein R′ is H, C$_{1-4}$alkyl, OC$_{1-4}$alkyl, SC$_{1-4}$alkyl, NR″R″ or Cl and each R″ independently is H or C$_{1-4}$alkyl.

Alternately, Y is

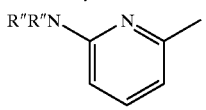

, wherein each R″ is H or C$_{1-4}$alkyl.

-continued

Alternately, Y is

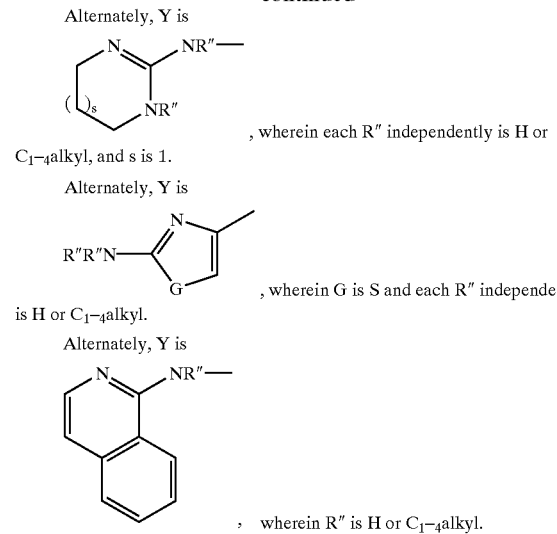

, wherein each R″ independently is H or C$_{1-4}$alkyl, and s is 1.

Alternately, Y is

, wherein G is S and each R″ independently is H or C$_{1-4}$alkyl.

Alternately, Y is

, wherein R″ is H or C$_{1-4}$alkyl.

Representative of the novel compounds of this invention are the following:

(±)-10,11-Dihydro-3-[2-(6-aminopyridin-2-yl)-1-ethoxy]-5H-dibenzo[a,d]cycloheptene-10-acetic acid;
(±)-10,11-Dihydro-3-[4-(pyridin-2-ylamino)-1-butyl]-5H-dibenzo[a,d]cycloheptene-10-acetic acid;
(±)-10,11-Dihydro-3-[3-(4-ethoxypyridin-2-ylamino)-1-propyloxy]-5H-dibenzo[a,d]cycloheptene-10-acetic acid;
(S)-10,11-Dihydro-3-[3-(pyridin-2-ylamino)-1-propyloxy]-5H-dibenzo[a,d]cycloheptene-10-acetic acid;
(R)-10,11-Dihydro-3-[3-(pyridin-2-ylamino)-1-propyloxy]-5H-dibenzo[a,d]cycloheptene-10-acetic acid;
(±)-10,11-Dihydro-3-[3-(3,4,5,6-tetrahydropyrimidin-2-ylamino)-1-propyloxy]-5H-dibenzo[a,d]cycloheptene-10-acetic acid;
(±)-10,11-Dihydro-3-[2-[2-(ethylamino)thiazol-4-yl]-1-ethoxy]-5H-dibenzo[a,d]cycloheptene-10-acetic acid;
(±)-10,11-Dihydro-3-[3-(isoquinoline-1-ylamino)-1-propyloxy]-5H-dibenzo[a,d]cycloheptene-10-acetic acid;
(±)-10,11-Dihydro-7-fluoro-3-[3-(pyridin-2-ylamino)-1-propyloxy]-5H-dibenzo[a,d]cycloheptene-10-acetic acid;
(S)-10,11-Dihydro-3-[3-(4-methylpyridin-2-ylamino)-1-propyloxy]-5H-dibenzo[a,d]cycloheptene-10-acetic acid;
(S)-10,11-Dihydro-3-[3-(4-ethoxypyridin-2-ylamino)-1-propyloxy]-5H-dibenzo[a,d]cycloheptene-10-acetic acid;
(±)-10,11-Dihydro-6-methyl-3-[3-(pyridin-2-ylamino)-1-propyloxy]-5H-dibenzo[a,d]cycloheptene-10-acetic acid;
(±)-10,11-Dihydro-2-(dimethylamino)methyl-7-fluoro-3-[3-(pyridin-2-ylamino)-1-propyloxy]-5H-dibenzo[a,d]cycloheptene-10-acetic acid;
(S)-10,11-Dihydro-3-[3-[4-(2-propyloxy)pyridin-2-ylamino]-1-propyloxy]-5H-dibenzo[a,d]cycloheptene-10-acetic acid;
(S)-10,11-Dihydro-3-[2-[6-(methylamino)pyridin-2-yl]-1-ethoxy]-5H-dibenzo[a,d]cycloheptene-10-acetic acid;
(S)-10,11-Dihydro-3-[3-[4-(dimethylamino)pyridin-2-ylamino]-1-propyloxy]-5H-dibenzo[a,d]cycloheptene-10-acetic acid;
(±)-10,11-Dihydro-3-[3-[4-(ethylthio)pyridin-2-ylamino]-1-propyloxy]-5H-dibenzo[a,d]cycloheptene-10-acetic acid;
(S)-10,11-Dihydro-3-[3-(4-chloropyridin-2-ylamino)-1-propyloxy]-5H-dibenzo[a,d]cycloheptene-10-acetic acid;
(±)-10,11-Dihydro-2-methyl-3-[3-(pyridin-2-ylamino)-1-propyloxy]-5H-dibenzo[a,d]cycloheptene-10-acetic acid;
(S)-10,11-Dihydro-3-[3-(4-aminopyridin-2-ylamino)-1-propyloxy]-5H-dibenzo[a,d]cycloheptene-10-acetic acid;
(±)-10,11-Dihydro-3-[3-(4-methylpyridin-2-ylamino)-1-propyloxy]-dibenzo[b,f]oxepine-10-acetic acid;
(±)-10,11-Dihydro-3-[2-[6-(methylamino)pyridin-2-yl]-1-ethoxy]-dibenzo[b,f]oxepine-10-acetic acid; and
(S)-10,11-Dihydro-3-[3-(2-aminopyridin-4-yl)-1-propyloxy]-5H-dibenzo[a,d]cycloheptene-10-acetic acid;
or a pharmaceutically acceptable salt thereof.

In cases wherein the compounds of this invention may have one or more chiral centers, unless specified, this invention includes each unique nonracemic compound which may be synthesized and resolved by conventional techniques. According to the present invention, the (S) configuration of the formula (I) compounds is preferred.

In cases in which compounds have unsaturated carbon—carbon double bonds, both the cis (Z) and trans (E) isomers are within the scope of this invention. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in vivo. Thus, in another aspect of this invention are novel prodrugs, which are also intermediates in the preparation of formula (I) compounds, of formula (II):

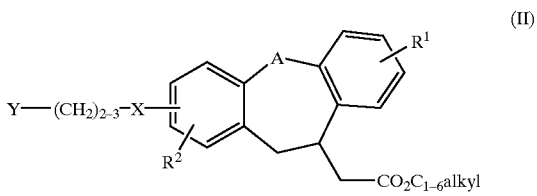

(II)

wherein:
A is CH$_2$ or O;
R$^1$ is H, halo or C$_{1-6}$alkyl;
R$^2$ is H, C$_{1-6}$alkyl or CH$_2$NR″R″;
X is O or CH$_2$;
Y is

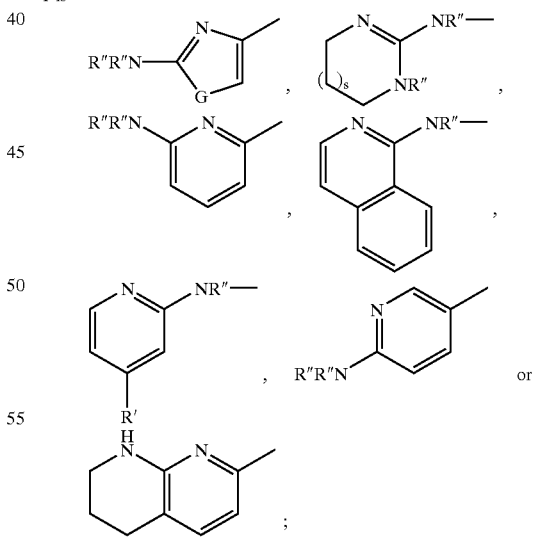

;

G is NR″, S or O;
R′ is H, C$_{1-6}$alkyl, OC$_{1-6}$alkyl, SC$_{1-6}$alkyl, NR″R″ or halo;
each R″ independently is H or C$_{1-6}$alkyl; and
s is 0, 1, or 2;

or a pharmaceutically acceptable salt thereof.

In yet another aspect of this invention are novel intermediates of formula (III):

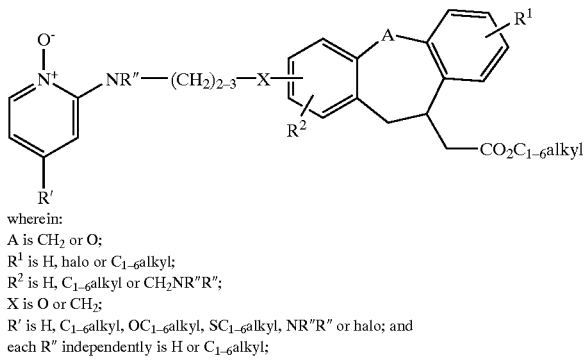

(III)

wherein:
A is CH$_2$ or O;
R$^1$ is H, halo or C$_{1-6}$alkyl;
R$^2$ is H, C$_{1-6}$alkyl or CH$_2$NR"R";
X is O or CH$_2$;
R' is H, C$_{1-6}$alkyl, OC$_{1-6}$alkyl, SC$_{1-6}$alkyl, NR"R" or halo; and
each R" independently is H or C$_{1-6}$alkyl;

or a pharmaceutically acceptable salt thereof.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Riochem.*, 158, 9 (1984).

C$_{1-4}$alkyl as applied herein means an optionally substituted alkyl group of 1 to 4 carbon atoms, and includes methyl, ethyl, n-propyl, isopropyl, n-butyl, isobutyl and t-butyl. C$_{1-6}$alkyl additionally includes pentyl, n-pentyl, isopentyl, neopentyl and hexyl and the simple aliphatic isomers thereof. C$_{0-4}$alkyl and C$_{0-6}$alkyl additionally indicates that no alkyl group need be present (e.g., that a covalent bond is present).

Any C$_{1-4}$alkyl or C$_{1-6}$alkyl may be optionally substituted with the group R$^x$, which may be on any carbon atom that results in a stable structure and is available by conventional synthetic techniques. Suitable groups for R$^x$ are C$_{1-4}$alkyl, OR", SR", C$_{1-4}$alkylsulfonyl, C$_{1-4}$alkylsulfoxyl, —CN, N(R")$_2$, CH$_2$N(R")$_2$, —NO$_2$, —CF$_3$, —CO$_2$R", —CON(R")$_2$, —COR", —NR"C(O)R", F, Cl, Br, I, or CF$_3$S(O)$_r$—, wherein r is 0, 1 or 2.

Halogen or halo means F, Cl, Br, and I.

Ar, or aryl, as applied herein, means phenyl or naphthyl, or phenyl or naphthyl substituted by one to three substituents, such as those defined above for alkyl, especially C$_{1-4}$alkyl, C$_{1-4}$alkoxy, C$_{1-4}$alkthio, CF$_3$, NH$_2$, OH, F, Cl, Br or I.

Certain radical groups are abbreviated herein t-Bu refers to the tertiary butyl radical, Boc refers to the t-butyloxycarbonyl radical, Frnoc refers to the fluorenylmethoxycarbonyl radical, Ph refers to the phenyl radical, Cbz refers to the benzyloxycarbonyl radical, Bn refers to the benzyi radical, Me refers to methyl, Et refers to ethyl. Ac refers to acetyl, Alk refers to C$_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, DIEA refers to dilsopropylethyl amine, EDC refers to 1-(3-dimethylaminopropyl)-3-ethylcarboduimide, hydrochloride. HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of formula (IV) with a compound of formula (V):

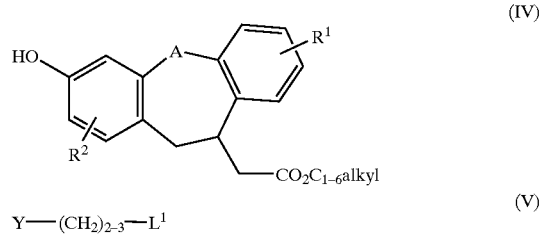

(IV)

(V)

wherein R$^1$, R$^2$, Y and A are as defined in formula (I), with any reactive functional groups protected, and L$^1$ is OH or halo;

and thereafter removing any protecting groups, and optionally forming a pharmaceutically acceptable salt.

Suitably, certain compounds of formula (I) are prepared by reacting a compound of formula (IV) with a compound of formula (VI):

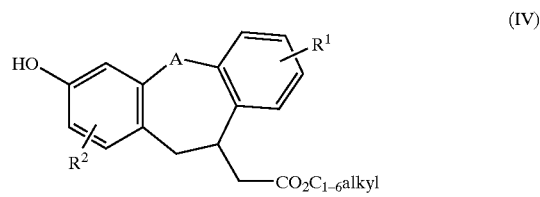

(IV)

(VI)

wherein R$^1$, R$^2$, R', R" and A are as defined in formula (I), with any reactive functional groups protected;

and thereafter removing any protecting groups, and optionally forming a pharmaceutically acceptable salt.

Suitably, the reaction between a compound of formula (IV) with a compound of formula (VI) is carried out in the presence of diethyl azodicarboxylate and triphenylphosphine in an aprotic solvent.

Additionally, certain compounds of formula (I) are prepared by reacting a compound of formula (IV) with a compound of formula (VII):

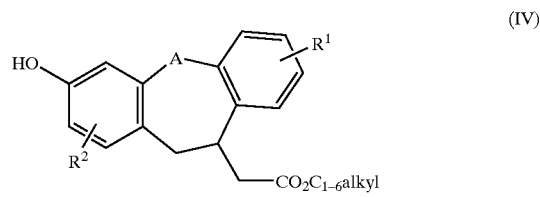

(IV)

-continued

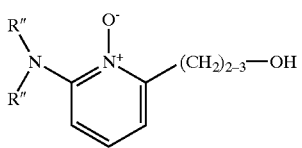

(VII)

wherein $R^1$, $R^2$, $R''$ and A are as defined in formula (I), with any reactive functional groups protected;
and thereafter removing any protecting groups, and optionally forming a pharmaceutically acceptable salt.

Suitably, the reaction between a compound of formula (IV) with a compound of formula (VII) is carried out in the presence of diethyl azodicarboxylate and triphenylphosphine in an aprotic solvent.

Compounds of the formula (I) are prepared by the methods described in Bondinell et al., PCT Publication No. WO 97/01540 (International Application No. PCT/US96/11108), published Jan. 16, 1997, the entire disclosure of which is incorporated herein by reference.

Additionally, compounds of formula (I) are prepared by methods analogous to those described in the schemes that are detailed hereinafter.

Scheme I

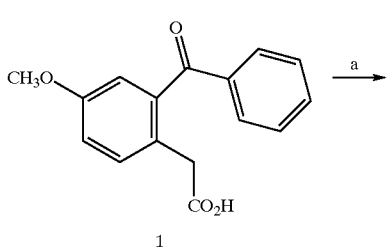

1

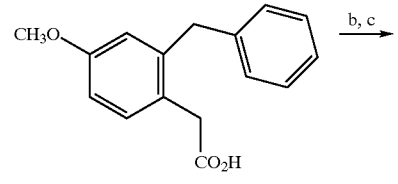

2

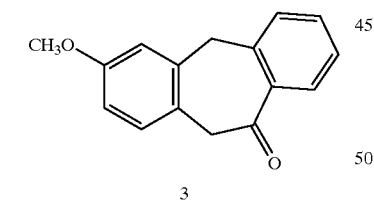

3 a) 10% Pd/C, HOAc; b) SOCl₂, toluene; c) AlCl₃, CH₂Cl₂

Scheme I details the preparation of an intermediate useful in the preparation of formula (I) compounds.

Scheme II

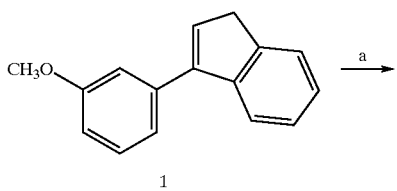

1

-continued

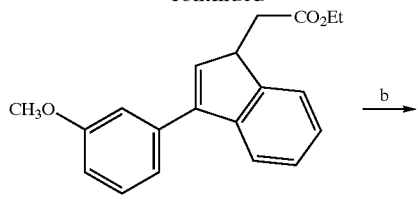

2

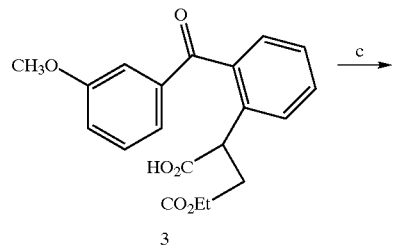

3

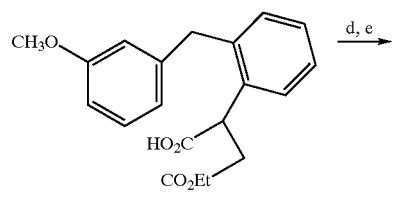

4

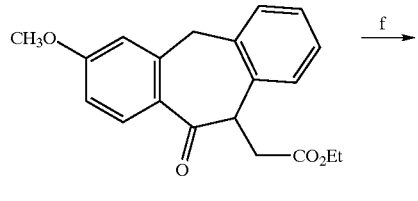

5

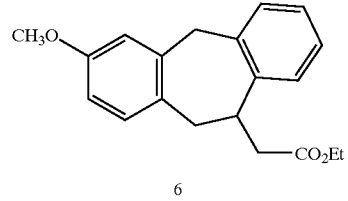

6 a) LiN(TMS)₂, ethyl bromoacetate; b) Jones reagent, OsO₄; c) H₂, 10% Pd/C, HOAc; d) C₂O₂Cl₂, DMF; e) AlCl₃, CH₂Cl₂, RT; f) H₂, 10% Pd/C, HOAC Scheme II also details the preparation of an intermediate useful in the preparation of formula (I) compounds.

Scheme III

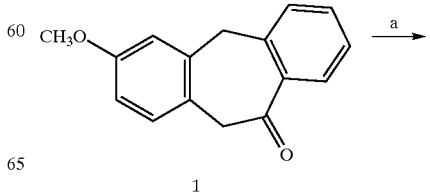

1

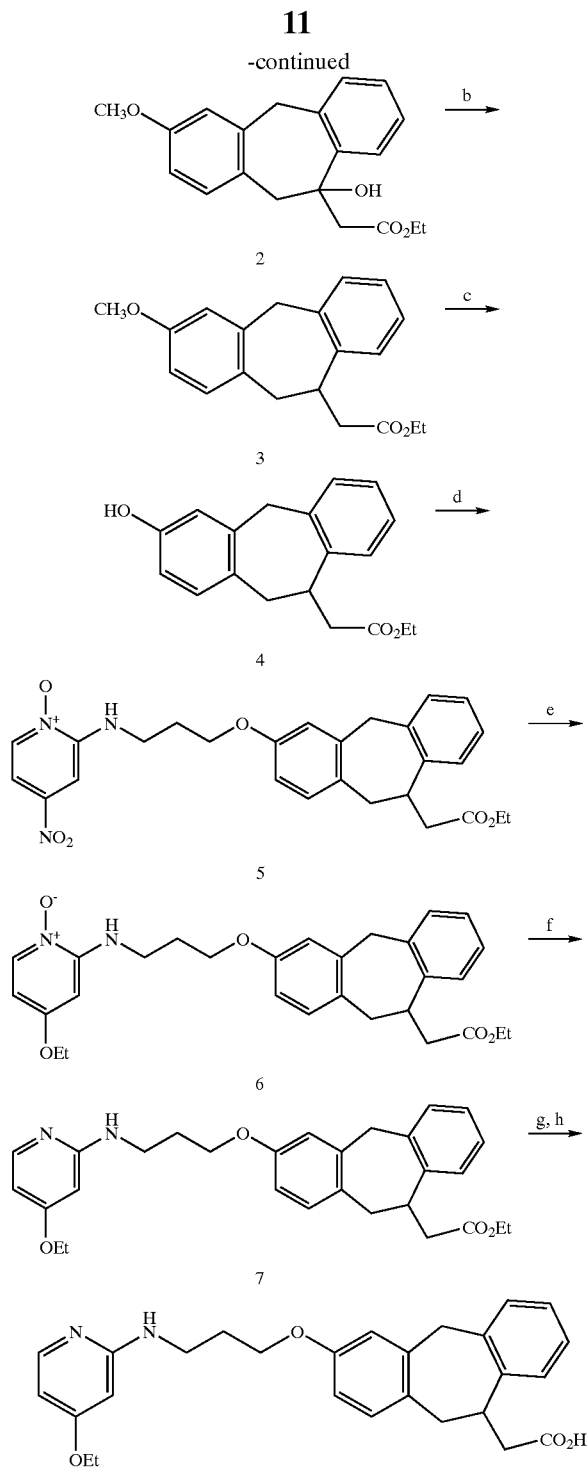

(a) EtOAc/LiHMDS, THF; (b) H₂, 10% Pd/C, conc. HCl, AcOH; (c) EtSH, AlCl₃, CH₂Cl₂; (d) 2-[(3-hydroxy-1-propyl)amino]-4-nitropyridine-N-oxide, DEAD, (Ph)₃P; (e) NaOEt, EtOH; (f) cyclohexene, 10% Pd/C, EtOH; (g) 1.0 N NaOH, EtOH; (h) HCl.

Scheme III details the preparation of a formula (I) compound. Reaction of III-1 (which is a Scheme I-3 compound) in an aldol-type reaction with the enolate of ethyl acetate, which can be generated from ethyl acetate on exposure to an appropriate amide base, for instance lithium diusopropylamide (LDA) or lithium bis(trimethylsilyl)amide (LiHMDS), gives III-2. Frequently, THF is the solvent of choice for an aldol reaction, although THF in the presence of various additives, for instance HMPA or TMEDA, is often used. Reduction of III-2 to give III-3 (which is a Scheme II-6 compound) can be accomplished by hydrogenolysis over an appropriate catalyst, for example palladium metal on activated carbon (Pd/C), in an appropriate solvent, such as acetic acid, in the presence of a mineral acid such as HCl. Alternatively, this reduction can be accomplished by treatment of III-2 with triethylsilane in the presence of boron trifluoride etherate by the general method of Orfanopoulos and Smonou (*Synth. Commun.* 1988, 833). Removal of the methyl ether of III-3 to give III-4 can be accomplished with BBr₃ in an inert solvent, for example CH₂Cl₂, or by reaction with ethanethiol and AlCl₃ in an inert solvent, preferably CH₂Cl₂. Other useful methods for removal of a methyl ether are described in Greene, "Protective Groups in Organic Synthesis" (published by John Wiley and Sons). Compound 4 of Scheme 3 (III-4) is reacted with 2-[(3-hydroxy-1-propyl)amino]-4-nitropyridine-N-oxide in a Mitsunobu-type coupling reaction (*Organic Reactions* 1992, 42, 335–656; *Synthesis* 1981, 1–28) to afford III-5. The reaction is mediated by the complex formed between diethyl azodicarboxylate and triphenylphosphine, and is conducted in an aprotic solvent, for instance THF, CH₂Cl₂, or DMF. Compound III-5 is reacted with an alkali metal salt of an appropriate alcohol to afford III-6. Suitable alkali metals include lithium, sodium, potassium, and cesium, and the alcohol used for the displacement reaction is generally used as the solvent. Methods for forming the alkali metal salts of alcohols are well-known to those of skill in the art. The pyridine-N-oxide moiety of III-6 is reduced to the corresponding pyridine III-7 under transfer hydrogenation conditions using a palladium catalyst, preferably palladium metal on activated carbon, in an inert solvent, for instance methanol, ethanol, or 2-propanol. Cyclohexene, 1,4-cyclohexadiene, formic acid, and salts of formic acid, such as potassium formate or ammonium formate, are commonly used as the hydrogen transfer reagent in this type of reaction. The ethyl ester of III-7 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid III-8. Alternatively, the intermediate carboxylate salt can be isolated, if desired, or a carboxylate salt of the free carboxylic acid can be prepared by methods well-known to those of skill in the art.

Scheme IV

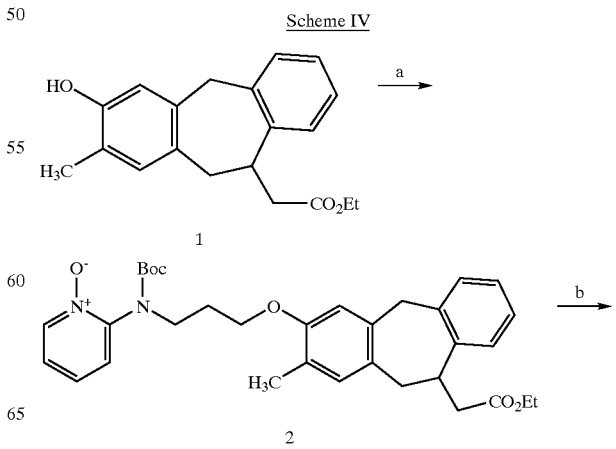

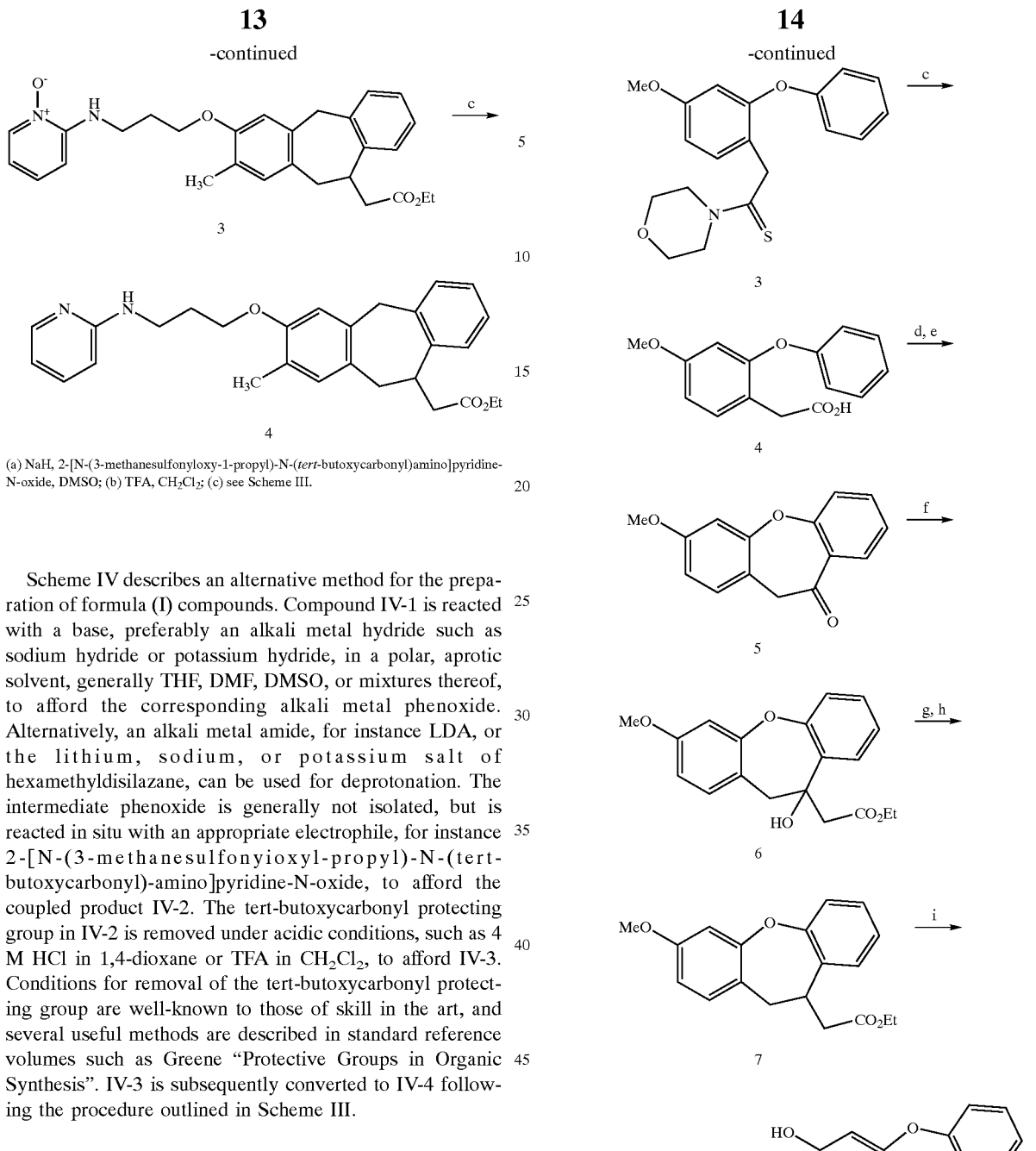

(a) NaH, 2-[N-(3-methanesulfonyloxy-1-propyl)-N-(*tert*-butoxycarbonyl)amino]pyridine-N-oxide, DMSO; (b) TFA, CH$_2$Cl$_2$; (c) see Scheme III.

Scheme IV describes an alternative method for the preparation of formula (I) compounds. Compound IV-1 is reacted with a base, preferably an alkali metal hydride such as sodium hydride or potassium hydride, in a polar, aprotic solvent, generally THF, DMF, DMSO, or mixtures thereof, to afford the corresponding alkali metal phenoxide. Alternatively, an alkali metal amide, for instance LDA, or the lithium, sodium, or potassium salt of hexamethyldisilazane, can be used for deprotonation. The intermediate phenoxide is generally not isolated, but is reacted in situ with an appropriate electrophile, for instance 2-[N-(3-methanesulfonyioxyl-propyl)-N-(tert-butoxycarbonyl)-amino]pyridine-N-oxide, to afford the coupled product IV-2. The tert-butoxycarbonyl protecting group in IV-2 is removed under acidic conditions, such as 4 M HCl in 1,4-dioxane or TFA in CH$_2$Cl$_2$, to afford IV-3. Conditions for removal of the tert-butoxycarbonyl protecting group are well-known to those of skill in the art, and several useful methods are described in standard reference volumes such as Greene "Protective Groups in Organic Synthesis". IV-3 is subsequently converted to IV-4 following the procedure outlined in Scheme III.

Scheme V

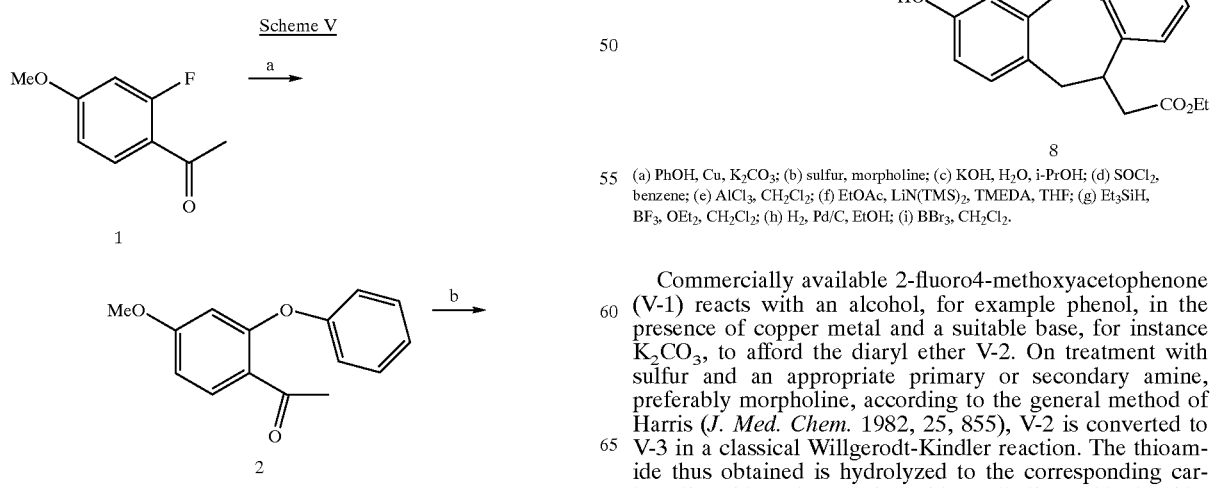

(a) PhOH, Cu, K$_2$CO$_3$; (b) sulfur, morpholine; (c) KOH, H$_2$O, i-PrOH; (d) SOCl$_2$, benzene; (e) AlCl$_3$, CH$_2$Cl$_2$; (f) EtOAc, LiN(TMS)$_2$, TMEDA, THF; (g) Et$_3$SiH, BF$_3$, OEt$_2$, CH$_2$Cl$_2$; (h) H$_2$, Pd/C, EtOH; (i) BBr$_3$, CH$_2$Cl$_2$.

Commercially available 2-fluoro4-methoxyacetophenone (V-1) reacts with an alcohol, for example phenol, in the presence of copper metal and a suitable base, for instance K$_2$CO$_3$, to afford the diaryl ether V-2. On treatment with sulfur and an appropriate primary or secondary amine, preferably morpholine, according to the general method of Harris (*J. Med. Chem.* 1982, 25, 855), V-2 is converted to V-3 in a classical Willgerodt-Kindler reaction. The thioamide thus obtained is hydrolyzed to the corresponding carboxylic acid V-4 by reaction with an alkali metal hydroxide, suitably KOH, in an aqueous alcoholic solvent, such as aqueous MeOH, EtOH, or i-PrOH. Carboxylic acid V-4 is converted to the corresponding acid chloride by reaction with either $SOCl_2$ or oxalyl chloride according to conditions well-known to those of skill in the art. Treatment of this acid chloride with an appropriate Friedel-Crafts catalyst such as $AlCl_3$ or $SnCl_4$, in an inert solvent, such as $CH_2Cl_2$ or $CS_2$, provides the cyclic ketone V-5. Alternatively, acid V-4 can be converted directly to ketone V-5 under acidic conditions, for example with polyphosphoric acid. Reaction of V-5 in an aldol-type reaction with the enolate of ethyl acetate, which can be generated from ethyl acetate on exposure to an appropriate amide base, for instance lithium diisopropylamide (LDA) or lithium bis(trimethylsilyl)amide (LiHMDS), glues V-6. Frequently, THF is the solvent of choice for an aldol reaction, although THF in the presence of various additives, for instance HMPA or TMEDA is often used. Reduction of V-6 to give V-7 can be accomplished by treatment of V-6 with triethylsilane in the presence of boron trifluoride etherate by the general method of Orphanopoulos and Smonu (*Synth. Commun.* 1988, 833). Any olefinic by-products that result from elimination of the alcohol are reduced by hydrogenation over an appropriate catalyst, for example palladium metal on activated carbon (Pd/C), in an appropriate solvent, such as MeOH or EtOH. Alternatively, the reduction of V-6 to give V-7 can be accomplished by hydrogenolysis in the presence of a mineral acid such as HCl. Typically, this reaction is catalyzed by Pd/C, and is optimally conducted in acetic acid. Removal of the methyl ether of V-7 to give V-8 can be accomplished with $BBr_3$ in an inert solvent, for example $CH_2Cl_2$, or by reaction with ethanethiol and $AlCl_3$ in an inert solvent, preferably $CH_2Cl_2$. Other useful methods for removal of a methyl ether are described in Greene, "Protective Groups in Organic Synthesis" (published by John Wiley and Sons). V-8 is subsequently converted to formula (I) compounds following the procedure outlined in Scheme III.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insulation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis, hyperparathyroidism. Paget's disease, hypercalcemia of malignancy, osteolytic lesions produced by bone metastasis, bone loss due to immobilization or sex hormone deficiency. The compounds of this invention are also believed to have utility as antitumor, anti-angiogenic, anti-inflammatory and anti-metastatic agents, and be useful in the treatment of atherosclerosis and restenosis.

The compound is administered either orally or parenterally to the patient, in a manner such that the concentration of drug is sufficient to inhibit bone resorption or other such indication. The pharmaceutical composition containing the compound is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kg/day. The precise level and method by which the compounds are administered is readily determined by one routinely skilled in the art by comparing the blood level of the agent to the concentration required to have a therapeutic effect.

This invention further provides a method for treating osteoporosis or inhibiting bone loss which comprises administering stepwise or in physical combination a compound of formula (I) and other inhibitors of bone resorption such as bisphosphonates (i.e., allendronate), hormone replacement therapy, anti-estrogens, or calcitonin. In addition, this invention provides a method of treatment using a compound of this invention and an anabolic agent, such as the bone morphogenic protein, iproflavone, useful in the prevention of bone loss and/or to increase bone mass.

Additionally, this invention provides a method of inhibiting tumor growth which comprises administering stepwise or in physical combination a compound of formula (I) and an antineoplastic agent. Compounds of the camptothecin analog class, such as topotecan, irinotecan and 9-aminocamptothecin, and platinum coordination complexes, such as cisplatin, ormaplatin and tetraplatin, are well known groups of antineoplastic agents. Compounds of the camptothecin analog class are described in U.S. Pat. Nos. 5,004,758, 4,604,463, 4,473,692, 4,545,880 4,342,776, 4,513,138, 4,399,276, EP Patent Application Publication Nos. 0 418 099 and 0 088 642, Wani, et al., *J. Med. Chem.*, 1986, 29, 2358, Wani, et al., *J. Med. Chem.*, 1980, 23, 554, Wani, et al., *J. Med. Chem.*, 1987, 30, 1774, and Nitta et al., *Proc. 14th International Congr. Chemotherapy.*, 1985, *Anticancer Section* 1, 28, the entire disclosure of each which is hereby incorporated by reference. The platinum coordination complex, cisplatin, is available under the name Platinol® from Bristol Myers-Squibb Corporation. Useful formulations for cisplatin are described in U.S. Pat. Nos. 5,562,925 and 4,310,515, the entire disclosure of each which is hereby incorporated by reference.

In the method of inhibiting tumor growth which comprises administering stepwise or in physical combination a compound of formula (I) and an antineoplastic agent, the platinum coordination compound, for example cisplatin, can be administered using slow intravenous infusion. The preferred carrier is a dextrose/saline solution containing mannitol. The dose schedule of the platinum coordination compound may be on the basis of from about 1 to about 500 mg per square meter ($mg/m^2$) of body surface area per course of treatment. Infusions of the platinum coordination compound may be given one to two times weekly, and the weekly treatments may be repeated several times. Using a compound of the camptothecin analog class in a parenteral administration, the course of therapy generally employed is from about 0.1 to about 300.0 $mg/m^2$ of body surface area per day for about five consecutive days. Most preferably, the course of therapy employed for topotecan is from about 1.0 to about 2.0 $mg/nm^2$ of body surface area per day for about five consecutive days. Preferably, the course of therapy is repeated at least once at about a seven day to about a twenty-eight day interval.

The pharmaceutical composition may be formulated with both the compound of formula (I) and the antineoplastic agent in the same container, but formualtion in different containers is preferred. When both agents are provided in solution form, they can be contained in an infusion/injection system for simultaneous administration or in a tandem arrangement.

For convenient administration of the compound of formula (I) and the antineoplastic agent at the same or different times, a kit is prepared, comprising, in a single container, such as a box, carton or other container, individual bottles, bags, vials or other containers each having an effective amount of the compound of formula (I) for parenteral administration, as described above, and an effective amount of the antineoplastic agent for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the antineoplastic agent and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the compound of formula (I) may be in an i.v. injectable form, or infusion bag linked in series, via tubing, to the antineoplastic agent in a second infusion bag. Using such a system, a patient can receive an initial bolus-type injection or infusion of the compound of formula (I) followed by an infusion of the antineoplastic agent.

The compounds may be tested in one of several biological assays to determine the concentration of compound which is required to have a given pharmacological effect.

Inhibition of Vitronectin Binding

Solid-Phase [$^3$H]-SK&F-107260 Binding to $\alpha_v\beta_3$: Human placenta or human platelet $\alpha_v\beta_3$ (0.1–0.3 mg/mL) in buffer T (containing 2 mM $CaCl_2$ and 1% octyiglucoside) was diluted with buffer T containing 1 mM $CaCl_2$, 1 mM $MgCl_2$, 1 mM $MgCl_2$ (buffer A) and 0.05% $NaN_3$, and then immediately added to 96-well ELISA plates (Corning, New York, N.Y.) at 0.1 mL per well. 0.1–0.2 µg of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4), 100 mM NaCl, 1 mM $CaCl_2$, 1 mM $MnCl_2$, 1 mM $MgCl_2$) to a final compound concentration of 100 µM. This solution is then diluted to the required final compound concentration. Various concentrations of unlabeled antagonists (0.001–100 µM) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 µM SK&F-107260 and was consistently less than 1% of total radioligand input. The $IC_{50}$ (concentration of the antagonist to inhibit 50% binding of [$^3$H]-SK&F-107260) was determined by a nonlinear, least squares curve-fitting routine, which was modified from the LUNDON-2 program. The $K_i$ (dissociation constant of the antagonist) was calculated according to the equation: $K_i=IC_{50}/(1+L/K_d)$, where L and $K_d$ were the concentration and the dissociation constant of [$^3$H]-SK&F-107260, respectively.

Compounds of the present invention inhibit vitronectin binding to SK&F 107260 in the concentration range of about 2.5 to about 0.001 micomolar.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

Vascular Smooth Muscle Cell Migration Assay

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of $2.5-5.0 \times 10^6$ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% $CO_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

Thyroparathyroidectomized Rat Model

Each experimental group consists of 5–6 adult male Sprague-Dawley rats (250–400 g body weight). The rats are thyroparathyroidectomized (by the vendor, Taconic Farms) 7 days prior to use. All rats receive a replacement dose of thyroxine every 3 days. On receipt of the rats, circulating ionized calcium levels are measured in whole blood immediately after it has been withdrawn by tail venipuncture into heparinized tubes. Rats are included if the ionized Ca level (measured with a Ciba-Corning model 634 calcium pH analyzer) is <1.2 mM/L. Each rat is fitted with an indwelling venous and arterial catheter for the delivery of test material and for blood sampling respectively. The rats are then put on a diet of calcium-free chow and deionized water. Baseline Ca levels are measured and each rat is administered either control vehicle or human parathyroid hormone 1–34 peptide (hPTH1–34, dose 1.25 ug/kg/h in saline/0.1% bovine serum albumin, Bachem, Calif.) or a mixture of hPTH1–34 and test material, by continuous intravenous infusion via the venous catheter using an external syringe pump. The calcemic response of each rat is measured at two-hourly intervals during the infusion period of 6–8 hours.

Human Osteoclast Resorption and Adhesion Assays

Pit resorption and adhesion assays have been developed and standardized using normal human osteoclasts derived from osteoclastoma tissue. Assay 1 was developed for the measurement of osteoclast pit volumes by laser confocal microscopy. Assay 2 was developed as a higher throughput screen in which collagen fragments (released during resorption) are measured by competitve ELISA.

Assay 1 (Using Laser Confocal Microscopy)

Aliquots of human osteoclastoma-derived cell suspensions are removed from liquid nitrogen strorage, warmed rapidly at 37° C. and washed x1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed x2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated x10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

3 ml aliquots of the cell suspension (per compound treatment) are decanted into 15 ml centrifuge tubes. The cells are pelleted by centrifugation.

To each tube, 3 ml of the appropriate compound treatment are added (diluted to 50 uM in the EMEM medium). Also included are appropriate vehicle controls, a positive control (anti-vitronectin receptor murine monoclonal antibody [87MEM1] diluted to 100 ug/ml) and an isotype control ($IgG_{2a}$ diluted to 100 ug/ml). The samples are incubated at 37° C. for 30 mins.

0.5 ml aliquots of the cells are seeded onto sterile dentine slices in a 48-well plate and incubated at 37° C. for 2 hours. Each treatment is screened in quadruplicate.

The slices are washed in six changes of warm PBS (10 ml/well in a 6-well plate) and then placed into fresh medium containing the compound treatment or control samples. The samples are incubated at 37° C. for 48 hours.

Tartrate Resistant Acid Phosphatase (TRAP) Procedure (Selective Stain for Cells of the Osteoclast Lineage)

The bone slices containing the attached osteoclasts are washed in phosphate buffered saline and fixed in 2% gluteraldehyde (in 0.2M sodium cacodylate) for 5 mins.

They are then washed in water and are incubated for 4 minutes in TRAP buffer at 37° C. (0.5 mg/ml naphthol AS-BI phosphate dissolved in N,N-dimethylformamide and mixed with 0.25 M citrate buffer (pH 4.5), containing 10 mM sodium tartrate.

Following a wash in cold water the slices are immersed in cold acetate buffer (0.1 M, pH 6.2) containing 1 mg/ml fast red garnet and incubated at 4° C. for 4 minutes.

Excess buffer is aspirated, and the slices are air dried following a wash in water.

The TRAP positive osteoclasts (brick red/purple precipitate) are enumerated by bright-field microscopy and are then removed from the surface of the dentine by sonication.

Pit volumes are determined using the Nikon/Lasertec ILM21W confocal microscope.

Assay 2 (Using an ELISA Readout)

The human osteoclasts are enriched and prepared for compound screening as described in the initial 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

In contrast to the method desribed above in Assay 1, the compounds are screened at 4 doses to obtain an $IC_{50}$, as outlined below:

The osteoclast preparations are preincubated for 30 minutes at 37° C. with test compound (4 doses) or controls.

They are then seeded onto bovine cortical bone slices in wells of a 48-well tissue culture plate and are incubated for a further 2 hours at 37° C.

The bone slices are washed in six changes of warm phosphate buffered saline (PBS), to remove non-adherent cells, and are then returned to wells of a 48 well plate containing fresh compound or controls.

The tissue culture plate is then incubated for 48 hours at 37° C.

The supernatants from each well are aspirated into individual tubes and are screened in a competitive ELISA that detects the c-telopeptide of type I collagen which is released during the resorption process. This is a commercially available ELISA (Osteometer, Denmark) that contains a rabbit antibody that specifically reacts with an 8-amino acid sequence (Glu-Lys-Ala-His-Asp-Gly-Gly-Arg) that is present in the carboxy-terminal telopeptide of the α1-chain of type I collagen. The results are expressed as % inhibition of resorption compared to a vehicle control, Human Osteoclast Adhesion Assay The human osteoclasts are enriched and prepared for compound screening as described above in the inital 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteociasts is variable from tumor to tumor), supplemented with 10% fetal calf serum and 1.7 g/liter of sodium bicarbonate.

Osteoclastoma-derived osteoclasts are preincubated with compound (4 doses) or controls at 37° C. for 30 minutes.

The cells are then seeded onto osteopontin-coated slides (human or rat osteopontin, 2.5 ug/ml) and incubated for 2 hours at 37° C.

Non adherent cells are removed by washing the slides vigorously in phosphate buffered saline and the cells remaining on the slides are fixed in acetone.

The osteoclasts are stained for tartrate-resistant acid phosphatase (TRAP), a selective marker for cells of this phenotype (see steps 15–17), and are enumerated by light microscopy. The results are expressed as % inhibition of adhesion compared to a vehicle control.

Cell Adhesion Assay

Cells and Cell Culture

Human embryonic kidney cells (HEK293 cells) were obtained from ATCC (Catalog No. CRL 1573). Cells were grown in Earl's minimal essential medium (EMEM) medium containing Earl's salts, 10% fetal bovine serum, 1% glutamine and 1% Penicillin-Steptomycin.

Constructs and Transfections

A 3.2 kb EcoRI-KpnI fragment of the $\alpha_v$ subunit and a 2.4 kb XbaI-XhoI fragment of the $\beta_3$ subunit were inserted into the EcoRI-EcoRV cloning sites of the pCDN vector (Aiyar et al., 1994) which contains a CMV promoter and a G418 selectable marker by blunt end ligation. For stable expression, 80×10⁶ HEK 293 cells were electrotransformed with $\alpha_v+\beta_3$ constructs (20 μg DNA of each subunit) using a Gene Pulser (Hensley et al., 1994) and plated in 100 mm plates (5×10⁵ cells/plate). After 48 hr, the growth medium was supplemented with 450 μg/mL Geneticin (G418 Sulfate, GIBCO-BRL, Bethesda, Md.). The cells were maintained in selection medium until the colonies were large enough to be assayed.

Immunocytochemical Analysis of Transfected Cells

To determine whether the HEK 293 transfectants expressed the vitronectin receptor, the cells were immobilized on glass microscope slides by centrifugation, fixed in acetone for 2 min at room temperature and air dried. Specific reactivity with 23C6, a monoclonal antibody specific for the $\alpha_v\beta_3$ complex was demonstrated using a standard indirect immunofluorescence method.

Cell Adhesion Studies

Corning 96-well ELISA plates were precoated overnight at 4° C. with 0.1 mL of human vitronectin (0.2 µg/mL in RPMI medium). At the time of the experiment, the plates were washed once with RPMI medium and blocked with 3.5% BSA in RPMI medium for 1 hr at room temperature. Transfected 293 cells were resuspended in RPMI medium, supplemented with 20 mM Hepes, pH 7.4 and 0.1% BSA at a density of $0.5 \times 10^6$ cells/mL. 0.1 mL of cell suspension was added to each well and incubated for 1 hr at 37° C. in the presence or absence of various $\alpha_v\beta_3$ antagonists. Following incubation, 0.025 mL of a 10% formaldehyde solution, pH 7.4. was added and the cells were fixed at room temperature for 10 min. The plates were washed 3 times with 0.2 mL of RPMI medium and the adherent cells were stained with 0.1 mL of 0.5% toluidine blue for 20 min at room temperature. Excess stain was removed by extensive washing with deionized water. The toluidine blue incorporated into cells was eluted by the addition of 0.1 mL of 50% ethanol containing 50 mM HCl. Cell adhesion was quantitated at an optical density of 600 nm on a microtiter plate reader (Titertek Multiskan MC, Sterling, Va.).

Solid-phase $\alpha_v\beta_5$ Binding Assay:

The vitronectin receptor $\alpha_v\beta_5$ was purified from human placenta. Receptor preparation was diluted with 50 mM Tris-HCl, pH 7.5, 100 mM NaCl, 1 mM $CaCl_2$, 1 mM $MnCl_2$, 1 mM $MgCl_2$ (buffer A) and was immediately added to 96-well ELISA plates at 0.1 ml per well. 0.1–0.2 µg of $\alpha_v\beta_3$ was added per well. The plates were incubated overnight at 4° C. At the time of the experiment, the wells were washed once with buffer A and were incubated with 0.1 ml of 3.5% bovine serum albumin in the same buffer for 1 hr at room temperature. Following incubation the wells were aspirated completely and washed twice with 0.2 ml buffer A.

In a [$^3$H]-SK&F-107260 competition assay, various concentrations of unlabeled antagonists (0.001–100 µM) were added to the wells, followed by the addition of 5.0 nM of [$^3$H]-SK&F-107260. The plates were incubated for 1 hr at room temperature. Following incubation the wells were aspirated completely and washed once with 0.2 ml of ice cold buffer A in a well-to-well fashion The receptors were solubilized with 0.1 ml of 1% SDS and the bound [$^3$H]-SK&F-107260 was determined by liquid scintillation counting with the addition of 3 ml Ready Safe in a Beckman LS 6800 Liquid Scintillation Counter, with 40% efficiency. Nonspecific binding of [$^3$H]-SK&F-107260 was determined in the presence of 2 µM SK&F-107260 and was consistently less than 1% of total radioligand input. The $IC_{50}$ (concentration of the antagonist to inhibit 50% binding of [$^3$H]-SK&F-107260) was determined by a nonlinear, least squares curve-fitting routine, which was modified from the LUNDON-2 program. The $K_i$ (dissociation constant of the antagonist) was calculated according to Cheng and Prusoff equation: $K_i = IC_{50}/(1+L/K_d)$, where L and $K_d$ were the concentration and the dissociation constant of [$^3$H]-SK&F-107260, respectively.

Inhibition of RGD-Mediated GPIIb-IIIa Binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM $CaCl_2$ (with 2 changes). The GPIb-IIIa-containing liposomes wee centrifuged at 12,000 g for 15 min and resuspended in the dialysis buffer at a final protein concentration of approximately 1 mg/mL. The liposomes were stored at −70° C. until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 µg/mL polylysine (Sigma Chemical Co., St. Louis, Mo.) at room temperature for 1 h to block nonspecific binding. Various concentrations of unlabeled benzazepines were added to the wells in quadruplicate. [$^3$H]-SK&F-107260 was applied to each well at a final concentration of 4.5 nM, followed by the addition of 1 µg of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton. Calif.) in a Beckman Liquid Scintillation Counter (Model LS6800), with 40% efficiency. Nonspecific binding was determined in the presence of 2 µM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki=IC50/(1+L/Kd), where L is the concentration of [3H]-SK&F-107260 used in the competitive binding assay (4.5 nM), and Kd is the dissociation, constant of [3H]-SK&F-107260 which is 4.5 nM as determined by Scatchard analysis.

Preferred compounds of this invention have an affinity for the vitronectin receptor relative to the fibrinogen receptor of greater than 10:1. Most preferred compounds have a ratio of activity of greater than 100:1.

The efficacy of the compounds of formula (I) alone or in combination with an antineoplastic agent may be determined using several transplantable mouse tumor models. See U.S. Pat. Nos. 5,004,758 and 5,633,016 for details of these models The examples which follow are intended in no way to limit the scope of this invention, but are provided to illustrate how to make and use the compounds of this invention. Many other embodiments will be readily apparent to those skilled in the art.

EXAMPLES

General

Proton nuclear magnetic resonance ($^1$H NMR) spectra were recorded at either 250 or 400 MHz. Chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Infrared (IR) spectra were recorded in transmission mode, and band positions are reported in inverse wavenumbers (cm$^{-1}$). Mass spectra were obtained using electrospray (ES) or FAB ionization techniques. Elemental analyses were performed either in-house or by Quantitative Technologies Inc., Whitehouse, N.J. Melting points were taken on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5μ Apex-ODS indicates an octadecylsilyl derivatized silica gel chromatographic support having a nominal particle size of 5μ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Ethyl (±)-10,11-dihydro-3-methoxy-5H-dibenzo[a,d]cycloheptene-10-acetate, ethyl (±)-10,11-dihydro-3-hydroxy-5H-dibenzo[a,d]cycloheptene-10-acetate, and ethyl (±)-10,11-dihydro-3-(trifluoromethanesulfonyloxy)-5H-dibenzo[ad]cycloheptene-10-acetate were prepared according to WO 9701540-A1. 2-[2-(4-Methoxybenzylamino)pyridin-6-yl]ethanol was prepared according to WO 95/32710. 6-Methoxy-1-indanone was prepared by the method of House and Hudson (*J. Org. Chem.* 1970, 35, 647).

Preparation 1

Preparation of 2-[(3-hydroxy-1-propyl)amino]pyridine-N-oxide a) 2-[(3-Hydroxy-1-propyl)amino]pyridine-N-oxide A mixture of 2-chloropyridine-N-oxide hydrochloride (16.6 g, 0.1 mole), 3-amino-1-propanol (15.3 mL, 0.2 mole), NaHCO$_3$ (42 g, 0.5 mole), and tert-amyl alcohol (100 mL) was heated to reflux. After 21 hr, the reaction was cooled, diluted with CH$_2$Cl$_2$ (300 mL), and suction filtered to remove insoluble materials. The filtrate was concentrated and reconcentrated from toluene to leave a yellow oil. Silica gel chromatography (20% MeOH/CHCl$_3$) gave the title compound (15.62 g, 93%) as a yellow solid: TLC (20% MeOH/CHCl$_3$) R$_f$0.48; $^1$H NMR (250, CDCl$_3$) δ8.07 (dd, J=6.6, 1.2 Hz, 1 H), 7.34 (br t, 1 H), 7.10–7.30 (m, 1 H), 6.64 (dd, J=8.5, 1.4 Hz, 1 H), 6.40–6.60 (m, 1 H), 4.49 (br s, 1 H), 3.65–3.90 (m, 2 H), 3.35–3.60 (m, 2 H), 1.75–2.00 (m, 2 H); MS (ES) m/e 169 (M+H)$^+$.

Preparation 2

Preparation of 2-[(3-hydroxy-1-propyl)amino]-4-nitropyridine-N-oxide a) 2-Chloro-4-nitropyridine-N-oxide A solution of conc. H$_2$SO$_4$ (30 mL) and fuming HNO$_3$ (54 mL) was added dropwise at 0° C. to a solution of 2-chloropyridine-N-oxide hydrochloride (15.2 g, 91.56 mmole) in conc. H$_2$SO$_4$ (30 mL). The reaction mixture was heated at 90° C. for 1 hr, then was cooled to RT and poured onto ice (500 g). The reaction mixture was kept at RT overnight, then was cooled in an ice bath, and 50% NaOH was added slowly to give a precipitate. This was collected and dried to give the title compound (5.88 g, 37%) as a pale yellow solid: $^1$H NMR (400 MHz, CDCl$_3$) δ8.42-8.37 (m, 2 H), 8.06-8.04 (m, 1 H).

a) 2-[(3-Hydroxy-1-propyl)amino]-4-nitropyndine-N-oxide

According to the procedure of Preparation 1, except substituting 2-chloro-4-nitropyridine-N-oxide for the 2-chloropyridine-N-oxide hydrochloride, the title compound was obtained as yellow powder following silica gel chromatography (1:9 MeOH/CH$_2$Cl$_2$). Recrystallization from MeOH/CH$_2$Cl$_2$/Et$_2$O gave the title compound: MS (ES) 214.1 (M+H)$^+$.

Preparation 3

Preparation of 2-[(3-hydroxy-1-propyl)amino]-4-methylpyridine-N-oxide a) 2-Chloro-4-methylpyridine Sodium nitrite (13.88 g, 200 mmole) was added slowly at 0° C. to a solution of 2-amino-4-picoline (15.0 g, 139 mmole) in conc. HCl (200 mL). The reaction mixture was allowed to warm to RT and was stirred for 16 hr, then was poured onto ice (500 g). The pH was adjusted to 8.0 with conc. NH$_4$OH, and the mixture was extracted with ether (3×300 mL). The combined ether layers were washed sequentially with H$_2$O (2×200 mL) and brine (200 mL). Drying (MgSO$_4$) and concentration gave the title compound (10.3 g, 58%) as a faintly yellow oil: MS (ES) m/e 127.8 (M+H)$^+$.

b) 2-Chloro-4-methylpyridine-N-oxide hydrochloride

A mixture of 2-chloro-4-methylpyridine (10.0 g, 78.3 mmole) and 34% peracetic acid (76.05 g, 91.0 mmole) in glacial AcOH (10 mL) was heated at 70° C. for 3 hr. The reaction mixture was cooled, conc. HCl (35 mL) was added, and the mixture was concentrated on the rotavap. Recrystallization from n-butanol followed by trituration with ether gave the title compound (7.16 g, 51%) as a white solid: MS (ES) m/e 143.9 (M+H)+.

c) 2-[(3-Hydroxy-1-propyl)amino]-4-methylpyridine-N-oxide

A mixture of 2-chloro-4-methylpyridine-N-oxide hydrochloride (7.16 g, 39 mmole), 3-aminopropanol (6.01 g, 80 mmole), and NaHCO$_3$ (16.8 g, 200 mmole) in tert-amyl alcohol (50 mL) was heated at reflux for 19 hr. The reaction mixture was diluted with CH$_2$Cl$_2$ (200 mL) and filtered, and the filtrate was concentrated on the rotavap. Recrystallization from CH$_2$Cl$_2$/Et$_2$O gave the title compound (5.41 g, 75%) as a yellow solid: TLC (15% MeOH/CH$_2$Cl$_2$) $R_f$ 0.44; $^1$H NMR (400, CDCl$_3$) δ7.92 (d, J=6.7, 1 H), 7.28 (br t, 1 H), 6.43 (s, 1 H), 6.33 (dd, J=6.6, 2.1 Hz, 1 H), 3.73 (t, J=5.7 Hz, 2 H), 3.47 (q, H=6.3 Hz, 2 H), 2.29 (s, 3 H), 1.82–1.88 (m, 2 H); MS (ES) m/e 183 (M+H)+.

Preparation 4

Preparation of 6-(methylamino)-2-pyridylethanol a) 2-(tert-Butoxycarbonylamino)-6-picoline A solution of 2-amino-6-picoline (21.63 g, 200 mmole) and di-tert-butyl dicarbonate (52.38 g, 240 mmole) in CH$_2$Cl$_2$ (200 mL) was concentrated on the rotavap at 50° C., and the resulting residue was allowed to rotate on the rotavap at 50° C. under vacuum. After 21.5 hr, the reaction was diluted with hexanes (400 mL) and filtered through silica gel (hexanes followed by 20% EtOAc/hexanes). Concentration left the title compound (41.84 g, quantitative) as a light yellow oil which gradually solidified on standing: $^1$H NMR (250 MHz, CDCl$_3$) δ7.71 (d, J=8.3 Hz, 1 H), 7.40–7.65 (m, 2 H), 6.80 (d, J=7.5 Hz, 1 H), 2.43 (s, 3 H), 1.50 (s, 9 H); MS (ES) m/e 153 (M+H-C$_4$H$_8$)+.

b) 2-[(tert-Butoxycarbonyl)methylamino]-6-picoline

NaH (60% in mineral oil, 3.60 g, 90 mmole) was added in portions over several min to a solution of 2-(tert-butoxycarbonylamino)-6-picoline (15.62 g, 75 mmole) and iodomethane (9.3 mL, 150 mmole) in anhydrous DMSO (75 mL) at 15° C. (cool water bath). The internal temperature rose to 35° C. When gas evolution had subsided, the cool water bath was removed and the reaction was allowed to stir at RT. After 0.5 hr, the dark yellow mixture was poured onto ice/H$_2$O (300 mL) and extracted with Et$_2$O (3×300 mL). The combined organic layers were washed sequentially with H$_2$O (2×75 mL) and brine (75 mL). Drying (MgSO$_4$) and concentration left a yellow oil which was chromatographed on silica gel (7% EtOAc/hexanes). The title compound (13.01 g, 78%) was obtained as a faintly yellow oil: $^1$H NMR (250 MHz, CDCl$_3$) δ7.51 (app t, 1 H), 7.37 (d, J=8.2 Hz, 1 H), 6.86 (d, J=7.2 Hz, 1 H), 3.38 (s, 3 H), 2.49 (s, 3 H), 1.50 (s, 9 H); MS (ES) m/e 223 (M+H)+.

c) Ethyl-6-[(tert-butoxycarbonyl)methylamino]-2-pyridylacetate

LDA was prepared at 0° C. under argon from diisopropylamine (19.5 mL, 139.14 mmole) and 2.5 M n-BuLi in hexanes (46.4 mL, 115.95 mmole) in dry THF (350 mL). This solution was cooled to −78° C. and a solution of 2-[(tert-butoxycarbonyl)methylamino]-6-picoline (10.31 g, 46.38 mmole) in dry THF (46 mL) was added dropwise over 10 min. Additional dry THF (2 mL) was used in transfer. The orange solution was stirred at −78° C. for 15 min, then diethyl carbonate (6.2 mL, 51.02 mmole) was added rapidly. The red solution was stirred at −78° C. for 15 min, then was quenched with half-saturated NH$_4$Cl (175 mL). The mixture was warmed to +5° C. and extracted with EtOAc (175 mL) then with CH$_2$Cl$_2$ (2×100 mL). The combined organics were washed with brine (100 mL), dried (MgSO$_4$), and concentrated. The cloudy yellow oil was chromatographed on silica gel (15% EtOAc/hexanes) to afford the title compound (10.72 g, 79%) as a light yellow oil: $^1$H NMR (250 MHz, CDCl$_3$) δ7.51–7.63 (m, 2 H), 6.91–7.03 (m, 1 H), 4.19 (q, J=7.1 Hz, 2 H), 3.77 (s, 2 H), 3.38 (s, 3 H), 1.27 (t, J=7.1 Hz, 3 H), 1.51 (s, 9 H); MS (ES) m/e 295 (M+H)+.

d) Ethyl-6-(methylamino)-2-pyridylacetate

A solution of ethyl-6-[(tert-butoxycarbonyl)methylamino]-2-pyridylacetate (10.72 g, 36.42 mmole) in anhydrous dioxane (91 mL) was cooled to the point of partial crystallization of the solvent, and 4 M HCl/dioxane (91 mL, 364.2 mmole) was added. The solution was warmed to RT and stirred for 17 hr, then was concentrated. The resulting light yellow solid was slurried with CH$_2$Cl$_2$/toluene and reconcentrated to leave the title compound (8.48 g, quantitative) as a light yellow powder: $^1$H NMR (250 MHz, CD$_3$OD) δ7.84 (dd, J=9.0, 7.2 Hz, 1 H), 6.96 (d, J=9.0 Hz, 1 H), 6.78 (d, J=7.2 Hz, 1 H), 4.22 (q, J=7.1 Hz, 2 H), 3.93 (s, 2 H), 3.05 (s, 3 H), 1.27 (t, J=7.1 Hz, 3 H); MS (ES) m/e 195 (M+H)+.

e) 6-(Methylamino)-2-pyridylethanol

A solution of 1.0 M LiAlH$_4$ in THF (95 mL, 95 mmole) was added dropwise to a mechanically stirred suspension of ethyl-2-(methylamino)-6-pyridylacetate (7.34 g, 31.82 mmole) in dry THF (64 mL) at 0° C. under argon. The addition was done slowly until gas evolution subsided, then the remaining solution was added rapidly. Addition required 5–7 min. The reaction was warmed to RT and stirred for 45 min, then was heated to reflux. After 10 min, the reaction was cooled to 0° C. and worked up by sequential dropwise addition of H$_2$O (3.6 mL), 15% NaOH (3.6 mL), and H$_2$O (10.8 mL). The mixture was stirred for 15 min at 0° C. and 15 min at RT, then was filtered through a Buchner funnel. The filter pad was washed with plenty of THF, and the filtrate was concentrated. The residue was reconcentrated from toluene, then was chromatographed on silica gel (5% MeOH in 1:1 EtOAc/CHCl$_3$) to afford the title compound (3.23 g, 67%) as a yellow oil which solidified to a waxy solid: $^1$H NMR (250 MHz, CDCl$_3$) δ7.36 (dd, J=8.3, 7.3 Hz, 1 H), 6.42 (d, J=7.3 Hz, 1 H), 6.26 (d, J=8.3 Hz, 1 H), 4.93–5.28 (m, 1 H), 4.38–4.60 (m, 1 H), 3.96 (t, J=5.4 Hz, 2 H), 2.90 (d, J=5.2 Hz, 3 H), 2.84 (t, J=5.4 Hz, 2 H); MS (ES) m/e 153 (M+H)+.

Preparation 5

Preparation of 2-(ethylamino)-4-thiazoleethanol a) Ethyl 2-acetylamino-4-thiazoleacetate Ethyl 2-amino-4-thiazoleacetate (3.72 g 20 mmole) was taken up in acetic acid (4 mL) and acetic anhydride (4 mL), and the resulting suspension was heated at reflux for 3 hr. Concentration and flash chromatography on silica gel (5% MeOH/CH$_2$H$_2$) gave the title compound (4.1 g, 91%) as a white solid: MS (ES) m/e 229 (M+H)+.

b) 2-(Ethylamino)-4-thiazoleethanol

To a stirred solution of 1.0 M LiAlH$_4$ in THF (179 mL, 179 mmole) was added dropwise a solution of ethyl 2-acetylamino-4-thiazoleacetate (4.4 g, 17.9 mmole) in THF (50 mL). After complete addition, the reaction mixture was heated at reflux for 3 hr, then was worked up by sequential addition of $H_2O$ (0.7 mL), 10% NaOH (0.7 mL), and $H_2O$ (2.1 mL). The resulting mixture was filtered through celite® and the filtrate was concentrated. Purification by flash chromatography on silica gel (5% $MeOH/CH_2H_2$) gave the title compound (1.6 g, 53%) as an amber oil: MS (ES) m/e 173 $(M+H)^+$.

Preparation 6

Preparation of 6-amino-2-pyridylethanol a) 6-Amino-2-pyridylethanol

A solution of 2-[2-(4-methoxybenzylamino)pyridin-6-yl]ethanol (0.95 g, 3.7 mmole), prepared according to the procedure of WO 95/32710, in 6 N HCl was heated at 60° C. After 16 hr, the reaction was concentrated in vacuum and the residue was made basic with dry KOH. The resulting mixture was extracted with MeOH, and the MeOH extracts were dried ($MgSO_4$) and concentrated. Flash chromatography on silica gel (5% $MeOH/CH_2H_2$) gave the title compound (0.2 g, 40%) as a pale yellow oil: MS (ES) m/e 139 $(M+H)^+$.

Preparation 7

Preparation of 3-(4-nitrobenizyloxycarbonylamino)-1-propanol a) 3-(4-Nitrobenzyloxycarbonyl)amino-1-propanol To a suspension stirred under argon at room temperature of 4-nitrobenzyl chloroformate (5 g, 23 mmol) and triethylamine (6.4 mL, 46 mmol) in THF (25 mL) was added 3-amino-1-propanol (1.9 mL, 26 mmol). The resulting mixture was stirred for 72 hr. then was concentrated. The residue was purified by chromatography on silica gel (0.5–2% $MeOH/CH_2Cl_2$) to give the title compound (2 g, 34%) as a pale yellow oil: MS (ES) 255.3 $(M+H)^+$.

Preparation 8

Preparation of 1-[(3-hydroxy-1-propyl)amino]isoquinoline-N-oxide a) 1-Chloroisoquinoline N-oxide 1-Aminoisoquinoline N-oxide hydrochloride (Deady, L. W. *Synthetic Communications* 1977, 509–514) was converted to 1-chloroisoquinoline N-oxide using potassium nitrite and conc. HCl according to the general method described in the literature (Brown. E. V. *J. Amer. Chem. Soc.* 1957, 79, 3565–3566). The title compound was prepared as a light brown solid: MS (ES) m/e 179.9 $(M+H)^+$.

b) 1-[(3-Hydroxy-1-propyl)amino]-isoquinoline N-oxide

According to the procedure of Preparation 1(a), except substituting 1-chloroisoquinoline N-oxide for the 2-chloropyridine-N-oxide hydrochloride, the title compound was prepared as an amber solid MS (ES) m/e 219.1 $(M+H)^+$.

Preparation 9

Preparation of 2-[N-(3-methanesulfonyloxy-1-propyl)-N-(tert-butoxycarbonyl)amino]pyridine-N-oxide a) 2-[N-(3-Hydroxy-1-propyl)-N-(tert-butoxycarbonyl)amino]pyridine-N-oxide A solution of 2-[(3-hydroxy-1-propyl)amino]pyridine-N-oxide (8.0 g, 47.6 mmol) in tert-BuOH (80 mL) was treated with di-tert-butyl dicarbonate (11.4 g, 55.3 mmol). After 18 h, the solution was concentrated and the residue was triturated with hexane. The resulting solid was dried in vacuo to give the title compound (12.5 g, 98%) as an off-white solid: MS (ES) m/e 269.3 $(M+H)^+$.

b) 2-[N-(3-Methanesulfonyloxy-1-propyl)-N-(tert-butoxycarbonyl)amino]pyridine-N-oxide Methanesulfonyl chloride (0.17 mL, 2.20 mmole) was added dropwise to a solution of 2-[N-(3-hydroxy-1-propyl)-N-(tert-butoxycarbonyl)amino]pyridine-N-oxide (0.50 g, 1.86 mmole) and pyridine (0.23 mL, 2.84 mmole) in $CHCl_3$ (5 mL, dried over $K_2CO_3$) at 0° C. When complete by TLC, the reaction was diluted with $CHCl_3$, washed with ice water, dried ($Na_2SO_4$), and concentrated. Silica gel chromatography (10% $MeOH/CHCl_3$) gave the title compound (0.41 g, 64%) as a colorless oil: $^1H$ NMR (250 MHz, $CDCl_3$) δ8.25 (dd, J=6.0, 1.9 Hz, 1 H), 7.25 (m, 4 H), 4.35 (t, J=6.2 Hz, 2 H), 3.75 (t, J=6.6 Hz, 2 H), 3.00 (s, 3 H), 2.00 (m, 2 H), 1.40 (s, 9 H). Unchanged 2-[N-(3-hydroxy-1-propyl)-N-(tert-butoxycarbonyl)amino]pyridine-N-oxide (0.18 g, 36%) could also be recovered from the chromatographic purification.

Preparation 10

Preparation of ethyl (±)-10,11-dihydro-3-hydroxy-5H-dibenzo[a,d]cycloheptene-10-acetate a) 6-Methoxy-1-phenylindene A solution of 3.0 M phenylmagnesium bromide in $Et_2O$ (680 mL, 2.04 mole) under argon at ambient temperature was diluted with $Et_2O$ (700 mL) with stirring, and a solution of 6-methoxy-1-indanone (277 g, 1.71 mole) in THF (1400 mL) was added dropwise over 1 hr. The reaction mixture was stirred for 2 h at ambient temperature and then was poured with stirring into saturated $NH_4Cl$ (2.8 L). $H_2O$ (1.4 L) was added, and the organic phase separated. The aqueous phase was extracted with $Et_2O$ (2×1 L), and the combined organic extracts were concentrated to give crude 6-methoxy-1-phenyl-1-indanol (445 g) as a brown oil. This oil was dissolved in toluene (2.5 L), and p-toluenesulfonic acid monohydrate (12.3 g, 0.065 mole) was added. The solution was stirred and heated at reflux for 16 hr using a Dean-Stark trap with a condenser. $H_2O$ collection was minimal after 2 h and totaled 28 mL. The solution was cooled and extracted sequentially with 5% aqueous $Na_2CO_3$ (1 L) and $H_2O$ (2×1 L). The organic layer was concentrated to give a dark brown oil (400 g). This oil was distilled under vacuum to give the title compound (298.2 g. 79%) as a yellow oil: bp 152–190° C./2.0 Torr; TLC (10% EtOAc/hexanes) $R_f$0.75.

b) 2-Benzoyl-4-methoxyphenylacetic acid

Acetone (4.2 L) was chilled to 10° C., and a solution of 6-methoxy-1-phenylindene (271 g, 1.22 mole) in acetone (1.8 L) was added over 1.5 hr concurrently with Jones reagent (1.8 L, prepared from $CrO_3$ (470 g, 4.70 mole), $H_2O$ (1 L), and conc $H_2SO_4$ (405 mL)). 4% Aqueous $OsO_4$ (153 mL) was added to the resulting mixture in two portions, one at the onset of addition and the second at the mid-point of the addition, maintaining the temperature of the reaction mixture below 15° C. Following the addition, the reaction mixture was warmed to 22° C. and stirred for 1.5 h, during which time a mild exotherm increased the temperature to 28° C. The reaction mixture was then cooled to below 20° C. and isopropanol (1 L) was added, dropwise initially and rapidly after the initial exotherm diminished. Stirring became difficult during this phase. The temperature reached 32° C. during the isopropanol addition. $H_2O$ (2 L) was added and the mixture was transferred to a separatory funnel. Additional $H_2O$ was added to dissolve the precipitated chromous acid, and the mixture was extracted with $CH_2Cl_2$ (2 L). The organic (upper) layer was separated and the aqueous phase was extracted with $CH_2Cl_2$ (2×1 L). The combined $CH_2Cl_2$ extracts were washed sequentially with $H_2O$ (2 L) and saturated brine (2 L), and then were concentrated to give a moist gray solid (416 g). This was triturated with a mixture of acetone and EtOAc and filtered and dried to give the title compound (225.4 g, 71%) as an off-white solid: mp 158–159° C.

c) 2-Benzyl-4-methoxyphenylacetic acid

2-Benzoyl-4-methoxyphenylacetic acid (215.5 g, 0.80 mole) was divided into two equal portions, and each was dissolved in glacial AcOH (1.5 L) in a 2.5 L pressure bottle. 5% Pd/C (10 g, 0.0048 mole) was added to each, and each mixture was shaken at ambient temperature under hydrogen on a Parr apparatus. After 2.5 hr, the mixtures were filtered to remove the catalyst, and the filter pads were washed with EtOAc. The combined filtrates were concentrated to give the title compound (215 g, quantitative) as a heavy yellow oil which crystallized on standing: $^1$H NMR (250 MHz, $CDCl_3$) δ7.05–7.35 (m, 6 H), 6.77 (dd, J=8.3, 2.7 Hz, 1 H), 6.71 (d, J=2.7 Hz, 1 H), 4.00 (s, 2 H), 3.76 (s, 3 H), 3.54 (s, 2 H).

d) 10,11-Dihydro-3-methoxy-5H-dibenzo[a,d]cyclohepten-10-one

A solution of 2-benzyl-4-methoxyphenylacetic acid (215 g of crude material that contained 204.6 g (0.80 mole) of pure material) in $CH_2Cl_2$ (1 L) was stirred under argon at ambient temperature, and DMF (1 mL) was added, followed by oxalyl chloride (400 mL, 4.59 mole). The oxalyl chloride was added over 1 hr, dropwise initially to control the vigorous gas evolution. The solution was stirred for 16 h at ambient temperature and then was concentrated to give the crude acid chloride (207.7 g, 0.756 mol, 95%) as a yellow liquid. This liquid was dissolved in $CH_2Cl_2$ to a total volume of 500 mL, and the solution and $AlCl_3$ (100.8 g, 0.756 mol) were added concurrently over 1 hr to $CH_2Cl_2$ (3.7 L) with stirring under argon at ambient temperature. The temperature was 28° C. at the completion of the addition. The reaction mixture was stirred for 16 h at ambient temperature, during which time a solid precipitated. $H_2O$ (1 L) was added, initially dropwise, over a period of 30 min. The mixture was then separated and the organic phase was washed sequentially with $H_2O$ (1 L) and 5% aqueous $NaHCO_3$ (1 L). The $CH_2Cl_2$ solution was then concentrated to give a yellow solid (175.3 g). Recrystallization from EtOAc/hexane gave the title compound (128 g, 71%): mp 107–109° C.

e) Ethyl (±)-10,11-dihydro-10-hydroxy-3-methoxy-5H-dibenzo[a,d]cycloheptene-10-acetate A 1.0 M solution of lithium bis(trimethylsilyl)amide in hexanes (1282 mL, 1.282 mole) was added to THF (4.0 L) at −70° C. under argon, then EtOAc (146 mL, 1.49 mole) was added dropwise over 20 min. The reaction mixture was allowed to stir for 15 min, then N,N,N',N'-tetramethylethlylenediamine (378 mL, 2.5 mole) was added over 20 min. The reaction mixture was stirred for 10 min, then a solution of 10,11-dihydro-3-methoxy-5H-dibenzo[a,d]cyclohepten-10-one (119.2 g, 0.50 mol) in anhydrous THF (1.26 L) was added dropwise over 40 min. The temperature was maintained below −65° C. during all of these additions. The reaction mixture was stirred for 20 min at −65 to −70° C. and then was poured into saturated aqueous $NH_4Cl$ (6.2 L) with vigorous stirring. The organic layer was separated and the aqueous phase was extracted with EtOAc (2×1 L). The combined organic extracts were washed with $H_2O$ (2×1 L) and then were concentrated to give a light brown oil (175 g). Thin-layer chromatography (20% EtOAc/hexanes) showed $R_f$0.5 major (desired product) and $R_f$0.7 minor (recovered ketone). The crude product was chromatographed on silica gel (2 kg, 10% EtOAc/hexanes) to afford the title compound (101 g, 61%) as a yellow oil: $^1$H NMR (250 MHz, $CDCl_3$) δ7.63 (d, J=7.7 Hz, 1 H), 7.00–7.30 (m, 4 H), 6.80 (d, J=2.6 Hz, 1 H), 6.69 (dd, J=8.2, 2.6 Hz, 1 H), 3.95–4.35 (m, 2 H), 4.07 (s, 2 H), 3.76 (s, 3 H), 3.68 (s, 1 H), 3.64 (d, J=14.2 Hz, 1 H), 3.35 (d, J=14.2 Hz, 1 H), 2.79 (d, J=16.0 Hz, 1 H), 2.66 (d, J=16.0 Hz, 1 H), 1.22 (t, J=7.2 Hz, 3 H).

f) Ethyl (±)-10,11-dihydro-3-methoxy-5H-dibenzo[a,d]cycloheptene-10-acetate

Ethyl (±)-10,11-dihydro-10-hydroxy-3-methoxy-5H-dibenzo[a,d]cycloheptene-10-acetate (101 g, 0.31 mole) was dissolved in glacial acetic acid (1.8 L) and 12 N HCl (28.5 mL, 0.34 mole) was added. The mixture was placed in a 2.5 L pressure bottle containing 5% Pd/C (20 g, 0.0094 mole), and the resulting mixture was shaken at 35° C. under hydrogen on a Parr hydrogenation apparatus equipped with a jacket heater. After 18 hr, the reaction was cooled to ambient temperature, and the catalyst was removed by filtration. The filtrate was concentrated to give a light yellow oil (85.1 g). This was chromatographed on silica gel (2 kg, step-gradient with 5% to 10% EtOAc/hexanes) to afford the title compound (69.1 g, 72%) as an oil: $^1$H NMR (250 MHz, $CDCl_3$) δ7.05–7.22 (m, 4 H), 7.01 (d, J=8.2 Hz, 1 H), 6.76 (d, J=2.7 Hz, 1 H), 6.67 (dd, J=8.2, 2.7 Hz, 1 H), 4.30 (d, J=15.0 Hz, 1 H), 4.11–4.25 (m, 2 H), 3.85 (d, J=15.0 Hz, 1 H), 3.70–3.90 (m, 1 H), 3.77 (s, 3 H), 3.31 (dd, J=15.0, 4.1 Hz, 1 H), 2.93 (dd, J=15.0, 9.2 Hz, 1 H), 2.64 (dd, J=15.6, 5.0 Hz, 1 H), 2.52 (dd, J=15.6, 9.3 Hz, 1 H), 1.27 (t, J=7.1 Hz, 3 H).

g) Ethyl (±)-10,11-dihydro-3-hydroxy-5H-dibenzo[a,d]cycloheptene-10-acetate

A solution of ethyl (±)-10,11-dihydro-3-methoxy-5H-dibenzo[a,d]cycloheptene-10-acetate (8.5 g, 0.027 mole) in $CH_2Cl_2$ (150 mL) was chilled to −10° C. with stirring under argon. Ethanethiol (10.7 mL, 0.144 mole) was added, followed by $AlCl_3$ (20.6 g, 0.154 mole) in two portions over 15 min. An exotherm increased the temperature to 0° C. following the additions, and the temperature was then increased to 25° C. using a water bath. The reaction mixture was stirred at 25 to 30° C. for 2.25 hr, at which point it was poured into ice-$H_2O$. The organic layer was separated, methanol (100 mL) was added, and the mixture was extracted with $CH_2Cl_2$ (2×50 mL). The combined $CH_2Cl_2$ extracts were washed with $H_2O$ (250 mL) and then were concentrated to give a viscous oil (8.6 g). This was taken up in $Et_2O$ (150 mL) and the ether was boiled off while replacing it with hexane. The desired phenol first separated as an oil which crystallized on stirring at ambient temperature. Two crops of solid were collected to afford the title compound (7.1 g, 89%): mp 110–112° C.

Preparation 11

HPLC Separation of the Enantiomers of ethyl (±)-10,11-dihydro-3-hydroxy-5H-dibenzo[a,d]cycloheptene-10-acetate a) Ethyl(R)-(+)-10,11-dihydro-3-hydroxy-5H-dibenzo[a,d]cycloheptene-10-acetate and ethyl (S)-(−)-10,11-dihydro-3-hydroxy-5H-dibenzo[a,d]cycloheptene-10-acetate Ethyl (±)-10,11-dihydro-3-hydroxy-5H-dibenzo[a,d]cycloheptene-10-acetate was resolved into its enantiomers using the following conditions: Daicel Chiralcel OJ® column (21.2×250 mm), 20% ethanol in hexane mobile phase, 15 mL/min flow rate, uv detection at 254 nm, 140 mg injection; $t_R$ for ethyl (S)-(−)-10,11-dihydro-3-hydroxy-5H-dibenzo[a,d]cyclohexene-10-acetate=10.4 min.; $t_R$ for ethyl (R)-(+)-10,11-dihydro-3-hydroxy-5H-dibenzo[a,d]cyclohexene-10-acetate=13.1 min.

Preparation 12

Preparation of ethyl (±)-10,11-dihydro-7-fluoro-3-hydroxy-5H-dibenzo[a,d]cycloheptene-10-acetate a) 1-(3-Fluorophenyl)-6-methoxy-1-indanol

According to the procedure of Preparation 10(a), except substituting 3-fluorophenylmagnesium bromide for the phenylmagnesium bromide, the title compound was obtained as an amber oil: MS (ES) m/e 276.0 $(M+H)^+$.

b) 1-(3-Fluorophenyl)-6-methoxyindene

According to the procedure of Preparation 10(a), except substituting 1-(3-fluorophenyl)-6-methoxy-1-indanol for the 6-methoxy-1-phenyl-1-indanol, the title compound was obtained as a colorless oil following silica gel chromatography (4% EtOAc/hexanes): MS (ES) m/e 241.1 $(M+H)^+$.

c) 2-(3-Fluorobenzoyl)-4-methoxyphenylacetic acid

According to the procedure of Preparation 10(b), except substituting 2-(3-fluorophenyl)-6-methoxyindene for the 6-methoxy-1-phenylindene, the title compound was obtained as a white solid: MS (ES) m/e 289.2 $(M+H)^+$.

d) 2-(3-Fluorobenzyl)-4-methoxyphenylacetic acid

According to the procedure of Preparation 10(c), except substituting 2-(3-fluorobenzoyl)-4-methoxyphenylacetic acid for the 2-benzoyl-4-methoxyphenylacetic acid, the title compound was obtained as a colorless oil: MS (ES−) m/e 273.2 $(M-H)^-$.

e) 10,11-Dihydro-7-fluoro-3-methoxy-5H-dibenzo[a,d]cyclohepten-10-one

According to the procedure of Preparation 10(d), except substituting 2-(3-fluorobenzyl)-4-methoxyphenylacetic acid for the 2-benzyl-4-methoxyphenylacetic acid, the title compound was obtained as a white solid: Mp 129–130° C.; MS (ES) m/e 279.2 $(M+Na)^+$.

f) Ethyl (±)-10,11-dihydro-7-fluoro-10-hydroxy-3-methoxy-5H-dibenzo[a,d]cycloheptene-10-acetate According to the procedure of Preparation 10(e), except substituting 10,11-dihydro-7-fluoro-3-methoxy-5H-dibenzo[a,d]cyclohepten-10-one for the 10,11-dihydro-3-methoxy-5H-dibenzo[a,d]cyclohepten-10-one, the title compound was obtained following silica gel chromatography (8% EtOAc/hexanes): MS (ES) m/e 362.2 $(M+NH_4)^+$.

g) Ethyl (±)-10,11-dihydro-7-fluoro-3-methoxy-5H-dibenzo[a,d]cycloheptene-10-acetate According to the procedure of Preparation 10(f), except substituting ethyl (±)-10,11-dihydro-7-fluoro-10-hydroxy-3-methoxy-5H-dibenzo[a,d]cycloheptene-10-acetate for the ethyl (±)-10,11-dihydro-10-hydroxy-3-methoxy-5H-dibenzo[a,d]cycloheptene-10-acetate, the title compound was obtained as a colorless oil following silica gel, chromatography (10% EtOAc/hexanes): MS (ES) m/e 329.2 $(M+H)^+$.

h) Ethyl (±)-10,11-dihydro-7-fluoro-3-hydroxy-5H-dibenzo[a,d]cycloheptene-10-acetate According to the procedure of Preparation 10 (g), except substituting ethyl (±)-10,11-dihydro-7-fluoro3-methoxy-5H-dibenzo[a,d]cycloheptene-10-acetate for the ethyl (±)-10,11-dihydro-3-methoxy-5H-dibenzo[a,d]cycloheptene-10-acetate, the title compound was obtained as a white solid following silica gel chromatography (1% MeOH/$CH_2Cl_2$): MS (ES) m/e 315.0 $(M+H)^+$, 332.0 $(M+NH_4)^+$.

Preparation 13

Preparation of ethyl (±)-10,11-dihydro-2-(dimethylamino)methyl-7-fluoro-3-hydroxy-5H-dibenzo[a,d]cycloheptene-10-acetate a) Ethyl (±)-10,11-dihydro-2-(dimethylamino)methyl-7-fluoro-3-hydroxy-5H-dibenzo[a,d]cycloheptene-10-acetate To a solution of ethyl (±)-10,11-dihydro-7-fluoro-3-hydroxy-5H-dibenzo[a,d]cycloheptene-10-acetate (0.4 g, 1.33 mmol) in 95% ethanol containing 2 M dimethylamine in MeOH (1.0 mL) was added 37% aqueous formaldehyde solution (0.5 mL) at RT under argon. After 20 hr, the reaction was heated to reflux for 5 hr, then was concentrated on the rotavap. The residue was partitioned between $H_2O$ and $Et_2O$, and the layers were separated. The aqueous layer was extracted with $Et_2O$, and the combined organic layers were washed with brine, dried ($MgSO_4$), and concentrated on the rotavap to give the title compound (330 mg, 67%) as a colorless oil: $^1$H NMR (400 MHz, $CDCl_3$) δ7.20 (m, 1 H), 6.88 (m, 2 H), 6.67 (s, 2 H),4.25 (d, J=15.1 Hz, 1 H), 4.18 (q, 2 H), 3.78 (m, 1 H), 3.74 (d, J=15.1 Hz, 1 H), 3.55 (s, 2 H), 3.20 (dd, 1 H), 2.80 (dd, 1 H), 2.60 (dd, 1 H), 2.53 (dd, 1 H), 2.29 (S, 6 H), 1.27 (t, 3 H); MS(ES) m/e 372.3 $(M+H)^+$.

Preparation 14

Preparation of Ethyl (±)-10,11-dihydro-3-hydroxy-2-methyl-5H-dibenzo[a,d]cycloheptene-10-acetate a) Ethyl (±)-10,11-dihydro-2-formyl-3-methoxy-5H-dibenzo[a,d]cycloheptene-10-acetate $POCl_3$ (17 mL) was added dropwise to a solution of ethyl (±)-10,11-dihydro-3-methoxy-5H-dibenzo[a,d]cycloheptene-10-acetate (1.0 g, 3 mmol) in dry DMF (40 mL) at RT under argon, and the dark solution was heated at 90° C. for 48 hr. The reaction was concentrated on the rotavap and the residue was partitioned between $H_2O$ and EtOAc. The organic layer was separated, dried ($MgSO_4$), and concentrated on the rotavap. The residue was reconcentrated from xylenes (to remove any remaining DMF) then was chromatographed on silica gel (7% EtOAc in hexanes) to afford the title compound (230 mg, 21%) as a colorless oil: MS (ES) m/e 339.3 (M+H)+.

b) Ethyl (±)-10,11-dihydro-3-methoxy-2-methyl-5H-dibenzo[a,d]cycloheptene-10-acetate A mixture of ethyl (±)-10,11-dihydro-2-formyl-3-methoxy-5H-dibenzo[a,d]cycloheptene-10-acetate (220 mg, 0.65 mmol), 10% Pd/C (90 mg), glacial HOAc (15 mL), and conc HCl (2 mL) was shaken at RT under hydrogen (60 psi). After 20 hr, the mixture was filtered through celite®, and the filtrate was concentrated to afford the title compound (200 mg, 95%) as a colorless oil: MS (ES) m/e 325.2 (M+H)+.

c) Ethyl (±)-10,11-dihydro-3-hydroxy-2-methyl-5H-dibenzo[a,d]cycloheptene-10-acetate To dry $CH_2Cl_2$ (30 mL) cooled in an ice bath was added diethylsulfide (0.38 mL, 3.3 mmol) followed by $AlCl_3$ (438 mg, 3.3 mmol). To this solution was added dropwise a solution of ethyl (±)-10,11-dihydro-3-methoxy-2-methyl-5H-dibenzo[a,d]cycloheptene-10-acetate (200 mg, 0.6 mmole) in dry $CH_2Cl_2$ (6 mL), and the resulting mixture was stirred at RT for 2 hr. The reaction was quenched with 1.0 N HCl (10 mL), and the layers were separated. The organic layer was dried ($MgSO_4$) and concentrated on the rotavap to give the title compound (100 mg, 56%) as a colorless oil: MS (ES) m/e 311.2 (M+H)+.

Preparation 15

Preparation of Ethyl (±)-10,11-dihydro-3-hydroxy-6-methyl-5H-dibenzo[a,d]cycloheptene-10-acetate a) 6-Methoxy-1-(2-methylphenyl)-1-indanol According to the procedure of Preparation 10 (a), except substituting 2-methylphenylmagnesium bromide for the phenylmagnesium bromide, the title compound was obtained as an oil: MS (ES) m/e 277.0 (M+Na)+.

b) 6-Methoxy-1-(2-methylphenyl)indene

According to the procedure of Preparation 10 (a), except substituting 6-methoxy-1-(2-methylphenyl)-1-indanol for the 6-methoxy-1-phenyl-1-indanol, the title compound was obtained as a colorless oil following silica gel chromatography (3% EtOAc/hexanes): MS (ES) m/e 237.2 (M+H)+.

c) 4-Methoxy-2-(2-methylbenzoyl)phenylacetic Acid

According to the procedure of Preparation 10 (b), except substituting 6-methoxy-1-(2-methylphenyl)indene for the 6-methoxy-1-phenylindene, the title compound was obtained as a viscous oil: MS (ES) m/e 285.3 (M+NH₄)+.

d) 4-Methoxy-2-(2-methylbenzyl)phenylacetic Acid

According to the procedure of Preparation 10 (c), except substituting 4-methoxy-2-(2-methylbenzoyl)phenylacetic acid for the 2-benzoyl-4-methoxyphenylacetic acid, the title compound was obtained as a viscous oil: MS (ES) m/e 288.2 (M+NH₄)+.

e) 10,11-Dihydro-3-methoxy-6-methyl-5H-dibenzo[a,d]cyclohepten-10-one

According to the procedure of Preparation 10 (d), except substituting 4-methoxy-2-(2-methylbenzyl)phenylacetic acid for the 2-benzyl4-methoxyphenylacetic acid, the title compound was obtained as a white solid following silica gel chromatography (6% EtOAc/hexanes): MS (ES) m/e 253.0 (M+H)+.

f) Ethyl (±)-10,11-dihydro-10-hydroxy-3-methoxy-6-methyl-5H-dibenzo[a,d]cycloheptene-10-acetate According to the procedure of Preparation 10 (e), except substituting 10,11-dihydro-3-methoxy-6-methyl-5H-dibenzo[a,d]cyclohepten-10-one for the 10,11-dihydro-3-methoxy-5H-dibenzo[a,d]cyclohepten-10-one, the title compound was obtained following silica gel chromatography (8% EtOAc/hexanes): MS (ES) m/e 358.2 M+NH₄)+.

g) Ethyl (±)-10,11-dihydro-3-methoxy-6-methyl-5H-dibenzo[a,d]cycloheptene-10-acetate According to the procedure of Preparation 10 (f), except substituting ethyl (±)-10,11-dihydro-10-hydroxy-3-methoxy-6-methyl-5H-dibenzo[a,d]cycloheptene-10-acetate for the ethyl (±)-10,11-dihydro-10-hydroxy-3-methoxy-5H-dibenzo[a,d]cycloheptene-10-acetate, the title compound was obtained as a colorless oil following silica gel chromatography (5% EtOAc/hexanes): MS (ES) m/e 325.3 (M+H)+.

h) Ethyl (±)-10,11-dihydro-3-hydroxy-6-methyl-5H-dibenzo[a,d]cycloheptene-10-acetate According to the procedure of Preparation 10 (g), except substituting ethyl (±)-10,11-dihydro-3-methoxy-6-methyl-5H-dibenzo[a,d]cycloheptene-10-acetate for the ethyl (±)-10,11-dihydro-3-methoxy-5H-dibenzo[a,d]cycloheptene-10-acetate, the title compound was obtained as a white solid after trituration with MeOH: MS (ES) m/e 311.2 (M+H)+.

Preparation 16

Preparation of ethyl (±)-10,11-dihydro-3-[3-(4-nitro-1-oxopyridin-2-ylamino)-1-propyloxy]-5H-dibenzo[a,d]cycloheptene-10-acetate a) Ethyl (±)-10,11-dihydro-3-[3-(4-nitro-1-oxopyridin-2-ylamino)-1-propyloxy]-5 H-dibenzo[a, d]cycloheptene-10-acetate A solution of 2-[(3-hydroxy-1-propyl)amino]-4-nitropyridine-N-oxide (0.85 g, 4 mmole) and diethyl azodicarboxylate (0.63 mL, 4 mmole) in anhydrous DMF (10 mL) was added dropwise to a solution of ethyl (±)-10,11-dihydro-3-hydroxy-5H-dibenzo[a,d]cycloheptene-10-acetate (0.59 g, 2 mmole) and triphenylphosphine (1.10 g, 4.2 mmole) in anhydrous DMF (10 mL) at RT under argon. After 23 hr, the reaction was concentrated and the residue was reconcentrated from xylenes (2x). Silica gel chromatography (gradient: 1:1 EtOAc/hexanes, then EtOAc, then 5% MeOH in 1:1 EtOAc/CHCl₃) gave crude title compound. Unchanged (±)-10,11-dihydro-3-hydroxy-5H-dibenzo[a,d]cycloheptene-10-acetate could be recovered from the 1:1 EtOAc/hexanes fractions. Rechromatography of the crude title compound (3% MeOH in 1:1 EtOAc/CHCl₃) gave clean title compound (0.72 g, 73%) as a yellow foam: TLC (10% MeOH in 1:1 EtOAc/CHCl₃) $R_f$ 0.59; $^1$H NMR (250 MHz, CDCl₃) δ8.19 (d, J=7.1 Hz, 1 H), 7.46 (d, J=2.9 Hz, 1 H), 7.35 (dd, J=7.1, 2.9 Hz, 1 H), 7.00–7.30 (m, 5 H), 7.00 (d, J=8.2 Hz, 1 H), 6.81 (d, J=2.6 Hz, 1 H), 6.70 (dd, J=8.2, 2.6 Hz, 1 H), 4.29 (d, J=15.1 Hz, 1 H), 4.18 (q, J=7.1 Hz, 2 H), 4.08 (t, J=5.5 Hz, 2 H), 3.86 (d, J=15.1 Hz, 1 H), 3.72–3.90 (m, 1 H), 3.59 (q, J=6.3 Hz, 2 H), 3.30 (dd, J=15.0, 4.2 Hz, 1 H), 2.93 (dd, J=15.0, 9.3 Hz, 1 H), 2.64 (dd, J=15.6, 5.1 Hz, 1 H), 2.51 (dd, J=15.6, 9.3 Hz, 1 H), 2.10–2.30 (m, 2 H), 1.27 (t, J=7.1 Hz, 3 H); MS (ES) m/e 492 (M+H)+.

Preparation 17

Preparation of Ethyl (S)-10,11-dihydro-3-[3-(4-nitro-1-oxopyridin-2-ylamino)-1-propyloxy]-5H-dibenzo[a,d]cycloheptene-10-acetate a) Ethyl (S)-10,11-dihydro-3-[3-(4-nitro-1-oxopyridin-2-ylamino)-1-propyloxy]-5H-dibenzo[a,d]cycloheptene-10-acetate According to the procedure of Preparation 16, except substituting ethyl (S)-10,11-dihydro-3-hydroxy-5H-dibenzo[a,d]cycloheptene-10-acetate for the ethyl (±)-10,11-dihydro-3-hydroxy-5H-dibenzo[a,d]cycloheptene-10-acetate, the title compound was prepared: MS (ES) m/e 492 (M+H)+.

Preparation 18

Preparation of 10,11-Dihydro-3-methoxy-5H-dibenzo[a,d]cyclohepten-10-one a) 2-Benzyl-4-methoxyphenylacetic Acid A solution of 2-benzoyl-4-methoxyphenylacetic acid (13.0 g, 0.048 mol), prepared by the method of *J. Med. Chem.* 1981, 24, 998, in glacial acetic acid (600 mL) was treated under argon with 4.3 g. of 10% Pd/C and hydrogenated at 50 psi for 17 hours. The mixture was filtered using celite® and the filtrate was concentrated and reconcentrated from toluene and methylene chloride to give 14.2 of the title compound: $^1$H NMR (400 MHz, CDCl$_3$) δ3.52 (s, 2H), 3.75 (s, 3H), 4.0 (s, 3H), 6.7 (m, 2H), 7.15 (m, 6H).

b) 10,11-Dihydro-3-methoxy-5H-dibenzo[a,d]cyclohepten-10-one

A solution of 2-benzyl-4-methoxyphenylacetic acid (14.2 g, 0.055 m) in benzene (120 mL) and thionyl chloride (28 mL) was refluxed for 1 hour and concentrated. The acid chloride was dissolved in dry methylene chloride (40 mL), and the solution was added dropwise under argon to a solution of AlCl$_3$ (14.7 g, 0.11 mol) in methylene chloride (600 mL). The reaction was stirred under an argon atmosphere for 2.5 hours at room temperature, then was quenched with ice-water (200 mL). The layers were separated, and the organic phase was washed sequentially with 10% NaOH solution, water, and dil. HCl. The resulting solution was diluted with ether (200 mL), dried over MgSO$_4$, and concentrated. The solid residue was triturated with ether/hexane (1:1) and 9.35 g of the title compound was collected by filtration: Mp 105–106° C.; $^1$H NMR (400 MHz, CDCl$_3$) δ3.72 (s, 3H), 4.1 (s, 2H), 4.2 (s, 2H), 6.7 (d, 1H), 6.82 (s, 1H), 7.30 (m, 4H), 8.1 (d, 1H).

Preparation 19

Preparation of Ethyl (±)-10,11-dihydro-3-methoxy-5H-dibenzo[a,d]cycloheptene-10-acetate a) Ethyl (±) 3-(3-methoxyphenyl)indeneacetate To a cold solution of 3-(3-methoxyphenyl)indene (4 g, 18 mmol), prepared by the method of *J. Med. Chem.* 1981, 24, 998, in THF (15 mL) at 0° C. was added dropwise a solution of LiN(TMS)$_2$ (20 mL, 1M in THF) over 5 min. The resulting solution was added dropwise to a solution of ethyl bromoacetate (3.34 g, 20 mmol) in THF (15 mL) at −78° C. over 30 min. After 2.5 h, the mixture was quenched with saturated ammonium chloride solution and the layers were separated. The organic layer was dried over MgSO$_4$ and concentrated to give the crude product which was purified by column chromatography (SiO$_2$/2–4% EtOAc/hexane) to give title compound (1.1 g): $^1$H NMR (400 MHz, CDCl$_3$) δ1.30 (t, 3H), 2.50 (m, 1H), 2.85 (m, 1H), 3.85 (s, 3H), 4.0 (m, 1H), 4.20 (q, 2H), 6.6 (s, 1H), 6.9 (m, 1H), 7.2 (s, 1H), 7.35 (m, 6H).

b) Ethyl (±) 3-[(3-methoxybenzoyl)]phenylsuccinate

A solution of ethyl (±) 3-(3-methoxyphenyl)indeneacetate (1.1 g, 3.6 mmol) in acetone (30 mL) was treated with 4% aqueous solution of osmium tetroxide (0.5 mL) followed by a dropwise addition of 1.2 M Jones reagent (5 mL, 6 mmol) according to the literature procedure (*J. Org. Chem.* 1993, 58, 4745). After stirring overnight at room temperature, the dark reaction mixture was quenched with isopropanol (2.5 mL), followed by sodium bisulfite (0.9 g) and water (30 mL). The product was extracted with ethyl acetate, washed with brine, dried over MgSO$_4$, and concentrated to give a solid residue. Trituration with 1:1 ether/hexane gave 0.76 g of the title compound: $^1$H NMR (400 MHz, CDCl$_3$) δ1.18 (t, 3H), 2.90 (m, 1H), 3.3 (m, 1H), 3.92 (s, 3H), 4.1 (q, 2H), 4.4 (m, 1H), 4.4 (d, 1H), 7.25 (m, 2H), 7.5 (m, 6H).

c) Ethyl (±) 3-[(3-methoxybenzyl)]phenylsuccinate

A mixture of ethyl (±) 3-[(3-methoxybenzoyl)]phenylsuccinate (0.76 g., 2.1 mmol) and 10% Pd/C (0.6 g) in glacial acetic acid (35 mL) was hydrogenated at 50 psi for 17 hours. The mixture was filtered using celite® and the filter pad was washed with acetic acid. The filtrate was concentrated and reconcentrated from toluene and methylene chloride to give 0.65 g of the title compound: $^1$H NMR (400 MHz, CDCl$_3$) δ1.20 (t, 3H), 2.20 (m, 1H), 3.0 (m, 1H), 3.74 (s, 3H), 4.1 (q, 2H), 4.18 (q, 2H), 4.4 (d, 1H), 6.2 (m, 2H), 7.22 (m, 6H).

d) Ethyl (±)-10,11-dihydro-3-methoxy-11-oxo-5H-dibenzo[a,d]cycloheptene-10-acetate To a magnetically stirred solution of ethyl (±) 3-[(3-methoxybenzyl)]phenylsuccinate (0.65 g, 1.9 mmol) in dry methylene chloride (10 mL) were added DMF (0.2 mL) and oxalyl chloride (0.2 mL, 2.28 mmol). After 1.5 h, the solution was added dropwise to a suspension of aluminum chloride (0.6 g, 4.5 mmol) in dry methylene chloride (15 mL). The mixture was quenched after 2 h with ice water, the layers were separated, and the aqueous layer was extracted with methylene chloride. The combined organic layers were dried over MgSO$_4$ and concentrated. The residue was purified by column chromatography (SiO$_2$/2–4% EtOAc/hexane) to give title compound (0.3 g): $^1$H NMR (400 MHz, CDCl$_3$) δ1.28 (t, 3H), 2.88 (m, 1H), 3.55 (m, 1H), 3.84 (s 3H), 3.88 (d, 1H), 4.18 (q, 2H), 4.85 (d, 1H), 4.95 (m, 1H), 5.8 (m, 2H), 7.22 (m, 4H), 8.1 (s, 1H).

e) Ethyl (±)-10,11 dihydro-3-methoxy-5H-dibenzo[a,d]cycloheptene-10-acetate

A mixture of ethyl (±)-10,11-dihydro-3-methoxy-11-oxo-5H-dibenzo[a,d]cycloheptene-10-acetate (0.3 g., 0.93 mmol) and 10% Pd/C (0.3 g) in glacial acetic acid (25 mL) was hydrogenated at 50 psi for 18 hours. The mixture was filtered using celite® and washed with acetic acid. The filtrate was concentrated and reconcentrated from toluene and methylene chloride to give 0.25 g of the title compound: $^1$H NMR (400 MHz, CDCl$_3$) δ1.28 (t, 3H), 2.60 (m, 2H), 2.90 (m, 1H), 3.30 (m, 1H), 3.80 (s, 3H), 3.85 (d, 1H), 4.18 (q, 2H), 4.30 (d, 1H), 6.70 (m, 2H), 7.0 (d, 1 H), 7.22 (m, 4H).

Preparation 20

Preparation of ethyl (±)-10,11-dihydro-3-hydroxy-dibenzo[b,f]oxepine-10-acetate a) 4-Methoxy-2-phenoxyacetophenone According to the procedure of Harris, T. W. et al. (*J. Med. Chem.* 1982, 25(7), 855–858), 2-fluoro-4-methoxyacetophenone (1.00 g, 5.95 mmole) was reacted with phenol to give the title compound (1.27 g) as an oil: $^1$H NMR (300 MHz, CDCl$_3$) δ7.90 (d, J=8.8 Hz, 1 H), 7.35 (m, 2 H), 7.20 (m, 1 H), 7.05 (m, 2 H), 6.70 (dd, J=2.4, 8.8 Hz, 1 H), 6.35 (d, J=2.4 Hz, 1 H), 3.75 (s, 3 H), 2.61 (s, 3 H).

b) 2-(4-Methoxy-2-phenoxyphenyl)-1-morpholin-4-ylethan-1-thione

According to the procedure of Harris, T. W., et al. (i J. Med. Chem. 1982, 25(7), 855–858), 4-methoxy-2-phenoxyacetophenone (1.69 g, 6.98 mmole), sulfur (0.36 g, 11.2 mmole), and morpholine (0.98 mL, 11.2 mmole) were reacted to give the title compound (1.24 g) as a white solid: MS (ES) m/e 344.0 (M+H)$^+$.

c) 2-(4-Methoxy-2-phenoxyphenyl)acetic Acid

To a solution of 2-(4-methoxy-2-phenoxyphenyl)-1-morpholin-4-ylethan-1-thione (0.35 g, 1.02 mmole) in i-PrOH (15 mL) and H$_2$O (15 mL) was added KOH (0.57 g, 10.2 mmole). The reaction was heated at reflux for 18 hr, then was cooled to RT, diluted with H$_2$O, and washed with Et$_2$O. The aqueous layer was acidified to pH≈4 with conc. HCl and was extracted with CHCl$_3$. The combined extracts were dried over MgSO$_4$ and concentrated to give the title compound (0.22 g) as a white solid. This was used without further purification: MS (ES) m/e 259.0 (M+H)$^+$.

d) 3-Methoxydibenzo[b,f]oxepin-10-one

A solution of 2-(4-methoxy-2-phenoxyphenyl)acetic acid (594 mg, 2.3 mmole) in thionyl chloride (10 mL) was heated at reflux for 30 min, then was concentrated to dryness, and the residue was reconcentrated from toluene. The resulting residue was dissolved in dry CH$_2$Cl$_2$ (3 mL), and the solution was added dropwise at RT to a suspension of AlCl$_3$ (673 mg, 5.06 mmole) in dry CH$_2$Cl$_2$ (4 mL) in a flame-dried flask under argon. After stirring for 2.5 hr, the mixture was diluted with CH$_2$Cl$_2$ (10 mL) and washed sequentially with 1.0 N NaOH and brine. Drying (MgSO$_4$), concentration, and flash chromatography on silica gel (5% EtOAc/hexanes) gave the title compound (264 mg, 48%) as a light yellow oil: $^1$H NMR (300 MHz, CDCl$_3$) δ3.80 (s, 3 H), 4.02 (s, 2 H), 6.74–8.08 (m, 7 H).

e) Ethyl (±)-10,11-dihydro-10-hydroxy-3-methoxydibenzo[b,f]oxepine-10-acetate

Anhydrous EtOAc (0.94 mL, 9.6 mmole) was added dropwise to a solution of lithium bis(trimethylsilyl)amide (1.0 M in THF, 7 mL, 7 mmole) in dry THF (7 mL) in a flame-dried flask at −78° C. under argon. After 0.5 hr, TMEDA (2.4 mL, 16 mmole) was added. After another 5 min, a solution of 3-methoxydibenzo[b,f]oxepin-10-one (760 mg, 3.2 mmole) in THF (2 mL) was added dropwise over 3 min. Additional dry THF (0.4 mL) was used in transfer. The reaction was stirred at −78° C. to −40° C. for 1 hr, then was quenched with saturated NH$_4$Cl (10 mL). The mixture was warmed to RT and extracted with EtOAc. Drying (MgSO$_4$), concentration, and flash chromatography on silica gel (10% EtOAc/hexanes) gave the title compound as a clear oil: $^1$H NMR (300 MHz, CDCl$_3$) δ1.14–1.20 (t, 3 H), 1.21–1.30 (m, 1 H), 2.62–2.68 (dd, 1 H), 2.94–3.02 (dd, 1 H), 3.24–3.30 (dd, 1 H), 3.40–3.46 (dd, 1 H), 3.40–3.46 (dd, 1 H), 3.78 (s, 3 H), 4.08–4.18 (m, 2 H), 6.60–7.26 (m, 6 H), 7.64–7.68 (dd, 1 H).

f) Ethyl (±)-10,11-dihydro-3-methoxydibenzo[b,f]oxepine-10-acetate

Boron trifluoride etherate (0.48 mL, 3.9 mmole) was added to a solution of ethyl (±)-10,11-dihydro-10-hydroxy-3-methoxydibenzo[b,f]oxepine-10-acetate (690 mg, 1.95 mmole) and triethylsilane (0.62 mL, 3.9 mmole) in dry CH$_2$Cl$_2$ at 0° C. under argon. After 20 min, the reaction was quenched with 5% NaHCO$_3$, and the mixture was extracted with CH$_2$Cl$_2$. Drying (MgSO$_4$) and concentration gave a yellow oil. This was dissolved in absolute ethanol (20 mL) and 10% Pd/C (413 mg, 0.39 mmole) was added. The mixture was hydrogenated for 3 hr at 50 psi on a Parr hydrogenation apparatus. The catalyst was removed by filtration through celite®, and the filtrate was concentrated to afford the title compound (523 mg, 86%) as a clear oil. $^1$H NMR (300 MHz, CDCl$_3$) δ7.18–6.58 (m, 7 H), 4.18–4.08 (m, 2 H), 3.80 (s, 3 H), 3.80-3.74(m, 1 H), 3.40-3.30 (dd, 1 H). 2.98-2.84 (dd, 1 H), 2.74-2.62 (dd, 1 H), 2.60-2.52(m, 1 H), 1.32-1.20 (t, 3 H).

g) Ethyl (±)-10,11-dihydro-3-hydroxydibenzo[b,f]oxepine-10-acetate

A solution of ethyl (±)-10,11-dihydro-3-methoxydibenzo[b,f]oxepine-10-acetate (523 mg, 1.68 mmole) in CH$_2$Cl$_2$ (6.8 mL) was added dropwise to a cold solution of BBr$_3$ in CH$_2$Cl$_2$ (1.0 M, 6.7 mL, 6.7 mmole) at 0° C. under argon. The reaction was stirred for 20 min, then CH$_3$OH (7 mL) was added carefully. The mixture was concentrated and the residue was flash chromatographed on silica gel (15–20% EtOAc/hexanes) to afford the title compound (407 mg, 89%) as a pale yellow oil: MS (ES) m/e 299 (M+H)$^+$.

Preparation 21

Preparation of 2-[(3-bromo-1-propyl)amino]-4-methylpyridine-N-oxide hydrobromide a) 2-[(3-Bromo-1-propyl)amino]-4-methylpyridine-N-oxide hydrobromide A solution of SOBr$_2$ (5.0 mL, 64.5 mmole) in CH$_2$Cl$_2$ (20 mL) was added dropwise over 15–20 min to a solution of 2-[(3-hydroxy-1-propyl)amino]4-methylpyridine-N-oxide (10.0 g, 54.87 mmole) in CH$_2$Cl$_2$ (100 mL) at 0° C. The reaction was warmed to RT and stirred for 2 hr, then Et$_2$O (200 mL) was added slowly. The solvents were decanted away from the gummy precipitate, and the precipitate was washed with additional CH$_2$Cl$_2$/Et$_2$O (several times). The resulting brownish-yellow residue solidified on standing in a refrigerator overnight. This solid was collected and washed with Et$_2$O to afford the title compound (15.07 g) as a yellow solid. Additional title compound (2.05 g) was obtained as white needles by concentration of the combined organic layers. The total yield of title compound was 17.89 g (96%): MS (ES) m/e 245 and 247 (M+H)⁺.

The following compounds illustrate methods for preparing the biologically active compounds of this invention from intermediate compounds such as described in the foregoing Preparations.

Example 1

Preparation of (±)-10,11-dihydro-3-[4-(pyridin-2-ylamino)-1-butyl]-5H-dibenzo[a,d]cycloheptene-10-acetic Acid a) 4-(2-Tetrahydropyranyloxy)-1-tributylstannyl-1-butyne A solution of n-butyllithium in hexanes (1.6 M, 18.8 mL, 30 mmole) was added in a stream over 2 min to a solution of 2-(3-butynyloxy)tetrahydro-2H-pyran (4.7 mL, 30 mmole) in dry THF (60 mL) at 0° C. under argon. After 0.5 hr, tributyltin chloride (8.1 mL, 30 mmole) was added all at once, and the reaction was warmed to RT. After 3 hr, the reaction was diluted with hexanes (300 mL) and washed sequentially with $H_2O$ (2×60 mL), 10% KF (2×30 mL), and saturated brine (60 mL). Drying ($Na_2SO_4$), concentration, and silica gel chromatography (3% EtOAc/hexanes) gave the title compound (3.58 g, 27%) as a nearly colorless oil: TLC (5% EtOAc/hexanes) $R_f$0.37; $^1$H NMR (400 MHz, $CDCl_3$) δ4.66 (narrow t, 1 H), 3.75–3.96 (m, 2 H), 3.49–3.62 (m, 2 H), 2.56 (app t, 2 H), 1.76-1.91 (m, 1 H), 1.65–1.78 (m, 1 H), 1.42–1.65 (m, 10 H), 1.22–1.41 (m, 6 H), 0.82–1.08 (m, 15 H).

b) Ethyl (±)-10,11-dihydro-3-[4-(2-tetrahydropyranyloxy)-1-butyn-1-yl]-5H-dibenzo[a,d]cycloheptene-10-acetate A mixture of ethyl (±)-10,11-dihydro-3-(trifluoromethanesulfonyloxy)-5H-dibenzo[a,d]cycloheptene-10-acetate (1.34 g, 3.13 mmole), 4-(2-tetrahydropyranyloxy)-1-tributylstannyl-1-butyne (1.66 g, 3.76 mmole), LiCl (398 mg, 9.39 mmole), bis(triphenylphosphine)palladium dichloride (110 mg, 0.094 mmole), and anhydrous dioxane (31 mL) was heated at reflux under argon. After 1.5 hr, the reaction was concentrated to remove most of the dioxane, and the residue was taken up in $Et_2O$ (100 mL). 10% KF (50 mL) was added and the mixture was stirred briskly for 0.5 hr. The aqueous layer was removed and the $Et_2O$ layer was filtered through a mixture of celite® and $MgSO_4$. The filtrate was concentrated and the residue was chromatographed on silica gel (10% EtOAc/hexanes) to afford the title compound (1.12 g, 83%) as a pale yellow oil: TLC (20% EtOAc/hexanes) $R_f$0.40; $^1$H NMR (400 MHz, $CDCl_3$) δ7.21–7.30 (m, 1 H), 7.06–7.20 (m, 5 H), 7.00 (d, J=7.8 Hz, 1 H), 4.69 (t, J=3.6 Hz, 1 H), 4.31 (d, J=15.2 Hz, 1 H), 4.11–4.23 (m, 2 H), 3.76–3.97 (m, 4 H), 3.59–3.68 (m, 1 H), 3.48–3.57 (m, 1 H), 3.34 (dd, J=15.2, 4.1 Hz, 1 H), 2.97 (dd, J=15.2, 9.5 Hz, 1 H), 2.70 (t, J=7.3 Hz, 2 H), 2.65 (dd, J=15.7, 4.8 Hz, 1 H), 2.51 (dd, J=15.7, 9.5 Hz, 1 H), 1.78–1.92 (m, 1 H), 1.68–1.78 (m, 1 H), 1.44–1.68 (m, 4 H), 1.27 (t, J=7.1 Hz, 3 H); MS (ES) m/e 455 (M+Na)⁺.

c) Ethyl (±)-10,11-dihydro-3-[4-(2-tetrahydropyranyloxy)-1-butyl ]-5H-dibenzo[a,d]cycloheptene-10-acetate A mixture of ethyl (±)-10,11-dihydro-3-[4-(2-tetrahydropyranyloxy)-1-butyn-1-yl]-5H-dibenzo[a,d]cycloheptene-10-acetate (1.2 g, 2.77 mmole), 10% Pd/C (0.3 g, 0.28 mmole), and EtOAc (28 mL) was shaken at RT under hydrogen (50 psi) on a Parr apparatus. After 3 hr, the reaction was filtered through celite® and the filtrate was concentrated. Silica gel chromatography (10% EtOAc/hexanes) gave the title compound (1.06 g, 88%) as a colorless oil: TLC (20% EtOAc/hexanes) $R_f$0.51; $^1$H NMR (400 MHz, $CDCl_3$) δ7.05–7.20 (m, 4 H), 6.92–7.03 (m, 3 H), 4.53–4.60 (m, 1 H), 4.34 (d, J=15.1 Hz, 1 H), 4.12–4.26 (m, 2 H), 3.80–3.90 (m, 3 H), 3.71–3.80 (m, 1 H), 3.44–3.53 (m, 1 H), 3.35–3.44 (m, 1 H), 3.33 (dd, J=15.1, 4.1 Hz, 1 H), 2.95 (dd, J=15.1, 9.4 Hz, 1 H), 2.65 (dd, J=15.5, 4.9 Hz, 1 H), 2.49–2.61 (m, 3 H), 1.77–1.90 (m, 1 H), 1.45–1.77 (m, 9 H), 1.27 (t, J=7.1 Hz, 3 H); MS (ES) m/e 459 (M+Na)⁺.

d) Ethyl (±)-10,11-dihydro-3-(4-hydroxy-1-butyl)-5H-dibenzo[a,d]cycloheptene-10-acetate A solution of ethyl (±)-10,11-dihydro-3-[4-(2-tetrahydropyranyloxy)-1-butyl]-5H-dibenzo[a,d]cycloheptene-10-acetate (456.0 mg, 1.04 mmole) and p-toluenesulfonic acid monohydrate (60 mg, 0.31 mmole) in absolute EtOH (10 mL) was stirred at RT. After 2 hr, the reaction was quenched with 5% $NaHCO_3$ (1 mL) and concentrated to remove the EtOH. The residue was diluted with $H_2O$ (2 mL) and extracted with $CH_2Cl_2$. Drying ($MgSO_4$), concentration, and silica gel chromatography (1:1 EtOAc/hexanes) gave the title compound (342.4 mg, 93%) as a colorless oil: TLC (1:1 EtOAc/hexanes) $R_f$0.49; $^1$H NMR (250 MHz, $CDCl_3$) δ6.85–7.25 (m, 7 H), 4.34 (d, J=15.1 Hz, 1 H), 4.08–4.30 (m, 2 H), 3.75–3.95 (m, 2 H), 3.53–3.72 (m, 2 H), 3.33 (dd, J=15.1, 4.1 Hz, 1 H), 2.95 (dd, J=15.1, 9.4 Hz, 1 H), 2.40–2.75 (m, 4 H), 1.45–1.80 (m, 4 H), 1.27 (t, J=7.1 Hz, 3 H); MS (ES) m/e 353 (M+H)⁺.

e) Ethyl (±)-10,11-dihydro-3-[4-(N-phthalidimido)-1-butyl]-5H-dibenzo[a,d]cycloheptene-10-acetate Diethyl azodicarboxylate (0.2 mL, 1.26 mmole) was added dropwise to a solution of ethyl (±)-10,11-dihydro-3-(4-hydroxy-1-butyl)-5H-dibenzo[a,d]cycloheptene-10-acetate (0.37 g, 1.05 mmole), triphenylphosphine (0.33 g, 1.26 mmole), and phthalimide (0.19 g, 1.26 mmole) in anhydrous THF (10 mL) at RT under argon. After 23 hr, the reaction was concentrated on the rotavap. Silica gel chromatography (30% EtOAc/hexanes) gave the title compound (0.35 g, 70%) as a colorless oil: MS (ES) m/e 504.3 (M+Na)⁺.

f) Ethyl (±)-10,11-dihydro-3-(4-amino-1-butyl)-5H-dibenzo[a,d]cycloheptene-10-acetate Hydrazine monohydrate (0.11 g, 2.18 mmole) was added to a solution of ethyl (±)-10,11-dihydro-3-[4-(N-phthalidimido)-1-butyl]-5H-dibenzo[a,d]cycloheptene-10-acetate (0.35 g, 0.73 mmole) in absolute EtOH (10 mL) and toluene (2 mL) at RT. The reaction was stirred at RT for 17 hr, then was filtered, and the filter pad was washed with toluene. Concentration on the rotavap gave the title compound (0.23 g, 90%) as a colorless solid: MS (ES) m/e 352.3 (M+H)⁺.

g) Ethyl (±)-10,11-dihydro-3-[4(1-oxopyridin-2-ylamino)-1-butyl]-5H-dibenzo[a,d]cycloheptene-10-acetate A mixture of 2-chloropyridine-N-oxide hydrochloride (0.31 g, 1.88 mmole), ethyl (±)-10,11-dihydro-3-(4-amino-1-butyl)-5H-dibenzo[a,d]cycloheptene-10-acetate (0.22 g, 0.63 mmole), and NaHCO$_3$ (0.26 g, 3.13 mmole) in tert-amyl alcohol (6 mL) was heated at reflux for 21 hr. The reaction mixture was diluted with CH$_2$Cl$_2$ (100 mL) and filtered, and the filtrate was concentrated on the rotavap. Silica gel chromatography (1:9:5 MeOH/CH$_2$Cl$_2$/EtOAc) gave the title compound (82 mg, 30%) as a yellow oil: MS (ES) m/e 445.2 (M+H)$^+$.

h) Ethyl (±)-10,11-dihydro-3-[4-(pyridin-2-ylamino)-1-butyl]-5H-dibenzo[a,d]cycloheptene-10-acetate A mixture of ethyl (±)-10,11-dihydro-3-[4(1-oxopyridin-2-ylamino)-1-butyl]-5H-dibenzo[a,d]cycloheptene-10-acetate (0.07 g, 0.16 mmole), 10% Pd/C (0.08 g, 0.075 mmole), cyclohexene (0.16 mL, 1.6 mmole), and isopropanol (4 mL) was heated at reflux under argon for 14 hr, then the catalyst was removed by filtration through celite®. The filter pad was washed with isopropanol and MeOH, and the filtrate was concentrated on the rotavap to give the title compound (0.046 g, 69%) as a clear oil: MS (ES) m/e 429.3 (M+H)$^+$.

i) Ethyl (±)-10,11-dihydro-3-[4-(pyridin-2-ylamino)-1-butyl]-5H-dibenzo[a,d]cycloheptene-10-acetic Acid A mixture of ethyl (±)-10,11-dihydro-3-[4-(pyridin-2-ylamino)-1-butyl]-5H-dibenzo[a,d]cycloheptene-10-acetate (46 mg, 0.11 mmole) and 1.0 N LiOH (0.66 mL, 0.66 mmole) in THF (3 mL) and H$_2$O (3 mL) was stirred at RT. After 24 hr, the reaction mixture was concentrated on the rotavap, and the residue was diluted with H$_2$O (5 mL). The solution was cooled in an ice bath, and 1.0 N AcOH was added slowly to give a white precipitate. Chromatography on C-18 YMC (45% CH$_3$CN/H$_2$O containing 0.1% TFA) gave the title compound (13 mg, 21%) as a white solid: MS (ES) m/e 401.3 (M+H)$^+$. Anal. Calcd for C$_{26}$H$_{28}$N$_2$O$_2$·0.75 H$_2$O·1.5 CF$_3$CO$_2$H: C, 59.54; H, 5.31, N, 4.72. Found: C, 59.69; H, 5.31; N, 4.72.

Example 2

Preparation of (±)-10,11-dihydro3-[3-(4-ethoxypyridin-2-ylamino)-1-propyloxy]-5 H-dibenzo[a,d]cycloheptene-10-acetic acid a) Ethyl (±)-10,11-dihydro-3-[3-(4-ethoxy-1-oxopyridin-2-ylamino)-1-propyloxy]-5H-dibenzo[a,d]cycloheptene-10-acetate Ethyl (±)-10,11-dihydro-3-[3-(4-nitro-1-oxopyridin-2-ylamino)-1-propyloxy]-5 H-dibenzo[a,d]cycloheptene-10-acetate (0.67 g, 1.36 mmole), 1.0 M NaOEt in ethanol (6.8 mL, 6.8 mmole), and absolute ethanol (6.8 mL) were combined, and the mixture was warmed in an oil bath preset at 70° C. A dark solution was produced, which was warmed for 10 min, then the oil bath was removed, and the solution was allowed to stir for an additional 5–7 min without external heating. The resulting solution was cooled in ice, and the reaction was quenched with glacial acetic acid (0.47 mL, 8.2 mmole). The mixture was concentrated and the residue was partitioned between CH$_2$Cl$_2$ (10 mL) and half-saturated NH$_4$Cl (10 mL). The layers were separated and the aqueous layer was extracted with CH$_2$Cl$_2$ (2×10 mL). The combined organic layers were dried (MgSO$_4$) and concentrated, and the residue was reconcentrated from toluene to leave a reddish-orange oil. Silica gel chromatography (5% MeOH/CHCl$_3$) gave the title compound (601.1 mg, 90%) as a yellow oil: TLC (5% MeOH/CHCl$_3$) R$_f$0.36; $^1$H NMR (250 MHz, CDCl$_3$) δ7.95 (d, J=7.1 Hz, 1 H), 6.88–7.30 (m, 6 H), 6.77 (d, J=2.6 Hz, 1 H), 6.67 (dd, J=8.2, 2.6 Hz, 1 H), 5.95–6.20 (m, 2 H), 4.28 (d, J=15.0 Hz, 1 H), 4.18 (q, J=7.2 Hz, 2 H), 4.04 (t, J=5.6 Hz, 2 H), 3.65–4.00 (m, 4 H), 3.46 (q, J=6.5 Hz, 2 H), 3.30 (dd, J=15.0, 4.2 Hz, 1 H), 2.93 (dd, J=15.0, 9.2 Hz, 1 H), 2.65 (dd, J=15.6, 5.0 Hz, 1 H), 2.52 (dd, J=15.6, 9.4 Hz, 1 H), 1.95–2.25 (m, 2 H), 1.10–1.45 (m, 6 H); MS (ES) m/e 491 (M+H)$^+$.

b) Ethyl (±)-10,11-dihydro-3-[3-(4-ethoxypyridin-2-ylamino)-1-propyloxy]-5H-dibenzo[a,d]cycloheptene-10-acetate A mixture of ethyl (±)-10,11-dihydro-3-[3-(4-ethoxy-1-oxopyridin-2-ylamino)-1-propyloxy]-5H-dibenzo[a,d]cycloheptene-10-acetate (601.1 mg, 1.23 mmole), cyclohexene (1.2 mL, 12.3 mmole), 10% Pd/C (130 mg, 0.012 mmole), and absolute ethanol (12.3 mL) was heated at reflux under argon. After 23.5 hr, the reaction was hot-filtered through celite® and the filter pad was washed with ethanol. The filtrate was concentrated and the residue was reconcentrated from toluene. Silica gel chromatography (5% MeOH in 1:1 EtOAc/CHCl$_3$) gave the title compound (528.1 mg, 90%) as a light yellow oil: TLC (10% MeOH in EtOAc/CHCl$_3$) R$_f$0.67; $^1$H NMR (400 MHz, CDCl$_3$) δ7.89 (d, J=5.8 Hz, 1 H), 7.05–7.18 (m, 4 H), 6.99 (d, J=8.2 Hz, 1 H), 6.77 (d, J=2.6 Hz, 1 H), 6.66 (dd, J=8.2 2.6 Hz, 1 H), 6.17 (dd, J=5.8, 2.1 Hz, 1 H), 5.86 (d, J=2.1 Hz, 1 H), 4.73 (br t, 1 H), 4.28 (d, J=14.9 Hz, 1 H), 4.11–4.25 (m, 2 H), 4.04 (t, J=5.9 Hz, 2 H), 3.98 (q, J=7.0 Hz, 2 H), 3.83 (d, J=14.9 Hz, 1 H), 3.76–3.85 (m, 1 H), 3.43 (q, J=6.4 Hz, 2 H), 3.30 (dd, J=15.0, 4.1 Hz, 1 H), 2.93 (dd, J=15.0, 9.2 Hz, 1 H), 2.64 (dd, J=15.6, 4.8 Hz, 1 H), 2.52 (dd, J=15.6, 9.5 Hz, 1 H), 2.01–2.11 (m, 2H), 1.37(t, J=7.0 Hz, 3H), 1.27 (t, J=7.0 Hz, 3 H); MS (ES) m/e 475 (M+H)$^+$.

c) (±)-10,11-Dihydro-3-[3-(4-ethoxypyridin-2-ylamino)-1-propyloxy]-5H-dibenzo[a,d]cycloheptene-10-acetic Acid 1.0 N NaOH (1.7 mL, 1.7 mmole) was added dropwise to a solution of ethyl (±)-10,11-dihydro-3-[3-(4-ethoxypyridin-2-ylamino)-1-propyloxy]-5H-dibenzo[a,d]cycloheptene-10-acetate (528.1 mg, 1.11 mmole) in absolute ethanol (11 mL) at RT, and the solution was warmed in an oil bath preset at 45° C. After 20 hr, the reaction was concentrated, and the residue was reconcentrated from H$_2$O. The resulting residue was dissolved in H$_2$O (10 mL) and the solution was filtered. The pH was adjusted to 7 with 1.0 N HCl, and the mixture was stirred briskly to convert the initially-formed gummy precipitate into a solid. Trituration with a glass rod and a spatula aided in this transformation. The pH of the resulting mixture was readjusted to 7, and the solid was collected and washed with plenty of H$_2$O. The filtrate was concentrated and the residue was dissolved in H$_2$O with the aid of a little 1.0 N NaOH. The pH was adjusted to 7 to afford a small second crop. The crops were combined and dried in vacuum (40–50° C.) to afford the title compound (453.7 mg, 82%) as an off-white solid: HPLC (Hamilton PRP-1®, 45% CH$_3$CN/H$_2$O containing 0.1% TFA) k'=1.32; $^1$H NMR (400 MHz, DMSO-d$_6$) δ7.78 (d, J=6.6 Hz, 1 H), 7.35–7.65 (m, 1 H), 7.02–7.22 (m, 4 H), 6.97 (d, J=8.3 Hz, 1 H), 6.82 (d, J=2.4 Hz, 1 H), 6.68 (dd, J=8.3, 2.4 Hz, 1 H), 6.29 (dd, 1 H), 6.15 (narrow d, 1 H), 4.20 (d, J=14.6 Hz, 1 H), 3.93–4.12 (m, 4 H), 3.89 (d, J=14.6 Hz, 1 H), 3.60–3.71 (m, 1 H), 3.30–3.50 (m, 2 H), 3.20 (dd, J=15.1, 4.1 Hz, 1 H), 2.83 (dd, J=15.1, 10.1 Hz, 1 H), 2.60 (dd, J=16.0, 5.3 Hz, 1 H), 2.48 (dd, J=16.0, 8.9 Hz, 1 H, partially obscured by residual solvent signal), 1.90–2.05 (m, 2 H), 1.30 (t, J=6.9 Hz, 3 H); MS (ES) m/e 447 (M+H)$^+$. Anal. Calcd for $C_{27}H_{30}N_2O_4 \cdot 1.5$ HCl: C, 64.70; H, 6.33; N, 5.59. Found: C, 64.53; H, 6.14; N, 5.31.

Example 3

Preparation of (±)-10,11-dihydro-3-[2-[2-(ethylamino)thiazol-4-yl]-ethoxy]-5 H-dibenzo[a,d] cycloheptene-10-acetic Acid a) Ethyl (±)-10,11-dihydro-3-[2-[2-(ethylamino) thiazol-4-yl]-1-ethoxy]-5 H-dibenzo[a,d] cycloheptene-10-acetate A solution of 2-(ethylamino)-4-thiazoleethanol (0.33 g, 1.9 mmole) and diethyl azodicarboxylate (0.30 mL, 1.9 mmole) in anhydrous DMF (5 mL) was added dropwise over 5 min to a solution of ethyl (±)-10,11-dihydro-3-hydroxy-5H-dibenzo[a,d]cycloheptene-10-acetate (296.4 mg, 1 mmole) and triphenylphosphine (525 mg, 2 mmole) in anhydrous DMF (5 mL) at RT. The reaction was kept cool in a RT water bath during the addition. After 16 hr, the reaction was concentrated and the residue was reconcentrated from xylenes (2×). Silica gel chromatography (20% EtOAc/hexanes) gave the title compound (145.0 mg, 32%) as a yellow oil: TLC (1:1 EtOAc/hexanes) $R_f$ 0.60; 1H NMR (250 MHz, CDCl$_3$) δ 7.00–7.30 (m, 4 H), 6.98 (d, J=8.2 Hz, 1 H), 6.77 (d, J=2.6 Hz, 1 H), 6.68 (dd, J=8.2, 2.6 Hz, 1 H), 6.21 (s, 1 H), 5.00–5.25 (m, 1 H), 4.04–4.38 (m, 5 H), 3.81 (d, J=15.1 Hz, 1 H), 3.70–3.90 (m, 1 H), 3.13–3.40 (m, 3 H), 2.99 (t, J=6.7 Hz, 2H), 2.92(dd, J=14.9, 9.3 Hz, 1 H), 2.64 (dd, J=15.6, 5.0 Hz, 1 H), 2.51 (dd, J=15.6, 9.3 Hz, 1 H), 1.27 (t, J=7.2 Hz, 3 H); MS (ES) m/e 451 (M+H)$^+$.

b) (±)-10,11-Dihydro-3-[2-[2-(ethylamino)thiazol-4-yl]-1-ethoxy]-5H-dibenzo[a,d]cycloheptene-10-acetic Acid 1.0 N LiOH (0.32 mL, 0.32 mmole) was added dropwise to a solution of ethyl (±)-10,11-dihydro-3-[2-[2-(ethylamino)thiazol-4-yl]-1-ethoxy]-5H-dibenzo[a,d] cycloheptene-10-acetate (145.0 mg, 0.32 mmole) in THF (2.4 mL) and H$_2$O (0.48 mL) at 0° C. The resulting pinkish-orange two-phase mixture was stirred at 0° C. for 10 min, during which time the color faded to orangish-yellow, then was warmed to RT. After 1.5 hr, a little more H$_2$O (5 drops) was added, and the reaction was stirred for 42 hr, then was cooled to 0° C. and neutralized with TFA (0.025 mL). The THF was removed on the rotavap, and the resulting oily residue was diluted with 0.1% TFA/CH$_3$CN to give a homogeneous solution. ODS chromatography (gradient: 40% CH$_3$CN/H$_2$O containing 0.1% TFA, then 45% CH$_3$CN/H$_2$O containing 0.1% TFA) gave fractions containing the title compound. These were pooled, and the CH$_3$CN was removed on the rotavap. The resulting aqueous mixture was made basic at 0° C. to afford a homogeneous solution. Careful acidification to pH 4–5 with 1.0 N HCl gave a solid precipitate, which was collected, washed with plenty of H$_2$O, and dried to afford the title compound (80.9 mg, 51%) as an off-white solid: HPLC (Hamilton PRP-1®, 45% CH$_3$CN/H$_2$O containing 0.1% TFA) k'=0.89; $^1$H NMR (400 MHz, CD$_3$OD) δ 7.02–7.18 (m, 4 H), 7.00 (d, J=8.3 Hz, 1 H), 6.79 (d, J=2.6 Hz, 1 H), 6.68 (dd, J=8.3, 2.6 Hz, 1 H), 6.45 (s, 1 H), 4.26 (d, J=14.9 Hz, 1 H), 4.20 (t, J=6.4 Hz, 2 H), 3.87 (d, J=14.9 Hz, 1 H), 3.68–3.80 (m, 1 H), 3.34 (q, J=7.3 Hz, 2 H, partially obscured by residual solvent signal), 3.30 (dd, 1 H, obscured by residual solvent signal), 2.99 (t, J=6.4 Hz, 2 H), 2.92 (dd, J=15.0, 9.4 Hz, 1 H), 2.62 (dd, J=15.9, 5.0 Hz, 1 H), 2.47 (dd, J=15.9, 9.3 Hz, 1 H), 1.27 (t, J=7.3 Hz, 3 H); MS (ES) m/e 423 (M+H)$^+$. Anal. Calcd for $C_{24}H_{26}N_2O_3S \cdot 0.67$ CF$_3$CO$_2$H: C, 61.03; H, 5.39; N, 5.62. Found: C, 61.21; H, 5.36; N, 5.60.

Example 4

Preparation of (S)-10,11-dihydro-3-[3-(pyridin-2-ylamino)-1-propyloxy]-5H-dibenzo[a,d] cycloheptene-10-acetic Acid a) Ethyl (S)-10,11-dihydro-3-[3-(1-oxopyridin-2-ylamino)-1-propyloxy]-5H-dibenzo[a,d] cycloheptene-10-acetate To a stirred solution of ethyl (S)-10,11-dihydro-3-hydroxy-5H-dibenzo[a,d]cycloheptene-10-acetate (35 g, 118 mmol) in dry THF (1.1 L) and dry DMF (600 mL) under argon were added 2-[(3-hydroxy-1-propyl)amino]pyridine-N-oxide (29.4 g, 175 mmol) and triphenylphosphine (45.9 g, 175 mmol). After all solids had completely dissolved (~1 h), the reaction was cooled to 0° C. in an ice bath and diisopropyl azodicarboxylate (36.4 mL, 95%, 175 mmol) was added via syringe. The reaction was allowed to warm slowly to RT and was stirred for 18 h. Concentration and flash chromatography on silica gel (95:5 CHCl$_3$/MeOH) followed by a second purification by flash chromatography on silica gel (80:20:5 CHCl$_3$/EtOAc/EtOH) gave the title compound (37.66 g, 71%) as a pale yellow solid foam: $^1$H NMR (400 MHz, DMSO-d$_6$) δ 8.08 (dd, J=6.3, 1.1 Hz, 1H), 7.29 (t, 1H), 7.19–7.06 (m, 5H), 6.97 (d, J=8.3 Hz, 1H), 6.84 (d, J=2.5, 1H), 6.79 (dd, J=8.5, 1.6 Hz, 1H), 6.69 (dd, J=8.3, 2.6 Hz, 1H), 6.57 (m, 1H), 4.17 (d, J=14.7 Hz, 1H), 4.13-4.07 (m, 2H), 4.00 (t, 2H), 3.91 (d, J=14.7 Hz, 1H), 3.66 (m, 1H), 3.39 (t, 2H), 3.19 (dd, J=15.1, 4.5 Hz, 1H), 2.85 (dd, J=15.1, 10.0 Hz, 1H), 2.65 (dd, J=15.8, 5.4 Hz, 1H), 1.99 (m, 2H), 1.18 (t, 3H), MS (ES) m/e 447.3 (M+H)$^+$.

b) Ethyl (S)-10,11-dihydro-3-[3-(pyridin-2-ylamino)-1-propyloxy]-5H-dibenzo[a,d] cycloheptene-10-acetate To a stirred solution of ethyl (S)-10,11-dihydro-3-(1-oxopyridin-2-ylamino)-1-propyloxy]-5H-dibenzo[a,d] cycloheptene-10-acetate (37.66 g, 84 mmol) in isopropanol (700 mL) were added 10% palladium on activated carbon (18 g, 16.9 mmol, carefully pre-wetted in isopropanol under argon) and cyclohexene (85 mL, 839 mmol). The reaction was then heated to reflux under argon in an oil bath set at 90° C. After 6 h an additional amount of 10% palladium on activated carbon (18 g, 84 mmol, carefully pre-wetted in isopropanol under argon) and cyclohexene (85 mL, 839 mmol) were added. After an additional 18 h the reaction was hot-filtered through celite®, and the filter pad was washed with 1:1 MeOH/CHCl$_3$ (600 mL). The filtrate was concentrated under vacuum and the residue was purified by flash chromatography on silica gel (95:5 CHCl$_3$/MeOH) to give the title compound (29.2 g, 81%) as a pale yellow oil: $^1$H NMR (400 MHz, DMSO-d$_6$) δ 7.94 (dd, J=5.4, 1.9 Hz, 1H), 7.35-7.31 (m, 1H), 7.18 (d, J=7.2 Hz, 1H), 7.14-7.06 (m, 3H) 6.97 (d. J=8.3 Hz, 1H), 6.83 (d, J=2.6, 1H), 6.68 (dd, J=8.3, 2.6 Hz, 1H), 6.54 (t, 1H), 6.44 (m, 2H), 4.17 (d, J=14.6 Hz, 1H), 4.13-4.02 (m, 2H), 4.00 (t, 2 H), 3.91 (d, J=14.7 Hz, 1H), 3.66 (m, 1H), 3.35 (m, 2H), 3.19 (dd, J=15.1, 4.4 Hz, 1H), 2.86 (dd, J=15.1, 10.1 Hz, 1H), 2.65 (dd, J=15.8, 5.4 Hz, 1H), 2.55 (dd, J=15.8, 8.7 Hz, 1H), 1.93 (m, 2H), 1.18 (t, 3H); MS (ES) m/e 431.4 (M+H)$^+$.

c) (S)-10,11-Dihydro-3-[3-(pyridin-2-ylamino)-1-propyloxy]-5H-dibenzo[a,d]cycloheptene-10-acetic acid To a stirred solution of ethyl (S)-10,11-dihydro-3-[3-(pyridin-2-ylamino)-1-propyloxy]-5H-dibenzo[a,d]

cycloheptene-10-acetate (29.20 g, 68 mmol) in dioxane (350 mL) was added aqueous 1.0 N NaOH (110 mL, 110 mmol). The cloudy reaction was stirred at 50° C. in an oil bath for 24 h, then the resulting homogeneous solution was neutralized with aqueous 1.0 N HCl (110 mL, 110 mmol). The solution was concentrated to near dryness by rotary evaporation to precipitate out the product. The supernatant was decanted off and the remaining gummy solid was dried under vacuum and redissolved in 1:1 methanol/$CHCl_3$. The clear solution was then reconcentrated by rotary evaporation and thoroughly dried under vacuum. The remaining solid was triturated with a small volume of water, filtered and dried under vacuum to give the title compound (26.85 g, 94%) as an off-white powder: HPLC (Hamilton PRP-1®, 35% $CH_3CN/H_2O$ containing 0.1% TFA) k'=2.88; $^1$H NMR (400 MHz, DMSO-$d_6$) δ7.94 (dd, J=4.7, 1.6 Hz, 1H), 7.38 (m, 1 H), 7.18 (d, J=7.3 Hz, 1H), 7.14 (d, J=3.9 Hz, 2H), 7.08 (m, 1H), 6.97 (d, J=8.4 Hz, 1H),6.83 (d, J=8.6 Hz, 1H), 6.78 (br s, 1H), 6.68 (dd, J=8.3. 2.6 Hz, 1H), 6.50 (d, J=8.3 Hz, 1H), 6.47 (dd, 1H), 4.20 (d, J=14.6 Hz, 1H), 4.00 (t, 2 H), 3.88 (d, J=14.6 Hz, 1 H), 3.67 (m, 1H), 3.37 (m, 1 H), 3.20 (dd, J=1.2, 4.4 Hz, 1H), 2.83 (dd, J=15.2, 10.1 Hz, 1H), 2.60 (dd, J=15.9, 5.3 Hz, 1H), 2.50 (dd, 1H), 1.95 (m, 2 H); MS (ES) m/e 403.3 (M+H)$^+$ Anal. Calcd for $C_{25}H_{26}N_2O_3.H_2O$: C, 71.41; H, 6.71; N, 6.66. Found: C, 71.21; H, 6.53: N, 6.54.

Example 5

Preparation of (±)-10,11-dihydro-3-[2-(6-aminopyridin-2-yl)-1-ethoxy]-5H-dibenzo[a,d] cycloheptene-10-acetic Acid a) Ethyl (±)-10,11-dihydro-3-[2-(6-aminopyridin-2-yl)-1-ethoxy]-5H-dibenzo[a,d]cycloheptene 10-acetate A solution of 6-amino-2-pyridylethanol (0.23 g, 1.68 mmole) and diethyl azodicarboxylate (0.26 mL, 1.68 mmole) in anhydrous DMF (5 mL) was added dropwise to a solution of ethyl (±)-10,11-dihydro-3-hydroxy-5H-dibenzo[a,d]cycloheptene-10-acetate and triphenylphosphine (0.48 g, 1.82 mmole) in anhydrous DMF (5 mL) at RT. After 1 hr, the reaction was concentrated and the residue was purified by flash chromatography on silica gel (1:1 EtOAc/hexanes) to afford the title compound (0.030 g): MS (ES) m/e 417 (M+H)$^+$.

b) (±)-10,11-Dihydro-3-[2-(6-aminopyridin-2-yl)-1-ethoxy]-5H-dibenzo[a,d]cycloheptene-10-acetic Acid A solution of ethyl (±)-10,11-dihydro-3-[2-(6-aminopyridin-2-yl)-1-ethoxy]-5H-dibenzo[a,d] cycloheptene-10-acetate (0.030 g, 0.072 mmole) and 1.0 N NaOH (0.14 mL, 0.14 mmole) in MeOH (2 mL) was stirred at RT overnight, then was concentrated. The residue was dissolved in $H_2O$ and the pH of the solution was adjusted to 7 with 1.0 N HCl. Concentration and chromatography on a C-18 Bond Elute column (10:9:1 $CH_3CN/H_2O$/TFA) gave the title compound (0.013 g): MS (ES) m/e 389 (M+H)$^+$.

Example 6

Preparation of (R)-10,11-dihydro-3-[3-(pyridin-2-ylamino)-1-propyloxy]-5H-dibenzo[a,d] cycloheptene-10-acetic Acid a) Ethyl (R)-10,11-dihydro-3-[3-(1-oxopyridin-2-ylamino)-1-propyloxy]-5H-dibenzo[a,d] cycloheptene-10-acetate A solution of 2-[(3-hydroxy-1-propyl)amino]pyridine-N-oxide (0.70 g, 4 mmole) and diethyl azodicarboxylate (0.65 mL, 4 mmole) in anhydrous DMF (20 mL) was added dropwise over 10 min to a solution of ethyl (R)-10,11-dihydro-3-hydroxy-5H-dibenzo[a,d]cycloheptene-10-acetate (0.45 g, 2 mmole) and triphenylphosphine (1.2 g, 4 mmole) in anhydrous DMF (8 mL) at RT under argon. After 23.5 hr, the reaction was concentrated on the rotavap, and the residue was reconcentrated from xylenes to remove residual DMF. Silica gel chromatography (1–4% $CH_3OH$/$CH_2Cl_2$) gave the title compound (0.50 g, 74%) as a yellow oil: MS (ES) m/e 447 (M+H)$^+$.

b) Ethyl (R)-10,11-dihydro-3-[3-(pyridin-2-ylamino)-1-propyloxy]-5H-dibenzo[a,d] cycloheptene-10-acetate A mixture of ethyl (R)-10,11-dihydro-3-[3-(1-oxopyridin-2-ylamino)-1-propyloxy]-5H-dibenzo[a,d]cycloheptene-10-acetate (0.5 g, 1 mmole), 10% Pd/C (0.25 g, 0.2 mmole), cyclohexene (2 mL, 20 mmole), and isopropanol (10 mL) was heated at reflux for 18 hr, then the catalyst was removed by filtration through celite®. Silica gel chromatography (0.5–2% $CH_3OH/CH_2Cl_2$) gave the title compound (0.4 g, 83%) as a light yellow oil: MS (ES) m/e 431 (M+H)$^+$.

c) (R)-10,11-Dihydro 3-[3-(pyridin-2-ylamino)-1-propyloxy]-5H-dibenzo[a,d]cycloheptene-10-acetic Acid A mixture of ethyl (R)-10,11-dihydro-3-[3-(pyridin-2-ylamino)-1-propyloxy]-5H-dibenzo[a,d]cycloheptene-10-acetate (0.4 g, 0.93 mmole) and 1.0 N NaOH (1.1 mL, 1.1 mmole) in absolute EtOH (10 mL) was warmed in an oil bath set at 50° C. After 18 hr, the reaction was concentrated on the rotavap and the residue was dissolved in $H_2O$. The aqueous solution was adjusted to pH 4 with 3 N HCl, and the solid precipitate was collected and washed with $H_2O$. The material was dried in high vacuum at 40° C. to afford the title compound (0.36 g, 96%) as a nearly colorless solid: $[\alpha]_D$ +50.8° (c=0.12, $CH_3OH$); MS (ES) m/e 403 (M+H)$^+$. Anal. Calcd for $C_{25}H_{26}N_2O_3.0.5$ $H_2O$: C, 72.97; H, 6.61; 6.80. Found: C, 73.09; H, 6.38; N, 6.58.

Example 7

Preparation of (S)-10,11-dihydro-3-[2-[6-(methylamino)pyridin-2-yl]-1-ethoxyl-5 H-dibenzo [a,d]cycloheptene-10-acetic Acid a) Ethyl (S)-10,11-dihydro-3-[2-[6-(methylamino) pyridin-2-yl]-1-ethoxy]-5 H-dibenzo[a,d] cycloheptene-10-acetate According to the procedure of Example 6 (a), except substituting 6-(methylamino)-2-pyridylethanol for the 2-[(3-hydroxy-1-propyl)amino]pyridine-N-oxide, and ethyl (S)-10,11-dihydro-3-hydroxy-5H-dibenzo[a,d]cycloheptene-10-acetate for ethyl (R)-10,11-dihydro-3-hydroxy-5H-dibenzo[a,d]cycloheptene-10-acetate, the title compound was obtained as colorless oil following silica gel chromatography (0.2–2% MeOH/$CH_2Cl_2$): MS (ES) 431.2 (M+H)$^+$.

b) (S)-10,11-Dihydro-3-[2-[6-(methylamino)pyridin-2-yl]-1-ethoxy]-5H-dibenzo[a,d]cycloheptene-10-acetic Acid Ethyl (S)-10,11-dihydro-3-[2-[6-(methylamino)pyridin-2-yl]-1-ethoxy]-5H-dibenzo[a,d]cycloheptene-10-acetate (80 mg, 0.18 mmol) was dissolved in THF (4 mL), and a solution of LiOH $H_2O$ (35 mg, 0.84 mmole) in $H_2O$ (4 mL) was added. The solution was stirred at RT for 72 hr, then was diluted with ether (10 mL). The supernatant was decanted and the solid was suspended in $H_2O$. Careful acidification to pH 4 with 3 N HCl gave the title compound as a white solid: MS(ES) 403 $(M+H)^+$. Anal. Calcd for $C_{25}H_{26}N_2O_3.0.75$ $H_2O$: C, 72.18; H, 6.66; N, 6.73. Found: C, 72.44; H, 6.52; N, 6.71.

Example 8

Preparation of (±)-10,11-dihydro-3-[3-(3,4,5,-tetrahydropyrimidin-2-ylamino)-1-propyloxy]-5H-dibenzo[a,d]cycloheptene-10-acetic Acid a) Ethyl (±)-10,11-dihydro-3-[3-(4-nitrobenzyloxycarbonyl)amino-1-propyloxy]-5H-dibenzo[a,d]cycloheptene-10-acetate According to the procedure of Example 6 (a), except substituting 3-(4-nitrobenzyloxycarbonylamino)-1-propanol for the 2-[(3-hydroxy-1-propyl)amino]pyridine-N-oxide, and ethyl (±)-10,11-dihydro-3-hydroxy-5H-dibenzo[a,d] cycloheptene-10-acetate for ethyl (R)-10,11-dihydro-3-hydroxy-5H-dibenzo[a,d]cycloheptene-10-acetate, the title compound was obtained as amber oil: MS (ES) 533.3 $(M+H)^+$.

b) Ethyl (±)-10,11-dihydro-3-(3-amino-1-propyloxy)-5H-dibenzo[a,d]cycloheptene-10-acetate A mixture of ethyl (±)-10,11-dihydro-3-[3-(4-nitrobenzyloxycarbonylamino)-1-propyloxy]-5H-dibenzo [a,d]cycloheptene-10-acetate (1.6 g 3 mmol), 10% palladium on charcoal (0.8 g, 1 mmol), and ethanol (50 mL) was shaken under $H_2$ (48 psi) for 3 hr, then the catalyst was removed by filtration through celite®D. The filtrate was concentrated to give the title compound (1.2 g, 100%) as a yellow oil: MS (ES) 348.2 $(M+H)^+$.

c) Ethyl (±)-10,11-dihydro-3-[3-(pyrimidin-2-ylamino)-1-propyloxy]-5H-dibenzo[a,d]cycloheptene-10-acetate A mixture of ethyl (±)-10,11-dihydro-3-(3-amino-1-propyloxy)-5H-dibenzo[a,d]cycloheptene-10-acetate (0.4 g, 1 mmole), sodium bicarbonate (0.5 g, 6 mmole), 2-bromopyrimidine (0.34 g, 2 mmole) and ethanol (10 mL) was heated at reflux under argon for 18 hr. The solution was then decanted and concentrated. The residue was purified by chromatography on silica gel (0.2–2% $MeOH/CH_2Cl_2$) to give the title compound (0.17 g, 34%) as a pale yellow oil: MS (ES) 432.3 $(M+H)^+$.

d) Ethyl (±)-10,11-dihydro-3-[3-(3,4,5,6-tetrahydropyrimid-2-ylamino)-1-propyloxy]-5 H-dibenzo[a,d]cycloheptene-10-acetate A mixture of ethyl (±)-10,11-dihydro-3-[3-(pyrimidin-2-ylamino)1-propyloxy]-5H-dibenzo[a,d]cycloheptene-10-acetate (0.17 g, 0.38 mmol), 10% palladium on charcoal (0.085 g, 0.08 mmol), 4 M HCl in dioxane (0.1 mL, 0.4 mmol) and ethanol (5 mL) was shaken under $H_2$ (48 psi) for 6 hr, then the catalyst was removed by filtration through celite®. The filtrate was concentrated to give the title compound (0.19 g) as a yellow oil: MS (ES) 436.3 $(M+H)^+$.

e) (±)-10,11-Dihydro-3-[3-(3,4,5,6-tetrahydropyrimid-2-ylamino)-1-propyloxy]-5H-dibenzo[a,d]cycloheptene-10-acetic Acid A solution of ethyl (±)-10,11-dihydro-3-[3-(3,4,5,6-tetrahydropyrimid-2-ylamino)-1-propyloxy]-5H-dibenzo[a, d]cycloheptene-10-acetate (0.17 g, 0.36 mmol), lithium hydroxide monohydrate (0.042 g, 1 mmol), THF (3 mL), and water (10 mL) was stirred at room temperature for 20 hr, then was concentrated. The residue was dissolved in water, and the solution was brought to pH 4 with 3 N HCl. The resulting solution was kept in the refrigerator overnight, then the supernatant was decanted away from the solid. The solid was dried in vacuum to give the title compound (0.145 g, 91%) as a tan solid: MS (ES) 408.3 $(M+H)^+$. Anal. Calcd for $C_{24}H_{29}N_3O_3.1.3$ HCl: C, 63.37; H,6.71; N, 9.23. Found: C, 63.67; H, 6.84; N, 9.46.

Example 9

Preparation of (±)-10,11-dihydro-3-[3-(isoquinoline-1-ylamino)-1-propyloxyl-5H-dibenzo[a,d] cycloheptene-10-acetic Acid a) Ethyl (±)-10,11-dihydro-3-[3-(1-oxoisoquinoline-1-ylamino)-1-propyloxy]-5H-dibenzo[a,d]cycloheptene-10-acetate According to the procedure of Example 6 (a), except substituting 1-[(3-hydroxy-1-propyl)amino]-isoquinoline N-oxide for the 2-[(3-hydroxy-1-propyl)amino]pyridine-N-oxide, and substituting ethyl (±)-10,11-dihydro-3-hydroxy-5H-dibenzo[a,d]cycloheptene-10-acetate for the ethyl (R)-10,11-dihydro-3-hydroxy-5H-dibenzo[a,d]cycloheptene-10-acetate, the title compound was prepared as a pale yellow oil: MS (ES) m/e 497.2 $(M+H)^+$.

b) Ethyl (±)-10,11-dihydro-3-[3-(isoquinoline-1-ylamino)-1-propyloxy]-5H-dibenzo[a,d]cycloheptene-10-acetate According to the procedure of Example 6 (b), except substituting ethyl (±)-10,11-dihydro-3-[3-(1-oxoisoquinoline-1-ylamino)-1-propyloxy]-5H-dibenzo[a,d] cycloheptene-10-acetate for the ethyl (R)-10,11-dihydro-3-[3-(1-oxopyridin-2-ylamino)-1-propyloxy]-5H-dibenzo[a, d]cycloheptene-10-acetate, the title compound was prepared as a clear oil: MS (ES) m/e 481.3$(M+H)^+$.

c) (±)-10,1-Dihydro-3-[3-(isoquinoline-1-ylamino)-1-propyloxy]-5H-dibenzo[a,d]cycloheptene-10-acetic Acid According to the procedure of Example 6 (c), except substituting ethyl (±)-10,11-dihydro-3-[3-(isoquinoline-1-ylamino)-1-propyloxy]-5H-dibenzo[a,d]cycloheptene-10-acetate for the ethyl (R)-10,11-dihydro-3-[3-(pyridin-2-ylamino)-1-propyloxy]-5H-dibenzo[a,d]cycloheptene-10-acetate, the title compound was prepared as an amber solid: MS (ES) m/e 453.2$(M+H)^+$. Anal. Calcd for $C_{29}H_{28}N_2O_3.1.3$ TFA.0.25 $H_2O$: C, 62.71; H, 4.96; N, 4.63. Found: C, 62.45; H, 4.92; N, 4.41.

Example 10

Preparation of (±)-10,11-dihydro-3-[3-[4-(ethylthio) pyridin-2-ylamino]-1-propyloxyl-5 H-dibenzo[a,d] cycloheptene-10-acetic Acid a) Ethyl (±)-10,11-dihydro-3-[3-[4-(ethylthio)-1-oxopyridin-2-ylamino]-1-propyloxy]-5-dibenzo[a,d]cycloheptene-10-acetate A solution of ethyl (±)-10,11-dihydro-3-[3-(4-nitro-1-oxopyridin-2-ylamino)-1-propyloxy]-5H-dibenzo[a,d] cycloheptene-10-acetate (300 mg, 0.61 mmol) and sodium thioethylate (145 mg, 1.22 mmol) in DMF (5 mL) was warmed at 70° C. for 3 h. The solvent was removed on the rotavap and the residue was purified by silica gel chromatography (2–6% $CH_3OH/CH_2Cl_2$) to give the title compound (90 mg) as an orange oil: MS (ES) m/e 507.3(M+H)$^+$.

b) Ethyl (±)-10,11-dihydro-3-[3-[4-(ethylthio) pyridin-2-ylamino]-1-propyloxy]-5 H-dibenzo[a,d] cycloheptene-10-acetate A mixture of ethyl (±)-10,11-dihydro-3-[3-[4-(ethylthio)-1-oxopyridin-2-ylamino]-1-propyloxy]-5H-dibenzo[a,d] cycloheptene-10-acetate (60 mg, 0.119 mmol), Fe powder (70 mg), and glacial acetic acid (2 mL) was heated at 100° C. for 1.5 h. The mixture was cooled to RT and diluted with $H_2O$ and EtOAc, and the pH was adjusted to 7–8 with solid $Na_2CO_3$. The layers were separated, and the aqueous layer was extracted with EtOAc. The combined organic layers were washed with $H_2O$, dried ($MgSO_4$), and concentrated to give the title compound (60 mg) as a yellow oil: MS (ES) m/e 491.3(M+H)$^+$.

c) (±)-10,11-Dihydro-3-[3-[4-(ethylthio)pyridin-2-ylamino]-1-propyloxy]-5 H-dibenzo[a,d] cycloheptene-10-acetic Acid According to the procedure of Example 6 (c), except substituting ethyl (±)-10,11-dihydro-3-[3-[4-(ethylthio) pyridin-2-y lamino]-1-propyloxy]-5H-dibenzo[a,d] cycloheptene-10-acetate for the ethyl (R)-10,11-dihydro-3-[3-(pyridin-2-ylamino)-1-propyloxy]-5H-dibenzo[a,d] cycloheptene-10-acetate, the title compound was prepared as a yellow: $^1$H NMR (400 MHz, DMSO-d$_6$) δ7.77-7.76 (d, 1 H), 7.17-7.15 (d, 1 H), 7.13-7.12 (d, 2 H), 7.08-7.07 (m, 1 H), 6.96-6.94(d, 1 H), 6.81-6.80 (s, 1 H), 6.68-6.67 (d, 1 H), 6.52 (s, 1 H), 6.35-6.33 (d, 2 H), 6.30 (s, 1 H), 4.20-4.16 (d, 1 H), 3.99-3.96 (t, 2 H),3.89-3.85 (d, 1 H), 3.65-3.63 (m, 1 H), 3.36-3.32 (m, 2 H), 3.22-3.15 (m, 1 H), 2.96-2.90 (m, 2 H); 2.85-2.78 (m, 1 H), 2.62-2.56(m, 2 H), 1.94-1.90(m, 2 H), 1.26-1.22 (t, 3 H), MS (ES) m/e463.4(M+H)$^+$.

Example 11

Preparation of (±)-10,11-dihydro-2-methyl-3-[3-(pyridin-2-ylamino)-1-propyloxy]-5H-dibenzo[a,d] cycloheptene-10-acetic acid a) Ethyl (±)-10,11-dihydro-2-methyl-3-[3-[N-(tert-butoxycarbonyl)-N-(1-oxopyridin-2-yl)amino]-1-propyloxy]-5H-dibenzo[a,d]cycloheptene-10-acetate NaH (60% dispersion in mineral oil, 0.14 g, 0.37 mmol) was added to a solution of ethyl (±)-10,11-dihydro-3-hydroxy-2-methyl-5H-dibenzo[a,d]cycloheptene-10-acetate (100 mg, 0.32 mmol) in DMSO (2 mL) under argon, and the reaction was stirred at RT for 0.5 hr. A solution of 2-[N-(3-methanesulfonyloxy-1-propyl)-N-(tert-butoxycarbonyl) amino]pyridine-N-oxide (160 mg, 0.4 mmole) in DMSO (1 mL) was then added dropwise. The reaction was stirred at RT under argon for 18 hr, then was quenched with water (20 mL) and extracted with EtOAc. Drying ($MgSO_4$), concentration, and silica gel chromatography (1% MeOH/ $CH_2Cl_2$) gave the title compound (85 mg, 42%) as a colorless oil: MS (ES) m/e 561.3 (M+H)$^+$.

b) Ethyl (±)-10,11-dihydro-2-methyl-3-[3-(1-oxopyridin-2-ylamino)-1-propyloxy]-5H-dibenzo[a, d]cycloheptene-10-acetate TFA (0.16 g, 1.4 mmol) was added dropwise to a solution of ethyl (±)-10,11-dihydro-2-methyl-3-[3-[N-(tert-butoxycarbonyl)-N-(1-oxopyridin-2-yl)amino]-1-propyloxy]-5H-dibenzo[a,d]cycloheptene-10-acetate (80 mg, 0.14 mmole) in dry $CH_2Cl_2$ (3 mL). The reaction was stirred for 5 hr then was concentrated on the rotavap to afford the title compound (60 mg, 43%) as acolorless oil: MS (ES) m/e 461.1 (M+H)$^+$.

c) Ethyl (±)-10,11-dihydro-2-methyl-3-[3-(pyridin-2-ylamino)-1-propyloxy]-5 H-dibenzo[a,d] cycloheptene-10-acetate According to the procedure of Example 6 (b), except substituting ethyl (±)-10,11-dihydro-2-methyl-3-[3-(1-oxopyridin-2-ylamino)-1-propyloxy]-5H-dibenzo[a,d] cycloheptene-10-acetate for the ethyl (R)-10,11-dihydro-3-[3-(]-oxopyridin-2-ylamino)-1-propyloxy]-5H-dibenzo[a,d] cycloheptene-10-acetate, the title compound was prepared as an off-white solid: MS (ES) m/e 417.3 (M+H)$^+$.

d) (±)-10,11-Dihydro-2-methyl-3-[3-(pyridin-2-ylamino)-1-propyloxy]-5H-dibenzo[a,d] cycloheptene-10-acetic Acid According to the procedure of Example 6 (c), except substituting ethyl (±)-10,11-dihydro-2-methyl-3-[3-(pyridin-2-ylamino)-1-propyloxy]-5H-dibenzo[a,d] cycloheptene-10-acetate for the ethyl (R)-10,11-dihydro-3-[3-(pyridin-2-ylamino)-1-propyloxy]-5H-dibenzo[a,d] cycloheptene-10-acetate, the title compound was obtained as an off white solid. $^1$H NMR (400 MHz, CDCl$_3$) δ7.75 (d, 1 H), 7.65 (t, 1 H), 7.15 (m, 3 H), 7.05 (m, 1 H), 6.83 (s, 1 H), 6.7 (d, 1 H), 6.65 (m, 1 H), 6.60 (s,1 H), 4.25 (d, J=15.1 Hz, 1 H), 4.05 (t, 2 H), 3.80 (m, 1 H), 3.75 (d, J=15.1 Hz, 1 H), 3.50 (t, 2 H), 3.25 (dd, 1 H), 2.85 (dd, 1 H), 2.68 (dd, 1 H), 2.60 (dd, 1 H), 2.15 (t, 2 H), 2.10 (s, 3 H); MS (ES) m/e 417.3 (M+H)$^+$.

Example 12

Preparation of (±)-10,11-dihydro-2-(dimethylamino) methyl-7-fluoro-3-[3-(pyridin-2-ylamino)-1-propyloxy]-5H-dibenzo[a,d]cycloheptene-10-acetic Acid a) Ethyl (±)-10,11-dihydro-2-(dimethylamino) methyl-7-fluoro-3-[3-(1-oxopyridin-2-ylamino)-1-propyloxy]-5H-dibenzo[a,d]cycloheptene-10-acetate According to the procedure of Example 6 (a), except substituting ethyl (±)-10,11-dihydro-2-(dimethylamino) methyl-7-fluoro-3-hydroxy-5H-dibenzo[a,d]cycloheptene-10-acetate for the ethyl (R)-10,11-dihydro-3-hydroxy-5H-dibenzo[a,d]cycloheptene-10-acetate ethyl, the title compound was obtained following silica gel chromatography (gradient: 1:1 EtOAc hexanes, then EtOAc, then 20% MeOH/$CH_2Cl_2$, then 30% MeOH/$CH_2Cl_2$): MS (ES) m/e 522.3 (M+H)$^+$.

b) Ethyl (±)-10,11-dihydro-2-(dimethylamino) methyl-7-fluoro-3-[3-(pyridin-2-ylamino)-1-propyloxy]-5H-dibenzo[a,d]cycloheptene-10-acetate According to the procedure of Example 6 (b), except substituting ethyl (±)-10,11-dihydro-2-(dimethylamino) methyl-7-fluoro 3-[3-(1-oxopyridin-2-ylamino)-1-propyloxy]-5H-dibenzo[a,d]cycloheptene-10-acetate for the ethyl (R)-10,11-dihydro-3-[3-(1-oxopyridin-2-ylamino)-1-propyloxy]-5H-dibenzo[a,d]cycloheptene-10-acetate, the title compound was obtained following silica gel chromatography (10% MeOH/$CH_2Cl_2$): MS (ES) m/e 506.2 (M+H)$^+$.

c) (±)-10,11-Dihydro-2-(dimethylamino)methyl-7-fluoro-3-[3-(pyridin-2-ylamino)-1-propyloxy]-5H-dibenzo[a,d]cycloheptene-10-acetic Acid Saponification was conducted according to the procedure of Example 6 (c), except substituting ethyl (±)-10,11-dihydro-2-(dimethylamino)methyl-7-fluoro-3-[3-(pyridin-2-ylamino)-1-propyloxy]-5H-dibenzo[a,d]cycloheptene-10-acetate for the ethyl (R)-10,11-dihydro-3-[3-(pyridin-2-ylamino)-1-propyloxy]-5H-dibenzo[a,d]cycloheptene-10-acetate. The reaction was acidified with glacial HOAc, and the crude product was desalted by chromatography on XAD-2 resin to afford the title compound as a white solid: MS (ES) m/e 478.3 (M+H)$^+$. Anal. Calcd for $C_{30}H_{36}FN_3O_5 \cdot 1.25 H_2O$: C, 64.32; H, 6.92; N, 7.50. Found: C, 63.87; H, 6.47: N, 7.96.

Example 13

Preparation of (S)-10,11-dihydro-3-[3-(4-methylpyridin-2-ylamino)-1-propyloxy]-5 H-dibenzo[a,d]cycloheptene-10-acetic Acid a) Ethyl (S)-10,11-dihydro-3-[3-(4-methyl-1-oxopyridin-2-ylamino)-1-propyloxy]-5 H-dibenzo[a,d]cycloheptene-10-acetate A solution of 2-[(3-hydroxy-1-propyl)amino]-4-methylpyridine-N-oxide (1.72 g, 9.45 mmole) and diethyl azodicarboxylate (1.49 mL, 9.45 mmole) in anhydrous DMF (50 mL) was added dropwise over 10 min to a solution of ethyl (S)-10,11-dihydro-3-hydroxy 5H-dibenzo[a,d]cycloheptene-10-acetate (1.4 g, 4.72 mmole) and triphenylphosphine (2.60 g, 9.92 mmole) in anhydrous DMF (50 mL) at RT under argon. After 19 hr, the reaction was concentrated on the rotavap, and the residue was reconcentrated from xylenes to remove residual DMF. Silica gel chromatography (gradient: 30% EtOAc/hexanes (0.5 L), then EtOAc (1 L), then 5% MeOH/CHCl$_3$) gave the title compound (1.31 g, 60%) as a yellow oil: MS (ES) m/e 461.3 (M+H)$^+$.

b) Ethyl (S)-10,11-dihydro-3-[3-(4-methylpyridin-2-ylamino)-1-propyloxy]-5H-dibenzo[a,d]cycloheptene-10-acetate A mixture of ethyl (S)-10,11-dihydro-3-[3-(4-methyl-1-oxopyridin-2-ylamino)-1-propyloxy]-5H-dibenzo[a,d]cycloheptene-10-acetate (0.86 g, 1.87 mmole), 10% Pd/C (0.86 g, 0.81 mmole), cyclohexene (1.89 mL, 18.7 mmole), and isopropanol (20 mL) was heated at reflux under argon for 19 hr, then the catalyst was removed by filtration through celite®. Silica gel chromatography (1:9:10 MeOH/CH$_2$Cl$_2$/EtOAc) gave the title compound (0.65 g, 78%) as a clear oil: MS (ES) m/e 445.2 (M+H)$^+$.

c) (S)-10,11-Dihydro-3-[3-(4-methylpyridin-2-ylamino)-1-propyloxy]-5H-dibenzo[a,d]cycloheptene-10-acetic Acid A mixture of ethyl (S)-10,11-dihydro-3-[3-(4-methylpyridin-2-ylamino)-1-propyloxy]-5H-dibenzo[a,d]cycloheptene-10-acetate (2.08 g, 4.69 mmole) and 1.0 N NaOH (7.0 ml, 7.0 mmole) in absolute EtOH (45 mL) was warmed in an oil bath set at 45° C. After 18 hr, the reaction was concentrated on the rotavap and the pH was adjusted to 7 with 1.0 N HCl. The solid precipitate was collected and washed with H$_2$O. Drying overnight afforded the title compound (1.61 g, 82%) as a nearly colorless solid: MS (ES) m/e 417.4 (M+H)$^+$. Anal. Calcd for $C_{26}H_{28}N_2O_3 \cdot 1.0 H_2O$: C, 71.87; H, 6.96; N, 6.45. Found: C, 71.63; H, 6.96; N, 6.30.

Example 14

Preparation of (S)-10,11-dihydro-3-[3-[4-(2-propyloxy)pyridin-2-ylamino]-1-propyloxy]-5H-dibenzo[a,d]cycloheptene-10-acetic Acid a) Isopropyl (S)-10,11-dihydro-3-[3-[4-(2-propyloxy)-1-oxopyridin-2-ylamino]-1-propyloxy]-5H-dibenzo[a,d]cycloheptene-10-acetate A mixture of ethyl (S)-10,11-dihydro-3-[3-(4-nitro-1-oxopyridin-2-ylamino)-1-propyloxy]-5H-dibenzo[a,d]cycloheptene-10-acetate (0.2 g, 0.4 mmole) and sodium isopropoxide (0.067 g, 0.8 mmole) in isopropanol (5 mL) was heated at 80° C. for 3.5 hr. then more sodium isopropoxide (0.05 g, 0.6 mmole) was added, and the reaction was stirred at RT overnight. Concentration and silica gel chromatography (gradient: 5%-15% MeOH/CH$_2$Cl$_2$) gave the title compound (0.106 g, 52%) as a light brown oil: MS (ES) 519.3 (M+H)$^+$.

b) Isopropyl (S)-10,11-dihydro-3-[3-[4-(2-propyloxy)pyridin-2-ylamino]-1-propyloxy]-5H-dibenzo[a,d]cycloheptene-10-acetate According to the procedure of Example 13 (b), except substituting isopropyl (S)-10,11-dihydro-3-[3-[4-(2-propyloxy)-1-oxopyridin-2-ylamino]-1-propyloxy]dibenzo[a,d]cycloheptene-10-acetate for the ethyl (S)-10,11-dihydro-3-[3-(4-methyl-1-oxopyridin-2-ylamino)-1-propyloxy]-5H-dibenzo[a,d]cycloheptene-10-acetate, the title compound was obtained as slightly yellow oil following silica gel chromatography (5% MeOH/CH$_2$Cl$_2$): MS (ES) 503.4 (M+H)$^+$.

c) (S)-10,11-Dihydro-3-[3-[4-(2-propyloxy)pyridin-2-ylamino]-1-propyloxy]-5H-dibenzo[a,d]cycloheptene-10-acetic Acid According to the procedure of Example 13 (c), except substituting isopropyl (S)-10,11-dihydro-3-[3-[4-(2-propyloxy)pyridin-2-ylamino]-1-propyloxy]-5H-dibenzo[a,d]cycloheptene-10-acetate for the ethyl (S)-10,11-dihydro-3-[3-(4-methylpyridin-2-ylamino)-1-propyloxy]-5H-dibenzo[a,d]cycloheptene-10-acetate, the title compound was obtained as white powder: MS (ES) 461.3 (M+H)$^+$. Anal. Calcd for $C_{28}H_{32}N_2O_4 \cdot 0.96$ HCl: C, 67.86; H, 6.70; N, 5.65. Found: C, 68.26; H, 6.86; N, 5.25.

Example 15

Preparation of (S)-10,11-dihydro-3-[3-(4-chloropyridin-2-ylamino)-1-propyloxy]-5 H-dibenzo[a,d]cycloheptene-10-acetic Acid a) Ethyl (S)-10,11-dihydro-3-[3-(4-chloro-1-oxopyridin-2-ylamino)-1-propyloxy]-5 H-dibenzo[a,d]cycloheptene-10-acetate A solution of ethyl (S)-10,11-dihydro-3-[3-(4-nitro-1-oxopyridin-2-ylamino)-1-propyloxy]-5H-dibenzo[a,d]cycloheptene-10-acetate (0.47 g, 0.96 mmole) in acetyl chloride (7 mL, 98 mmole) was heated at reflux for 1 hr. The reaction mixture was poured onto ice (50 g), and the pH was adjusted to 8.0 using saturated NaHCO$_3$ (caution: bubbles violently!). The mixture was extracted with CH$_2$Cl$_2$ (2×100 mL), and the combined organic layers were washed sequentially with H$_2$O (50 mL) and brine (50 mL). Drying (MgSO$_4$) and concentration gave the title compound: MS (ES) 481.2 (M+H)$^+$.

b) Ethyl (S)-10,11-dihydro-3-[3-(4-chloropyridin-2-ylamino)-1-propyloxy]-5H-dibenzo[a,d]cycloheptene-10-acetate A mixture of ethyl (S)-10,11-dihydro-3-[3-(4-chloro-1-oxopyridin-2-ylamino)-1-propyloxy]-5H-dibenzo[a,d]cycloheptene-10-acetate (0.13 g, 0.27 mmole) and 2.0 M $PCl_3$ in $CH_2Cl_2$ (8 mL, 16 mmole) was heated at reflux for 22 hr. The reaction mixture was cooled and poured onto ice (200 g), and the pH was adjusted to 12 using 40% NaOH. $CH_2Cl_2$ (2×100 mL) extraction, drying ($MgSO_4$), concentration, and silica gel chromatography (4% MeOH/$CH_2Cl_2$) gave the title compound (93 mg, 74%) as light yellow oil: MS (ES) 465.3 (M+H)$^+$.

c) (S)-10,11-Dihydro-3-[3-(4-chloropyridin-2-ylamino)-1-propyloxy]-5H-dibenzo[a,d]cycloheptene-10-acetic Acid According to the procedure of Example 13 (c), except substituting ethyl (S)-10,11-dihydro-3-[3-(4-chloropyridin-2-ylamino)-1-propyloxy]-5H-dibenzo[a,d]cycloheptene-10-acetate for the ethyl (S)-10,11-dihydro-3-[3-(4-methylpyridin-2-ylamino)-1-propyloxy]-5H-dibenzo[a,d]cycloheptene-10-acetate, the title compound was obtained as off-white powder: MS (ES) 437.2 (M+H)$^+$. Anal. Calcd for $C_{25}H_{25}N_2O_3$.1.0 HCl: C, 63.43;. H, 5.54; N, 5.92. Found: C, 63.11; H, 5.82; N, 5.62.

Example 16

Preparation of (S)-10,11-dihydro-3-[3-[4-(dimethylamino)pyridin-2-ylamino]-1-propyloxy]-5H-dibenzo[a,d]cycloheptene-10-acetic Acid a) Ethyl (S)-10,11-dihydro-3-[3-(4-chloro--oxopyridin-2-ylamino)-1-propyloxy]-5 H-dibenzo[a,d]cycloheptene-10-acetate A solution of ethyl (±)-10,11-dihydro-3-]3-(4-nitro-1-oxopyridin-2-ylamino)-1-propyloxy]-5H-dibenzo[a,d]cycloheptene-10-acetate (0.47 g, 0.96 mmole) in acetyl chloride (7 mL, 98 mmole) was heated at reflux for 1 hr. The reaction mixture was poured onto ice (50 g), and the pH was adjusted to 8.0 using saturated $NaHCO_3$ (caution: bubbles violently!). The mixture was extracted with $CH_2Cl_2$ (2×100 mL), and the combined organic layers were washed sequentially with $H_2O$ (50 mL) and brine (50 mL). Drying ($MgSO_4$) and concentration gave crude title compound which was carried forward without further purification. MS (ES) 481.3 (M+H)$^+$.

b) Ethyl (S)-10,11-dihydro-3-[3-[4-(dimethylamino)1-oxopyridin-2-ylamino]-1-propyloxy]-5H-dibenzo[a,d]cycloheptene-10-acetate A mixture of ethyl (S)-10,11-dihydro-3-[3-(4-chloro-1-oxopyridin-2-ylamino)-1-propyloxy]-5H-dibenzo[a,d]cycloheptene-10-acetate (0.96 mmole) and 2.0 M dimethylamine in MeOH (3 mL, 6 mmole) was refluxed for 16 hr. Concentration and silica gel chromatography (7% MeOH/$CH_2Cl_2$) gave the title compound (0.049 g, 10%) as a light brown powder: MS (ES) 490.3 (M+H)$^+$. Unchanged ethyl (S)-10,11-dihydro-3-[3-(4-chloro-1-oxopyridin-2-ylamino)-1-propyloxy]-5H-dibenzo[a,d]cycloheptene-10-acetate was also recovered from the chromatographic purification.

c) Ethyl (S)-10,11-dihydro-3-[3-[4-(dimethylamino)pyridin-2-ylamino-]1-propyloxy]-5H-dibenzo[a,d]cycloheptene-10-acetate According to the procedure of Example 13 (b), except substituting ethyl (S)-10,11-dihydro-3-[3-[4-(dimethylamino)-1-oxopyridin-2-ylamino]-1-propyloxy]-5H-dibenzo[a,d]cycloheptene-10-acetate for the ethyl (S)-10,11-dihydro-3-[3-(4-methyl-1-oxopyridin-2-ylamino)-1-propyloxy]-5H-dibenzo[a,d]cycloheptene-10-acetate, the title compound was obtained as white powder following silica gel chromatography (8% MeOH/$CH_2Cl_2$): MS (ES) 474.3 (M+H)$^+$.

d) (S)-10,11-Dihydro-3-[3-[4-(dimethylamino)pyridin-2-ylamino-]1-propyloxy]-5 H-dibenzo[a,d]cycloheptene-10-acetic Acid According to the procedure of Example 13 (c), except substituting ethyl (S)-10,11-dihydro-3-[3-[4-(dimethylamino)pyridin-2-ylamino]-1-propyloxy]-5H-dibenzo[a,d]cycloheptene-10-acetate for the ethyl (S)-10,11-dihydro-3-[3-(4-methylpyridin-2-ylamino)-1-propyloxy]-5H-dibenzo[a,d]cycloheptene-10-acetate, the title compound was obtained as white powder: MS (ES) 446.2 (M+H)$^+$. Anal. Calcd for $C_{27}H_{31}N_3O_3$.0.5 $H_2O$. 1.0 HCl: C, 66.04; H, 6.77; N, 8.56. Found: C, 65.96; H, 6.60; N, 8.26.

Example 17

Preparation of (S)-10,11-dihydro-3-[3-(4-ethoxypyridin-2-ylamino)-1-propyloxy]-5 H-dibenzo[a,d]cycloheptene-10-acetic Acid a) Ethyl (S)-10,11-dihydro-3-[3-(4-ethoxy-1-oxopyridin-2-ylamino)-1-propyloxy]-5 H-dibenzo[a,d]cycloheptene-10-acetate According to the procedure of Example 2 (a), except substituting ethyl (S)-10,11-dihydro-3-[3-(4-nitro-1-oxopyridin-2-ylamino)-1-propyloxy]-5H-dibenzo[a,d]cycloheptene-10-acetate (496.9 mg, 1.01 mmol) for the ethyl (±)-10,11-dihydro-3-[3-(4-nitro-1-oxopyridin-2-ylamino)-1-propyloxy]-5H-dibenzo[a,d]cycloheptene-10-acetate, and using 0.53 M NaOEt (4.0 mL, 2.12 mmol) and absolute ethanol (10 mL) in the displacement reaction, the title compound (456.2 mg, 92%) was prepared: MS (ES) m/e 491 (M+H)$^+$.

b) Ethyl (S)-10,11-dihydro-3-[3-(4-ethoxypyridin-2-ylamino)-1-propyloxy]-5H-dibenzo[a,d]cycloheptene-10-acetate According to the procedure of Example 2 (b), except substituting ethyl (S)-10,11-dihydro-3-[3-(4-ethoxy-1-oxopyridin-2-ylamino)-1-propyloxy]-5H-dibenzo[a,d]cycloheptene-10-acetate (456.2 mg, 0.93 mmole) for the ethyl (±)-10,11-dihydro-3-[3-(4-ethoxy-1-oxopyridin-2-ylamino)-1-propyloxy]-5H-dibenzo[a,d]cycloheptene-10-acetate, the title compound (475.2 mg, quantitative) was prepared: MS (ES) m/e 475 (M+H)$^+$.

c) (S)-10,11-Dihydro-3-[3-(4-ethoxypyridin-2-ylamino)-1-propyloxy]-5H-dibenzo[a,d]cycloheptene-10-acetic acid 1.0 N NaOH (2.0 mL, 2.0 mmole) was added to a solution of ethyl (S)-10,11-dihydro-3-[3-(4-ethoxypyridin-2-ylamino)-1-propyloxy]-5H-dibenzo[a,d]cycloheptene-10-acetate (475.2 mg, 1.0 mmol) in absolute ethanol (10 mL), and the solution was warmed at 50° C. in an oil bath. After 20 hr, the reaction was concentrated and the aqueous residue was cooled to 0° C. in an ice bath. 1.0 N aqueous HCl (2.0 mL, 2.0 mmole) was slowly added with stirring. An opaque solid residue precipitated and was collected on a sintered glass funnel. Drying in a vacuum desiccator overnight gave the title compound (452.6 mg, 83%): MS (ES) m/e 447 (M+H)$^+$. Anal. Calcd for $C_{27}H_{30}N_2O_4 \cdot 0.20\ H_2O \cdot 1.75\ HCl$: C, 63.10; H, 6.30; N, 5.45. Found: C, 63.10; H, 5.98; N, 5.38.

Example 18

Preparation of (±)-10,11-dihydro-7-fluoro-3-[3-(pyridin-2-ylamino)-1-propyloxy]-5H-dibenzo[a,d]cycloheptene-10-acetate a) Ethyl (±)-10,11-dihydro-7-fluoro-3-[3-(1-oxopyridin-2-ylamino)-1-propyloxy]-5H-dibenzo[a,d]cycloheptene-10-acetate According to the procedure of Example 6 (a), except substituting ethyl (±)-10,11-dihydro-7-fluoro-3-hydroxy-5H-dibenzo[a,d]cycloheptene-10-acetate for the ethyl (R)-10,11-dihydro-3-hydroxy-5H-dibenzo[a,d]cycloheptene-10-acetate, the title compound was obtained as a colorless oil following silica gel chromatography (gradient: 1:1 EtOAc/hexanes, then EtOAc, then 4% MeOH/CH$_2$Cl$_2$): MS (ES) m/e 465.3 (M+H)$^+$.

b) Ethyl (±)-10,11-dihydro-7-fluoro-3-[3-(pyridin-2-ylamino)-1-propyloxy]-5 H-dibenzo[a,d]cycloheptene-10-acetate According to the procedure of Example 6 (b), except substituting ethyl (±)-10,11-dihydro-7-fluoro-3-[3-(1-oxopyridin-2-ylamino)-1-propyloxy]-5H-dibenzo[a,d]cycloheptene-10-acetate for the ethyl (R)-10,11-dihydro-3-[3-(1-oxopyridin-2-ylamino)-1-propyloxy]-5H-dibenzo[a,d]cycloheptene-10-acetate, the title compound was obtained: MS (ES) m/e 449.2 (M+H)$^+$.

c) (±)-10,11-Dihydro-7-fluoro-3-[3-(pyridin-2-ylamino)-1-propyloxy]-5H-dibenzo[a,d]cycloheptene-10-acetic acid According to the procedure of Example 6 (c), except substituting ethyl (±)-10,11-dihydro-7-fluoro-3-[3-(pyridin-2-ylamino)-1-propyloxy]-5H-dibenzo[a,d]cycloheptene-10-acetate for the ethyl (R)-10,11-dihydro-3-[3-(pyridin-2-ylamino)-1-propyloxy]-5H-dibenzo[a,d]cycloheptene-10-acetate, the title compound was obtained: MS (ES) m/e 421.1 (M+H)$^+$. Anal. Calcd for $C_{25}H_{25}FN_2O_3 \cdot 0.5\ H_2O$: C, 69.99; H, 6.10; N, 6.52. Found: C, 69.86; H, 5.90; N, 6.35.

Example 19

Preparation of (±)-10,11-dihydro-6-methyl-3-[3-(pyridin-2-ylamino)-1-propyloxy]-5 H-dibenzo[a,d]cycloheptene-10-acetic acid a) Ethyl (±)-10,11-dihydro-6-methyl-3-[3-(1-oxopyridin-2-ylamino)-1-propyloxy]-5 H-dibenzo[a,d]cycloheptene-10-acetate According to the procedure of Example 6 (a), except substituting ethyl (±)-10,11-dihydro-3-hydroxy-6-methyl-5H-dibenzo[a,d]cycloheptene-10-acetate for the ethyl (R)-10,11-dihydro-3-hydroxy-5H-dibenzo[a,d]cycloheptene-10-acetate, the title compound was obtained as a colorless oil following silica gel chromatography (gradient: 1:1 EtOAc/hexanes, then EtOAc, then 4% MeOH/CH$_2$Cl$_2$): MS (ES) m/e 461.3 (M+H)$^+$.

b) Ethyl (±)-10,11-dihydro-6-methyl-3-[3-(pyridin-2-ylamino)-1-propyloxy]-5 H-dibenzo[a,d]cycloheptene-10-acetate According to the procedure of Example 6 (b), except substituting ethyl (±)-10,11-dihydro-6-methyl-3-[3-(1-oxopyridin-2-ylamino)-1-propyloxy]-5H-dibenzo[a,d]cycloheptene-10-acetate for the ethyl (R)-10,11-dihydro-3-[3-(1-oxopyridin-2-ylamino)-1-propyloxy]-5H-dibenzo[a,d]cycloheptene-10-acetate, the title compound was obtained following silica gel chromatography (1% MeOH/CH$_2$Cl$_2$): MS (ES) m/e 445.3 (M+H)$^+$.

c) (±)-10,11-Dihydro-6-methyl-3-[3-(pyridin-2-ylamino)-1-propyloxy]-5H-dibenzo[a,d]cycloheptene-10-acetic acid According to the procedure of Example 6 (c), except substituting ethyl (±)-10,11-dihydro-6-methyl-3-[3-(pyridin-2-ylamino)-1-propyloxy]-5H-dibenzo[a,d]cycloheptene-10-acetate for the ethyl (R)-10,11-dihydro-3-[3-(pyridin-2-ylamino)-1-propyloxy]-5H-dibenzo[a,d]cycloheptene-10-acetate, the title compound was obtained as a white solid: MS (ES) m/e 417.3 (M+H)$^+$. Anal. Calcd for $C_{26}H_{28}N_2O_3 \cdot 1.25\ H_2O$: C, 71.13; H, 7.02; N, 6.38. Found: C, 71.33; H, 6.67; N, 6.01.

Example 20

Preparation of (S)-10,11-dihydro-3-[3-(4-aminopyridin-2-ylamino)-1-propyloxy]-5 H-dibenzo[a,d]cycloheptene-10-acetic acid a) Ethyl (S)-10,11-dihydro-3-[3-(4-nitro-1-oxopyridin-2-ylamino)-1-propyloxy]-5H-dibenzo[a,d]cycloheptene-10-acetate A solution of diisopropyl azodicarboxylate (1.7 mL, 8 mmole) in THF (10 mL) was added dropwise to a solution of ethyl (S)-10,11-dihydro-3-hydroxy-5H-dibenzo[a,d]cycloheptene-10-acetate (426.5 mg, 1.5 mmole), 2-[(3-hydroxy-1-propyl)amino]-4-nitropyridine-N-oxide (1.7 g, 8 mmole), and triphenylphosphine (2.5 g. 8 mmole) in anhydrous DMF (20 mL) at 0° C. under argon. The yellow solution was kept at 0° C. for 10 min, then was warmed to RT. After 23 hr, the reaction was concentrated. Silica gel chromatography (gradient: 30%-100% EtOAc/hexanes) gave the title compound (2.7 g, 81%) as an orange foam: MS (ES) m/e 491.8 (M+H)$^+$.

b) Ethyl (S)-10,11-dihydro-3-[3-(4-aminopyridin-2-ylamino)-1-propyloxy]-5H-dibenzo[a,d]cycloheptene-10-acetate A mixture of ethyl (S)-10,11-dihydro-3-[3-(4-nitro-1-oxopyridin-2-ylamino)-1-propyloxy]-5H-dibenzo[a,d]cycloheptene-10-acetate (2.7 g, 6 mmole), cyclohexene (6 mL, 60 mmole), 10% Pd/C (1.2 g, 1.10 mmole), and isopropanol (30 mL) was heated at reflux under argon for 20.5 hr, then was hot-filtered through celite®. The filter pad was washed with hot EtOAc, and the combined filtrates were concentrated. The residue was chromatographed on silica gel (5% MeOH/CHCl$_3$) to afford the title compound (2.4 g, 98%) as a colorless foam: MS (ES) m/e 445.9 (M+H)$^+$.

c) (S)-10,11-Dihydro-3-[3-(4-aminopyridin-2-ylamino)-1-propyloxy]-5H-dibenzo[a,d]cycloheptene-10-acetic acid A mixture of ethyl (S)-10,11-dihydro-3-[3-(4-aminopyridin-2-ylamino)-1-propyloxy]-5H-dibenzo[a,d]cycloheptene-10-acetate (2.4 g, 5 mmole), LiOH.H$_2$O (0.3 g, 7 mmole), THF (30 mL), and H$_2$O (10 mL) was stirred at RT for 48 hr, then was concentrated. The residue was diluted with H$_2$O and extracted with Et$_2$O. The Et$_2$O layers were discarded. The aqueous layer was stirred with gentle warming under vacuum to remove residual organic solvents, then was filtered. The resulting aqueous solution was stirred at RT while the pH was slowly and carefully adjusted to 5.5–6.0 with 1.0 N HCl The mixture was stirred for 0.5 hr, then the solid was collected by suction filtration and washed with plenty of $H_2O$. Drying in high vacuum at 60° C. gave the title compound (1.0 g, 42%) as a glassy solid: MS (ES) m/e 417.7 (M+H)$^+$. Anal. Calcd for $C_{25}H_{27}N_3O_3$ 1.4 HCl (468.554): C, 64.08; H, 6.11; N, 8.97. Found: C, 64.16; H, 6.20; N, 8.71.

Example 21

Preparation of (±)-10,11-dihydro-3-[3-(4-methylpyridin-2-ylamino)-1-propyloxy]dibenzo[b,f]oxepine-10-acetic acid a) Ethyl (±)-10,11-dihydro-3-[3-(4-methyl-1-oxopyridin-2-ylamino)-1-propyloxy]dibenzo[b,f]oxepine-10-acetate A mixture of ethyl (±)-10,11-dihydro-3-hydroxydibenzo[b,f]oxepine-10-acetate (257 mg, 0.86 mmole), 2-[(3-bromo-1-propyl)amino]-4-methylpyridine-N-oxide hydrobromide (308 mg, 0.94 mmole), NaOH pellets (110 mg, 2.75 mmole), and $CH_3CN$ (4 mL) was stirred at RT under argon overnight. The mixture was filtered and the solids were washed with $CH_3CN$. The filtrate was concentrated, and the residue was flash chromatographed on silica gel (1–2.5% $CH_3OH/CH_2Cl_2$) to afford the title compound (190 mg, 48%) as a white foam: MS (ES) m/e 462.6 (M+H)$^+$.

b) Ethyl (±)-10,11-dihydro-3-[3-(4-methylpyridin-2-ylamino)-1-propyloxy]dibenzo[b,f]oxepine-10-acetate A mixture of ethyl (±)-10,11-dihydro-3-[3-(4-methyl-1-oxopyridin-2-ylamino)-1-propyloxy]dibenzo[b,j]oxepine-10-acetate (183 mg, 0.4 mmole), 10% Pd/C (85 mg, 0.08 mmole), cyclohexene (810 mg, 8 mmole), and isopropanol (4 mL) was heated at reflux overnight. The catalyst was removed by filtration through celite®, and the filter cake was washed with ether. The filtrate was concentrated to afford the title compound (122 mg, 68%) as a clear oil: MS (ES) m/e 446.9 (M+H)$^+$.

c) (±)-10,11-Dihydro-3-[3-(4-methylpyridin-2-ylamino)-1-propyloxy]dibenzo[b,f]oxepine-10-acetic acid A mixture of ethyl (±)-10,11-dihydro-3-[3-(4-methylpyridin-2-ylamino)-1-propyloxy]dibenzo[b,f]oxepine-10-acetate (119 mg, 0.27 mmole) and 0.991 N NaOH (0.545 mL, 0.54 mmole) in absolute EtOH (2 mL) was warmed in an oil bath set at 45° C. After 20 hr, the reaction was concentrated on the rotavap, and the residue was dissolved in $H_2O$ (1.5 mL). The solution was filtered to remove insoluble material, and the filtrate was carefully neutralized by dropwise addition of 1.0 N HCl (0.54 mL, 0.54 mmole). The precipitate was collected and dried in high vacuum to afford the title compound (68 mg, 58%) as a white solid: MS (ES) m/e 418.9 (M+H)$^+$. Anal. Calcd for $C_{25}H_{26}N_2O_4$. 0.45 HCl: C, 69.05; H, 6.13; N. 6.44. Found: C, 69.25; H, 6.27; N. 6.16.

Example 22

Preparation of (±)-10,11-dihydro-3-[2-[6-(methylamino)pyridin-2-yl]-1-ethoxy]dibenzo[b,f]oxepine-10-acetic acid a) Ethyl (±)-10,11-dihydro-3-[2-[6-[N-tert-butoxycarbonyl)-N-methylamino]pyridin-2-yl]-1-ethoxy]dibenzo[b,f]oxepine-10-acetate A solution of 6-[N-(tert-butoxycarbonyl)-N-methylamino]-2-pyridylethanol (397 mg, 1.58 mmole) and diisopropyl azodicarboxylate (0.31 mL, 1.58 mmole) in anhydrous $CH_2Cl_2$ (8 mL) was added dropwise over 10 min to a solution of ethyl (±)-10, 11-dihydro-3-hydroxydibenzo[b,f]oxepine-10-acetate (186 mg, 0.63 mmole) and triphenylphosphine (413 mg, 1.58 mmole) in anhydrous $CH_2Cl_2$ (3.2 mL) at RT under argon. After 22 hr, the reaction was concentrated on the rotavap, and the residue was flash chromatographed on silica gel (2–13% EtOAc/hexanes) to give the title compound (146 mg, 44%) as a clear oil: MS (ES) m/e 533.0 (M+H)$^+$.

b) Ethyl (±)-10,11-dihydro-3-[2-[6-(methylamino)pyridin-2-yl]-1-ethoxy]dibenzo[b,f]oxepine-10-acetic acid 4 N HCl in dioxane (1.3 mL, 5.2 mmole) was added dropwise to a solution of ethyl (±)-10,11-dihydro-3-[2-[6[N-tert-butoxycarbonyl)-N-methylamino]pyridin-2-yl]-1-ethoxy]dibenzo[b,f]oxepine-10-acetate (140 mg, 0.26 mmole) in $CH_2Cl_2$ (1.3 mL) After 12 hr, the mixture was concentrated, and the residue was triturated with ether to afford the title compound as a white solid: MS (ES) m/e 432.9 (M+H)$^+$.

c) (±)-10,11-Dihydro-3-[2-[6-(methylamino)pyridin-2-yl]-1-ethoxy]dibenzo[b,f]oxepine-10-acetic acid A mixture of ethyl (±)-10,11-dihydro-3-[2-[6 (methylamino)pyridin-2-yl]-1-ethoxy]dibenzo[b,f]oxepine-10-acetic acid (0.26 mmole) and 0.991 N NaOH (0.525 mL, 0.52 mmole) in absolute EtOH (2 mL) was warmed in an oil bath set at 50° C. After 20 hr, the reaction was concentrated on the rotavap and the residue was dissolved in $H_2O$ (1.5 mL). The solution was filtered to remove insoluble material, and the filtrate was carefully neutralized by dropwise addition of 1.0 N HCl. The precipitate was collected and dried in high vacuum to afford the title compound (72 mg, 30% for 2 steps) as an off-white solid: MS (ES) m/e 405.0 (M+H)$^+$. Anal. Calcd for $C_{24}H_{24}N_2O_4$.1.25HCl. 0.25$H_2O$: C, 63.42; H, 5.71; N, 6.16. Found: C, 63.35; H, 5.9; N, 6.16.

Example 23

Preparation of (S)-10,11-dihydro-3-[3-(2-aminopyridin-4-yl)-1-propyloxy]-5H-dibenzo[a,d]cycloheptene-10-acetic acid a) 3-(2-Aminopyridin-4-yl)propan-1-ol A suspension of 3-(2-aminopyridin-4-yl)propanoic acid hydrochloride (0.73 g. 3.60 mmol, prepared according to WO94/14776 in THF (10 mL) was added over 45 min to lithium aluminum hydride (12 mL, 12 mmol, 1M in THF) at 0° C. The ice bath was removed and the reaction was allowed to stir at RT for 4.5 h. The reaction was cooled to 0° C. diluted with toluene (22 mL) and quenched by the sequential addition of $H_2O$ (0.86 mL) and NaF (1.54 g). The resulting suspension was stirred at 0° C. for 45 min. The reaction mixture was filtered and the precipitate was washed with additional 10% MeOH in $CHCl_3$. The combined filtrates were concentrated under reduced pressure. Flash chromatography (10% MeOH/$CHCl_3$, silica gel) gave 0.25 g of the desired material as a clear oil: MS(ES+) m/z 152.7 [M+H]$^+$.

b) Ethyl (S)-10,11-dihydro-3-[3-(2-aminopyridin-4-yl)-1-propyloxy]-5H-dibenzo[a,d]cycloheptene-10-acetate A solution of Example 1(a) (0.23 g, 1.51 mmol) and di-isopropylazadicarboxylate (0.29 mL, 1.50 mmol) in CH₂Cl₂ (7.5 mL) was added dropwise to a solution of triphenylphosphine (0.39 g, 1.50 mmol) and ethyl 2-[(10S)-3-hydroxy-10,11-dihydro-5H-dibenzo[a,d]cyclohepten-10-yl]acetate (0.30 g, 1.00 mmol) in CH₂Cl₂ (5 mL) at 0° C. The ice bath was removed and the reaction was allowed to warm to RT. After 18 h, the solvent was removed under reduced pressure. Flash chromatogrpahy (50% EtOAc/hexanes to 100% EtOAc, silica gel) gave 0.32 g of material that contained the desired product. A second purification by flash chromatography (75% to 90% EtOAc/hexanes, silica gel) gave 0.23 g of the desired material: MS(ES+) m/z 430.9 [M+H]⁺.

c) (S)-10,11-dihydro-3-[3-(2-aminopyridin-4-yl)-1-propyloxy]-5H-dibenzo[a,d]cycloheptene-10-acetic acid The compound of Example 1(b) (0.22 g, 0.50 mmol) was dissolved in 1N NaOH (0.77 mL, 0.77 mmol), EtOH (3 mL) and THF (3 mL). After heating the reaction at 50° C. for 18 h, the solvent was removed under reduced pressure. The residue was dissolved in H₂O (4 mL) and filtered. The filtrate was acidified with 30% TFA in H₂O and the resulting precipitate was collected. Preparative HPLC (Hamilton PRP-1®, 3% CH₃CN/H₂O-0.% TFA) gave 10 mg of the desired material as a hygroscopic solid: MS(ES+) m/z 402.6 [M+H]⁺.

Example 24
Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 25
Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 26
Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:
1. A compound according to formula (I):

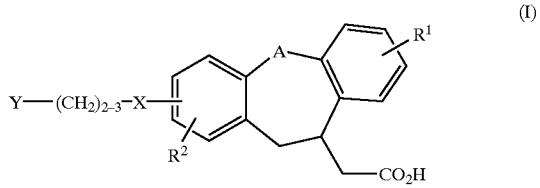

wherein:
A is CH₂ or O;
R¹ is H, halo or C₁₋₆alkyl;
R² is H, C₁₋₆alkyl or CH₂NR″R″;
X is O or CH₂;
Y is

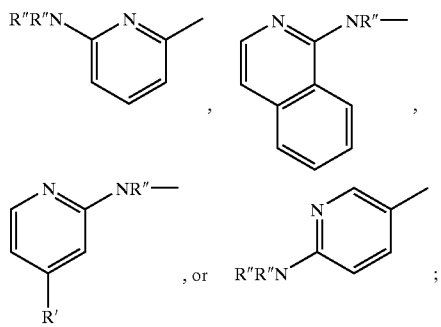

G is NR″, S or O;
R' is H, C₁₋₆alkyl, OC₁₋₆alkyl, SC₁₋₆alkyl, NR″R″ or halo;
each R″ independently is H or C₁₋₆alkyl; and
s is 0, 1, or 2;

or a pharmaceutically acceptable salt thereof.
2. A compound according to claim 1 in which Y is

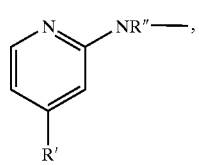

wherein R' is H, C₁₋₄alkyl, OC₁₋₄alkyl, SC₁₋₄alkyl, NR″R″ or Cl and each R″ independently is H or C₁₋₄alkyl.
3. A compound according to claim 1 in which Y is

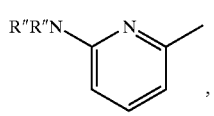

wherein each R″ is H or C₁₋₄alkyl.
4. A compound according to claim 1 in which Y is

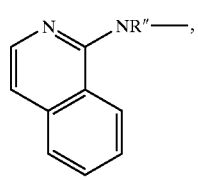

wherein R″ is H or C₁₋₄alkyl.
5. A compound according to claim 1 which is:
(±)-10,11-Dihydro-3-[2-(6-aminopyridin-2-yl)-1-ethoxy]-5H-dibenzo[a,d]cycloheptene-10-acetic acid;

(±)-10,11-Dihydro-3-[4-(pyridin-2-ylamino)-1-butyl]-5H-dibenzo[a,d]cycloheptene-10-acetic acid;

(±)-10,11-Dihydro-3-[3-(4-ethoxypyridin-2-ylamino)-1-propyloxy]-5H-dibenzo[a,d]cycloheptene-10-acetic acid;

(S)-10,11-Dihydro-3-[3-(pyridin-2-ylamino)-1-propyloxy]-5H-dibenzo[a,d]cycloheptene-10-acetic acid;

(R)-10,11-Dihydro-3-[3-(pyridin-2-ylamino)-1-propyloxy]-5H-dibenzo[a,d]cycloheptene-10-acetic acid;

(±)-10,11-Dihydro-3-[3-(isoquinoline-1-ylamino)-1-propyloxy]-5H-dibenzo[a,d]cycloheptene-10-acetic acid;

(±)-10,11-Dihydro-7-fluoro-3-[3-(pyridin-2-ylamino)-1-propyloxy]-5H-dibenzo[a,d]cycloheptene-10-acetic acid;

(S)-10,11-Dihydro-3-[3-(4-methylpyridin-2-ylamino)-1-propyloxy]-5H-dibenzo[a,d]cycloheptene-10-acetic acid;

(S)-10,11-Dihydro-3-[3-(4-ethoxypyridin-2-ylamino)-1-propyloxy]-5H-dibenzo[a,d]cycloheptene-10-acetic acid;

(±)-10,11-Dihydro-6-methyl-3-[3-(pyridin-2-ylamino)-1-propyloxy]-5H-dibenzo[a,d]cycloheptene-10-acetic acid;

(±)-10,11-Dihydro-2-(dimethylamino)methyl-7-fluoro-3-[3-(pyridin-2-ylamino)-1-propyloxy]-5H-dibenzo[a,d]cycloheptene-10-acetic acid;

(S)-10,11-Dihydro-3-[4-(2-propyloxy)pyridin-2-ylamino]-1-propyloxy]-5H-dibenzo[a,d]cycloheptene-10-acetic acid;

(S)-10,11-Dihydro-3-[2-[6-(methylamino)pyridin-2-yl]-1-ethoxy]-5H-dibenzo[a,d]cycloheptene-10-acetic acid;

(S)-10,11-Dihydro-3-[3-[4-(dimethylamino)pyridin-2-ylamino]-1-propyloxy]-5H-dibenzo[a,d]cycloheptene-10-acetic acid;

(±)-10,11-Dihydro-3-[3-[4-(ethylthio)pyridin-2-ylamino]-1-propyloxy]-5H-dibenzo[a,d]cycloheptene-10-acetic acid;

(S)-10,11-Dihydro-3-[3-(4-chloropyridin-2-ylamino)-1-propyloxy]-5H-dibenzo[a,d]cycloheptene-10-acetic acid;

(±)-10,11-Dihydro-2-methyl-3-[3-(pyridin-2-ylamino)-1-propyloxy]-5H-dibenzo[a,d]cycloheptene-10-acetic acid;

(S)-10,11-Dihydro-3-[3-(4-aminopyridin-2-ylamino)-1-propyloxy]-5H-dibenzo[a,d]cycloheptene-10-acetic acid;

(±)-10,11-Dihydro-3-[3-(4-methylpyridin-2-ylamino)-1-propyloxy]-dibenzo[b,f]oxepine-10-acetic acid;

(±)-10,11-Dihydro-3-[2-[6-(methylamino)pyridin-2-yl]-1-ethoxy]-dibenzo[b,f]oxepine-10-acetic acid; or (S)-10,11-Dihydro-3-[3-(2-aminopyridin-4-yl)-1-propyloxy]-5H-dibenzo[a,d]cycloheptene-10-acetic acid;

or a pharmaceutically acceptable salt thereof.

6. A pharmaceutical composition which comprises a compound according to claim 1 and a pharmaceutically acceptable carrier.

7. A pharmaceutical composition which comprises a compound according to claim 1, an antineoplastic agent and a pharmaceutically acceptable carrier.

8. The pharmaceutical composition according to claim 7 wherein the antineoplastic agent is topotecan.

9. The pharmaceutical composition according to claim 7 wherein the antineoplastic agent is cisplatin.

10. A compound according to formula (II):

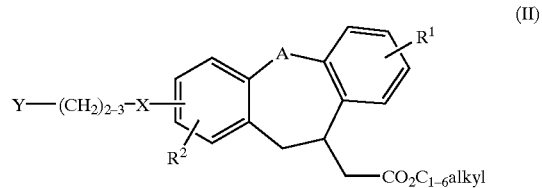

wherein:
A is $CH_2$ or O;
$R^1$ is H, halo or $C_{1-6}$alkyl;
$R^2$ is H, $C_{1-6}$alkyl or $CH_2NR''R''$;
X is O or $CH_2$;
Y is

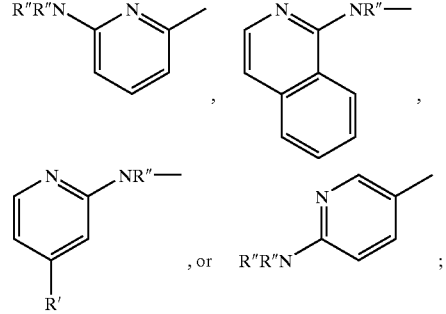

G is NR'', S or O;
R' is H, $C_{1-6}$alkyl, $OC_{1-6}$alkyl, $SC_{1-6}$alkyl, $NR''R''$ or halo;
each R'' independently is H or $C_{1-6}$alkyl; and
s is 0, 1, or 2;

or a pharmaceutically acceptable salt thereof.

* * * * *